US012745929B2

(12) United States Patent
Eren

(10) Patent No.: US 12,745,929 B2
(45) Date of Patent: Sep. 29, 2026

(54) MEDICAL STRING KIT

(71) Applicant: Efrem Eren, Southampton (GB)

(72) Inventor: Efrem Eren, Southampton (GB)

( * ) Notice: Subject to any disclaimer, the term of this patent is extended or adjusted under 35 U.S.C. 154(b) by 820 days.

(21) Appl. No.: 17/295,029

(22) PCT Filed: Nov. 19, 2019

(86) PCT No.: PCT/GB2019/053272
§ 371 (c)(1),
(2) Date: May 18, 2021

(87) PCT Pub. No.: WO2020/104787
PCT Pub. Date: May 28, 2020

(65) Prior Publication Data
US 2021/0393172 A1 Dec. 23, 2021

(30) Foreign Application Priority Data

Nov. 19, 2018 (GB) ...................................... 1818843
Mar. 18, 2019 (GB) ...................................... 1903657

(51) Int. Cl.
*A61B 5/145* (2006.01)
*A61B 5/00* (2006.01)
*A61B 10/00* (2006.01)
*A61M 31/00* (2006.01)
*B01L 3/00* (2006.01)

(52) U.S. Cl.
CPC ...... *A61B 5/14507* (2013.01); *A61B 5/14503* (2013.01); *A61B 5/4233* (2013.01); *A61B 10/0045* (2013.01); *A61M 31/00* (2013.01); *B01L 3/5021* (2013.01); *A61B 2010/0061* (2013.01); *B01L 2300/0832* (2013.01)

(58) Field of Classification Search
None
See application file for complete search history.

(56) References Cited

U.S. PATENT DOCUMENTS 2,099,931 A * 11/1937 Fourness ................ A61F 13/34 604/375
3,528,429 A 9/1970 Beal et al.
3,683,890 A 8/1972 Beal
5,391,158 A * 2/1995 Peters ................ A61J 15/0007 604/270
5,611,787 A 3/1997 Demeter et al.
5,738,110 A 4/1998 Beal et al.
(Continued)

FOREIGN PATENT DOCUMENTS

SU 1115757 A * 9/1984
WO 01/15604 A1 3/2001
(Continued)

OTHER PUBLICATIONS

Machine translation of SU 1115757A retrieved from espacenet.com (Year: 2026).*

*Primary Examiner* — Jacqueline Cheng
*Assistant Examiner* — Samuel C Kim
(74) *Attorney, Agent, or Firm* — BakerHostetler

(57) ABSTRACT

An apparatus comprising a string for insertion into the oesophagus of a patient, the string comprising proximal end and a distal end, wherein the string forms a structure at the distal end thereof to assist in the insertion of the string into the patient.

9 Claims, 36 Drawing Sheets

(56) References Cited

U.S. PATENT DOCUMENTS

Figure 1B:
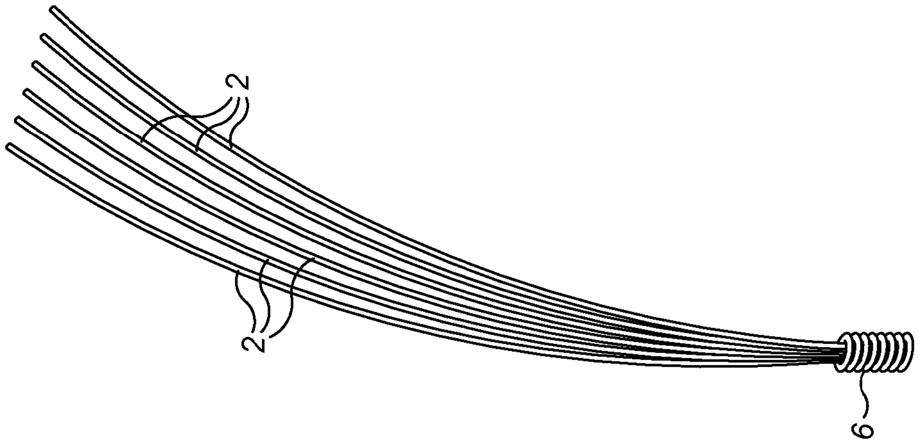

| | | | | |
|---|---|---|---|---|
| 6,221,655 | B1 * | 4/2001 | Fung | B01L 3/5021 435/7.1 |
| 7,037,275 | B1 * | 5/2006 | Marshall | A61B 10/02 600/562 |
| 2006/0254014 | A1 * | 11/2006 | Konishi | A46B 7/04 15/210.1 |
| 2010/0240965 | A1 * | 9/2010 | Furuta | A61K 31/4375 600/300 |
| 2012/0226189 | A1 * | 9/2012 | Fitzgerald | A61B 5/4233 600/562 |
| 2013/0196841 | A1 | 8/2013 | Dobrowolski | |
| 2013/0252796 | A1 | 9/2013 | Von Stetten et al. | |
| 2013/0303355 | A1 | 11/2013 | Daub et al. | |
| 2015/0057517 | A1 * | 2/2015 | Pease | A61B 10/02 600/350 |
| 2016/0045189 | A1 * | 2/2016 | Maguire | A61B 10/02 600/572 |
| 2016/0081672 | A1 | 3/2016 | Lubinski et al. | |
| 2016/0235391 | A1 * | 8/2016 | Gardner | A61B 10/0283 |
| 2018/0070928 | A1 * | 3/2018 | Jones | A61B 5/6861 |

FOREIGN PATENT DOCUMENTS

| | | | |
|---|---|---|---|
| WO | 2009/061819 | A1 | 5/2009 |
| WO | 2011/058316 | A1 | 5/2011 |
| WO | 2018/048754 | A1 | 3/2018 |

* cited by examiner

MEDICAL STRING KIT

CROSS-REFERENCE TO RELATED APPLICATIONS

This application is a National Stage of International patent application PCT/GB2019/053272, filed on Nov. 19, 2019, which claims priority to foreign Great Britain patent application No. 1818843.3, filed on Nov. 19, 2018, and foreign Great Britain patent application No. 1903657.3, filed Mar. 18, 2019, the disclosures of which are incorporated by reference in their entireties.

The use of a string that is swallowed by a patient has been used for many years to diagnose conditions such as giardia, cancer, pH related conditions such as acid reflux, etc. Typically, such a string comprises a gelatine capsule at one end thereof. The string is typically administered by a clinician or nurse. The problem with this type of string is that the gelatine capsule may stick to the oesophageal lining of the patient which may pose problems for patients, particularly if the patient has oesophageal pathology causing narrowing.

Once the string has been removed from the patient, there is a need for the string to be handled safely, without contamination. This can be difficult, since the string may be relatively long in length.

Eosinophilic esophagitis (EoE) is a disease of the immune system which is known to be increasing in incidence worldwide. The condition causes discomfort when swallowing (dysphagia) and can result in food getting stuck on swallowing (food impaction). The condition is due to the build up of white blood cells (eosinophils) in the oesophagus due to a reaction to foods and/or acid reflux which can inflame or injure oesophageal tissue. Food is a recognised cause for the inflammation, although the mechanism is not clear and available tests such as food allergy testing are often not helpful in deciding which food is the trigger. Typically, the condition has been diagnosed using an endoscope followed by a biopsy. Patient symptoms (e.g. degree and frequency of dysphagia) are not a good indicator of disease activity and the lining of the oesophagus can look normal endoscopically and diagnosis is only made following a biopsy. This poses problems with managing these patients, in particular when monitoring response to treatment. The use of a string with a gelatine capsule at the end to aid swallowing has been problematic with some patients due to oesophageal narrowing and difficulties swallowing the capsule. Eosinophils release various chemicals into the lining of the oesophagus which can adhere to the string. Some, by virtue of their chemical properties, adhere strongly and cannot be removed from the string to enable laboratory analysis. In addition, removing the swallowed string from a patient and placing into a container appropriate for laboratory analysis can pose a risk to the individual (likely to be a doctor or nurse) as it is long and cumbersome and covered with a biological fluid which may lead to a possible infection risk.

Due to some of these markers of eosinophilic inflammation (particularly ECP, eosinophilic cationic protein) being very adherent to the string, in order for these to be measured accurately, the ECP has to be released from the string by chemical processing. This is time consuming and involves manipulation of the string by a laboratory technician.

The present invention seeks to address the above problems.

According to a first aspect, there is provided apparatus comprising a string for insertion into the oesophagus of a patient, the string comprising a proximal end and a distal end, wherein the string forms a structure at the distal end thereof to assist in the insertion of the string into the patient.

Advantageously, the present invention provides apparatus comprising a string that may be easily swallowed by a patient. In addition, the present invention advantageously provides a string collection device that may be used to collect the string once swallowed and to place the string easily into a laboratory container, and apparatus that may be used in a method (e.g. using a centrifuge activated device) for washing (e.g. eluting) components stuck to the string for laboratory analysis. Advantageously, the apparatus of the present invention optimises function during insertion of the string into the oesophagus of a patient, and improves safety and practicality of the nurse or doctor handling the string. Typically, the addition of eluting and neutralising buffer to the string can be time consuming and requires laboratory staff and training. Advantageously, the use of a centrifuge activated device in accordance with the present invention to release the buffer while in the centrifuge eliminates the need for manually performing this step. Advantageously, the use of centrifugation also minimises staff exposure to biological substances such as oesophageal fluid. Preferably, the centrifuge activated device may be provided as one unit. In one embodiment, the centrifuge activated device may be provided as a sealed unit, to ensure that it is kept sterile.

Preferably, the structure provided at the distal end of the string comprises a helical component. In another embodiment, the string may form a compressed pellet of string at the distal end. In another embodiment, the string may be knotted at the distal end. Advantageously, the provision of a string having a structure at the distal end that is formed from the string itself avoids the problems associated with including a non-string component at the distal end (such as gelatine) which may become stuck or cause oesophageal irritation.

Advantageously, the provision of a string having a helical component at the distal end thereof provides a structure that is flexible and soft to assist in swallowing the string. Preferably, the size of the structure at the distal end of the string is optimised such that it is small enough that it does not cause irritation to the oesophagus, whilst still being capable of being swallowed by a patient. Preferably, the string is coiled such that it acts like a spring. Preferably, the size of the structure at the distal end of the string is equivalent to a size 5 capsule (typically 11.1 mm long and 4.9 mm wide) but can be of larger or smaller size if needed.

Preferably, the helical component at the distal end of the string is formed by soaking the distal end of the string in a solution that will confer rigidity on the string once dry, wrapping the distal end of the string around the outer surface of a rod and allowing the string to dry. In one embodiment, the string is wrapped around the outer surface of a metal rod. In one embodiment, the string may be soaked in a solution comprising a sugar. In another embodiment, the string may be soaked in a solution of corn starch, such as 1% corn starch solution. In another embodiment, the string may be steam heated to confer ability to retain a new shape. In one embodiment, the string may be dipped in water (preferably sterile water) and then wound around a metal rod and heated to a temperature of approximately 100° C. for approximately 10 minutes. In one embodiment, the rod may be an aluminium rod. Preferably, once the string has set, the distal end of the string is removed from the outer surface of the rod. Advantageously, the helical component at the distal end of the string provides a structure that is flexible and soft to assist in moving the string down the oesophagus during swallowing and preventing the string from getting stuck in areas of narrowing of the oesophagus if present. Advantageously, the string is of sufficient volume and is flexible enough to assist the patient in swallowing the string. Advantageously, the helical structure at the distal end of the string assists the patient in swallowing the string. Advantageously, when exposed to moisture, for example, in the stomach of a patient, the structure at the distal end of the string unwinds such that the distal end of the string adopts a substantially straight conformation, thus assisting in removal of the string from the patient.

In one embodiment, the structure at the distal end of the string may be coated with a flavouring. In one embodiment, the structure at the distal end of the string may be coated with at least one drop, preferably two to three drops, of flavouring essence, for example, a concentrated flavouring essence. Advantageously, coating the structure at the distal end of the string with a flavouring can encourage swallowing of the string by patients. This is particularly beneficial in children.

Preferably, the string further comprises a structure at the proximal end thereof. Preferably, the structure provided at the proximal end comprises a compressed or knotted portion of the string. Preferably, the structure provided at the proximal end of the string assists in attachment of the string to a cheek of the patient. Advantageously, the provision of a string having a structure at the proximal end thereof assists in attachment of the proximal end of the string to a patient such that the string is not inadvertently detached or swallowed by the patient during insertion of the string, thus improving safety and ease of use.

Preferably, the proximal end of the string is attached to a patient using an attachment means. Preferably, the attachment means comprises tape. Preferably, the tape comprises skin-adhesion grade tape to improve comfort for the patient. Advantageously, the use of tape to secure the string to the patient improves security and reduces the risk of unwanted detachment of the string from the patient. Advantageously, the use of skin-grade adhesion tape prevents or reduces the possibility of the string detaching from the tape, and thus from the patient. Advantageously, the use of skin-grade adhesion tape improves security and comfort for the patient. In one embodiment, the string attachment means may comprise an adhesive removable label to which details regarding the sample type, date sample taken, patient identifiers (such as name, age, date of birth, unique patient identifier such as NHS or hospital number) can be added. Advantageously, this improves sample identification and reduces the risk of sample error (such as sample mix up). In one embodiment, the label may be removed from the string and placed on the tube to which the string will be inserted post-use, prior to sending to the laboratory.

Preferably, the string comprises a medical grade string.

Preferably, the string may be coated with a biological macromolecule. Preferably, the string may be coated with a protein which may act as a marker for a condition. In one embodiment, the string may be coated with a protein such as eosinophilic cationic protein (ECP). In another embodiment, the string may be coated with a dye or other marker. Advantageously, the string acts to capture an element from the oesophagus of a patient that may be useful diagnostically following further analysis.

In another embodiment, the string may be coated with or encompass a pharmaceutical agent for administration to a patient. In this embodiment, the string may assist in the delivery of a drug to a patient. Advantageously, the use of the string to administer a drug assists the patient in swallowing tablets and/or medication and has limited local area of activity (where it lies against the lining of the oesophagus).

Preferably, the string may be used to absorb a component following insertion into the oesophagus of a patient. Preferably, the string is used to absorb and/or capture a component that will be useful diagnostically. Preferably, when the string has been inserted into the oesophagus of a patient, the string absorbs a protein such as eosinophilic cationic protein (ECP). ECP is known to be a marker for the condition eosinophilic esophagitis (EoE), such that the detection of this protein may indicate that the patient is suffering from this condition and the amount of protein detected may indicate how severe the inflammation is, thus providing an indicator of disease activity. Typically, levels of string ECP isolated from the oesophagus of patients with eosinophilic oesophagitis correlates with levels of eosinophils in biopsy specimens from these patients. Typically, a high string ECP level correlates with a high biopsy eosinophil count.

In another embodiment, the string may be used to measure IgG4 levels in a fluid that is absorbed by the string. Advantageously, the presence of IgG4 levels will help to distinguish the condition of reflux oesophagitis from eosinophilic oesophagitis, since IgG4 is only present in the latter condition. Advantageously, the presence of IgG4 antibodies can also be used to test for possible food triggers for eosinophilic oesophagitis (for example, to detect food specific IgG4 antibodies) to help guide a food elimination diet to treat this disease. Advantageously, if a specific IgG4 antibody is detected in relation to a specific food, then eliminating these foods would typically bring the disease into remission.

In one embodiment, the string may be used in a biopsy procedure, for example, to test the presence of one or more cancer cell in a patient. Advantageously, the string may be used to detect the presence of other biological samples in a patient.

Preferably, the string has a length to ensure that, when inserted into a patient, the string is in contact with the entire length of the oesophagus of the patient. Preferably, the string has a length to ensure that the structure at the distal end of the string enters the stomach of the patient. Advantageously, providing a string that has a length such that it is in contact with the entire length of the oesophagus assists in the adequate placing of the string within a patient, thus optimising the procedure.

In some embodiments, segments of the string may be analysed separately following removal of the string from the oesophagus of a patient. In one embodiment, the string may comprise an interval marker. In one embodiment, the interval marker may comprise an ink or dye. In another embodiment, the interval marker may comprise at least one knot provided on the string. Typically, following removal of the string from a patient, the string may be cut at the intervals shown by the interval markers and individual segments may be analysed separately.

Typically, the string may be analysed following insertion into a patient to determine whether the distal end of the string has entered the stomach of the patient. Typically, following removal of the string from a patient, the chemical composition of the distal end of the string may be analysed. In one embodiment, the pH of the distal end of the string may be analysed, for example using a pH indicator dye or paper. Typically, if the distal end of the string has been present in the stomach of the patient, the pH of the distal end of the string will be acidic, due to the acidic nature of the stomach. In another embodiment, following removal of the string from a patient, the distal end of the string may be analysed to test for other stomach markers such as pepsin/pepsinogen or gastrokines.

In one embodiment, the string may be coated with a substance that will provide a stimulus to the oesophageal lining of a patient. In one embodiment, the string may be coated with a substance that will provoke an inflammatory response by the oesophageal lining. Preferably, the substance that provides a stimulus will interact with other biological mediators that are released in response. Typically, the string may be coated with a biological substance, a chemical substance or a food. Typically, the substance may bind to the string and may be measured to determine the effect of the stimulus. In one embodiment, the string may be coated with a cytokine, a weak acid or alkaline substance or a food, such as a whole food or a food component. In one embodiment, the string may be coated with whole milk. In another embodiment, the string may be coated with ovalbumin. In the embodiment wherein the substance providing the stimulus is embedded within the string, the position of the substance on the string may be marked, for example, using a dye or ink or by knotting the string. In this embodiment, string segments on either side of the stimulus can be removed (e.g. cut out) and biological components of inflammation measured. In the embodiment wherein the provoking stimulus is applied to the string, the segment of the string coated with the stimulus may be covered with a protective film to protect the stimulus from being washed away during the swallowing process. Preferably, the protective film comprises a dissolvable substance such as gelatine, wherein the dissolvable substance will dissipate once in place to reveal and/or release the stimulus.

Preferably, following removal of the string from a patient, the string is analysed in a laboratory to check for any biological components that may have bound to the string when it was inserted in the patient.

In one embodiment, the apparatus may comprise a plurality of strings for insertion into the oesophagus of a patient. Preferably, the plurality of strings in combination form a single structure at the distal end thereof. Preferably, the apparatus comprises a plurality of separate strings which combine at the distal end of each string to form a single structure, to assist in insertion of the strings into a patient. Preferably, the structure provided at the distal end of the plurality of strings comprises a helical component. In another embodiment, the structure provided at the distal end of the plurality of strings comprises a compressed pellet. Typically, the swallowing of multiple strings by a patient is difficult. Advantageously, providing a plurality of strings having structure at the distal end thereof assists the patient in swallowing the strings. Preferably, the plurality of strings comprising a structure at the distal end thereof are swallowed by a patient simultaneously. Advantageously, the use of a plurality of strings assists in the detection of more than one component when the strings are subsequently analysed following removal from a patient. Advantageously, the use of a plurality of strings may assist in the detection of one or more chemical, protein or antibody component. This is particularly important since oesophageal diseases can be difficult to detect and may affect different regions of the oesophagus. In the embodiment wherein a single string is inserted into a patient, following removal of the string, the string is typically cut into segments and each segment is analysed in different tests. In this embodiment, it may be possible to miss an area of disease within the oesophagus of a patient, since the oesophageal diseases may be patchy and affect different areas of the oesophagus. Advantageously, the use of multiple strings means that each string contacts substantially the entire lining of the oesophagus and thus, each string may be separately analysed following removal from a patient, thus providing a more accurate result. Typically, the strings are analysed by removing (e.g. cutting) the distal structure from the end of the strings and then analysing each of the strings separately.

In one embodiment, the apparatus of the present invention may be used in human and/or veterinary medicine. Typically, humans and/or animals may chew the string to allow for collection of saliva for analysis using the apparatus of the invention. In another embodiment, the string may be used to collect and test the saliva of humans. Typically, in this embodiment, the saliva of humans may be collected and used to carry out antibody, DNA and/or RNA tests.

According to a second aspect, there is provided a kit for use with the string of the first aspect, the kit further comprising means for removing a sample from the string following insertion into a patient.

Preferably, the kit comprises a string capture rod, string collection apparatus, string extraction apparatus and/or a centrifuge tube.

Preferably, the string capture rod assists in transfer of the string following removal from the oesophagus of a patient to a container, for example, for further laboratory analysis. Advantageously, the use of a string capture rod to transfer the string minimises sample contamination and reduces user risk, i.e. providing for safe handling of the string.

Preferably, the string capture rod comprises a cylindrical element, wherein the string may be wound around the outer surface of the cylindrical element. In one embodiment, the cylindrical element may be telescopic. Advantageously, the use of a telescopic cylindrical element reduces the amount of space taken by the string capture rod, for example, during storage.

Typically, the string capture rod has a length that is between 5 cm and 25 cm, preferably between 10 cm and 20 cm, and most preferably around 16 cm in length.

Preferably, the outer surface of the string capture rod is substantially smooth and comprises a material such as Teflon or polypropylene.

Preferably, at least one end of the cylindrical element is rounded. Preferably, the at least one end of the cylindrical element that is rounded is used to capture the string. Advantageously, the rounded end of the cylindrical element prevents any unwanted tearing of the string during capture by the string capture element. Typically, the distal end of the string is provided with a roughened surface. Advantageously, the roughened surface at the distal end of the string will prevent unwanted release of the string from the capture rod due to the sticky nature of the string when wet.

In one embodiment, the string capture rod may be tapered along the length of the cylinder to assist in removal of the string therefrom.

Preferably, the string capture rod further comprises a guard element. Preferably, the guard element is provided at the end of the string capture rod that is held by a user. Preferably, the guard element comprises a cylindrical portion that is dimensioned such that it fits around the circumference of the cylindrical element. Preferably, the guard element further comprises a circular portion that is substantially perpendicular to the axis of the cylindrical portion of the guard portion and extends therefrom. Typically, the guard element may slide along the longitudinal axis of the cylindrical element of the string capture rod. Typically, the string is wound around the outer surface of the cylindrical element. Preferably, the user then slides the guard element along the longitudinal axis of the cylindrical element to push the string along the cylindrical element and into an appropriate container for transfer to the laboratory. Typically, the guard element may slide along the longitudinal length of the cylindrical element towards the rounded end of the cylindrical element. Advantageously, the guard element provides protection to the string as it prevents the user from coming into contact with the string, thus minimising contamination of the string and protects the user from the patient's oesophageal fluid.

Preferably, the string capture rod comprises a metallic material. In this embodiment, the string capture rod is reusable following sterilisation. In another embodiment, the string capture rod comprises a plastics material. In this embodiment, the string capture rod is disposable. It is preferred that the string capture rod is made from a material that is rigid enough to enable the string to be wound around the rod and smooth enough so as not to hinder the travel of the wound string along the cylinder length of the string capture rod.

In one embodiment, the string collection apparatus may comprise a string removal means. Typically, when the string is wet it adheres to the string capture rod. Advantageously, the string removal element assists in removal of the string from the string capture rod. Preferably, the string removal means may comprise a thimble-like element. Preferably, the string removal element is substantially cylindrical in shape. Preferably, the string removal element comprises a cylindrical wall extending from an upper surface at one end of the cylinder. Preferably, the end of the string removal means opposite to the upper surface is open. In another embodiment, the string removal means may comprise a disk. In one embodiment, the string removal means may comprise a disposable plastics element. Preferably, the string removal means may comprise one or more perforations. Preferably, the upper surface of the string removal means may comprise a hole, wherein the hole is dimensioned such that the string capture rod may pass therethrough. Preferably, the guard element comprises a recess which is shaped such that it may accommodate the string removal means.

Preferably, as the string capture rod passes through the hole in the string removal means, the string is adapted to be removed from the string capture rod. Preferably, the string capture rod is adapted to be inserted through the cylindrical portion of the guard element. Preferably, the string capture rod is adapted to pass through the hole provided in the upper surface of the string removal means. Preferably, the string capture rod is adapted to be withdrawn into the guard element and then to push forwards such that the string removal means is placed into the string holding cup. Preferably, the string removal means is adapted to be held within the string holding cup. Preferably, the string capture rod is removed from the string removal means. Typically, the perforations in the string removal means allow buffer to pass through the string removal means and onto the string.

Preferably, the string collection apparatus comprises a string holding cup. Preferably, the string holding cup holds the string after removal from the oesophagus of a patient. Preferably, the string collection apparatus further comprises a fluid collection tube for holding the string holding cup. Preferably, the string holding cup comprises a cylindrical wall extending from and surrounding a base. Preferably, the base of the string holding cup comprises at least one hole. Preferably, the at least one hole has a diameter which allows the passage of oesophageal secretions through the string holding cup during centrifugation.

Preferably, the at least one hole has a diameter of approximately 0.1 mm. Preferably, the base of the string holding cup has a diameter of approximately 14 mm. Preferably, the end of the string holding cup that is opposite to the base is open. Preferably, the string holding cup is of sufficient diameter to fit the string capture rod. Preferably, the string holding cup is of sufficient diameter to fit the rounded tip of the string capture rod. Preferably, the user may transfer the string from the patient to the string holding cup via the string capture rod.

Preferably, the string holding cup fits within a fluid collection tube. Preferably, the fluid collection tube may hold a volume of approximately 15 ml. Preferably, the open end of the string holding cup fits within the fluid collection tube. Preferably, the fluid collection tube is cylindrical and has a base at one end. Preferably, the string holding cup and/or the fluid collection tube comprise a plastics material. Preferably, the string holding cup and/or fluid collection tube may hold a volume of approximately 2 ml.

In one embodiment, the string holding cup may hold a volume of approximately 3 ml. In one embodiment, approximately 300 μl extraction buffer is added to the string holding cup comprising the sample. Typically, a smaller or larger volume of extraction buffer may be added to the string holding cup comprising the sample. Preferably, the string holding cup may be removed from the fluid collection tube to access fluid for laboratory analysis.

Preferably, the string holding cup and the fluid collection tube are placed within a centrifuge tube. Preferably, the centrifuge tube is a 15 ml centrifuge tube. Preferably, the adhesive patient identifier can be removed from the string and placed on the outer surface of the centrifuge tube. Preferably, during centrifugation, the perforations in the string holding cup allow fluid released from the string to be collected at the bottom of the fluid collection tube. Preferably, following centrifugation the string holding cup can be removed from the fluid collection tube and the fluid can be analysed in a laboratory.

Preferably, the inner surface of the fluid collection tube is tapered such that the diameter at a substantially central portion along the longitudinal length of the tube is less than the diameter at the end of the tube. In one embodiment, the inner surface of the fluid collection tube has an indentation at a substantially central portion along the longitudinal length of the tube. In one embodiment, the fluid collection tube has a diameter of approximately 14 mm at the base and a diameter of approximately 19 mm at the opening. Preferably, the fluid collection tube tapers along the length thereof to allow the string holding cup to sit within the fluid collection tube such that it is held in place. Typically, the fluid collection tube may be approximately 40 mm in length. Advantageously, the reduced diameter along the longitudinal length of the inner surface of the fluid collection tube assists in holding the string holding cup in place, allowing the string holding cup to be removed by a user when required, but preventing the string holding cup from slipping further down the length of the fluid collection tube when centrifuged.

Preferably, the string extraction apparatus comprises a cap comprising a retaining ring which is adapted to engage with a container comprising an extraction buffer. Preferably, the string extraction apparatus further comprises a piercing device. Preferably, the string extraction apparatus engages with the string collection apparatus during centrifugation. Preferably, the piercing device sits adjacent to the string holding cup during centrifugation.

Preferably, the piercing device comprises a spike. It is preferred that the piercing device further comprises a disk portion, wherein the spike is positioned at a position substantially at the centre of the disk portion. Preferably, the spike extends from a substantially central portion of the disk portion. Preferably, the disk portion of the piercing device comprises a plastics or metallic material. Preferably, the spike of the piercing device comprises a plastic or metallic material. Preferably, the piercing device comprises at least one hole or perforation. Preferably, the retaining ring sits between the container comprising the extraction buffer and the piercing device and is adapted to prevent contact of the spike of the piercing device with the container comprising the extraction device prior to centrifugation. Preferably, the retaining ring prevents contact of the spike of the piercing device with the container comprising the extraction buffer prior to activation by centrifugation. Advantageously, the retaining ring prevents the container holding the buffer from being punctured prematurely. Preferably, the spike of the piercing device is adapted to puncture the container comprising the extraction buffer during centrifugation. Typically, the g forces of centrifugation push the container comprising the extraction buffer past the retaining ring and onto the piercing device such that the extraction buffer is released. Advantageously, the at least one hole or perforation provided within the piercing device distributes the buffer evenly over the string which is held within the string holding cup.

In one embodiment, the piercing device may comprise an L-shaped piercing device. Preferably, the L-shaped piercing device creates a triangular valve in the cap or stopper of the container comprising the extraction buffer when pierced. Typically, the valve opens under the centrifuge g forces of centrifugation to release the liquid. In one embodiment, the L-shaped piercing device may be provided on a base comprising a plurality of perforations as a support. Typically, the tip of the piercing device may pierce the rubber seal of the container comprising the buffer. Advantageously, a valve is created as the tip pierces the seal of the container which allows the liquid buffer to pass onto the perforated base. Typically, the liquid is then distributed through the perforations and onto the string within the container. Typically, a rubber stopper has self sealing properties such that when the stopper is punctured by a needle, the stopper will seal around the needle which may make it difficult for buffer to be released from the container. Advantageously, the valves created by the unique shape of the piercing device as it cuts through the rubber stopper will address this problem and allows release of buffer from the container.

In another embodiment, the piercing device may comprise a star shaped pyramid piercing device. Advantageously, the use of a piercing device having this shape creates a number of triangular valves in the seal when pierced. The valves open under the centrifuge g forces to release the liquid from the container containing the buffer. The shape of the piercing device may be modified further to contain channels which also aids the flow of buffer along the piercing device and onto the string below. In one embodiment, the piercing device pierces the cap or stopper of the container comprising the extraction buffer and creates four valves. In one embodiment, the cap or stopper comprises a rubber material.

In another embodiment, the kit further comprises a lid which may be placed over and/or may be used to seal the fluid collection tube and/or string holding cup. In one embodiment, the lid may comprise an extraction buffer. In one embodiment, the lid may comprise a release mechanism, wherein when the lid is placed on the fluid collection tube and/or string holding cup, the lid is punctured such that extraction buffer is released into the string holding cup. Typically, when the lid is placed onto the string holding cup and/or fluid collection tube, a puncture device is activated to puncture the lid comprising the extraction buffer. In one embodiment, the puncture device may be provided within the lid. In another embodiment, the puncture device may be provided adjacent to the lid. In one embodiment, the puncture device may comprise a spike. In another embodiment, the extraction buffer may be provided in a container which may be punctured when the lid is placed onto the fluid collection tube and/or string holding cup. In one embodiment, the puncture device may be a piercing device.

In one embodiment, the kit may further comprise a bottle. Typically, the bottle is a buffer holding container or buffer holder. Preferably, the bottle is standardised for use with a centrifuge activated device. Typically, the bottle comprises a buffer. Preferably, the bottle comprises a stopper and/or a cap. It is preferred that the stopper is held in place by the cap. Preferably, the stopper comprises a rubber material. Preferably, the cap is a metallic crimp cap, preferably an aluminium or silver crimp cap. Advantageously, the combination of the stopper and cap provides a liquid tight seal. Preferably, the bottle is used in combination with the string collection apparatus. Preferably, the bottle is dimensioned such that it may be used in combination with the fluid collection tube and/or string holding cup. Preferably, the bottle fits within the lid of the kit. In this embodiment, it is preferred that the piercing device comprises a needle like device. Preferably, the needle like device is sharp to allow the stopper and seal to be punctured. Preferably, the needle like device is hollow to allow the liquid under the g forces of centrifugation to flow through the needle and onto the string that is held within the string holding cup. Preferably, the piercing device comprises an L-shaped piercing device or a star shaped piercing device as described above. Preferably, a disk is provided within the bottle and substantially parallel to the plane of the base of the bottle. Preferably, the disk comprises a plurality of holes, such that as the liquid passes through the needle, the liquid is distributed evenly onto the string.

In one embodiment, the release mechanism comprises a latch member. In this embodiment, the latch holds the buffer in place within the lid when the lid is not attached to the string holding cup and/or fluid collection tube. In this embodiment, the latch member may be released when the cap is placed onto the string holding cup and/or fluid collection tube. Typically, the release of the latch mechanism may result in puncture of the lid and/or container comprising the extraction buffer such that the buffer passes over the string that is held within the string holding cup. In another embodiment, when the lid comprising the extraction buffer is placed onto the fluid collection tube and/or string holding cup, a spike held within or adjacent to the lid and/or fluid collection container punctures the lid and causes release of the extraction buffer. In one embodiment, the spike may be held within the lid and the action of placing the lid onto the fluid collection tube and/or string holding cup causes the spike to puncture the portion of the lid holding the extraction buffer, thus causing release of the extraction buffer.

In one embodiment, the retaining ring and release member may be used together to prevent unwanted puncture of the container comprising the extraction buffer. In one embodiment, the retaining ring comprises a first safety device to prevent unwanted release of the extraction buffer from the container comprising the extraction buffer. In one embodiment, the release member comprises a second safety device to prevent unwanted release of the extraction buffer.

Typically, the first safety device may be disarmed during centrifugation when the container comprising the extraction buffer moves past the retaining ring and onto the piercing device such that the extraction buffer is released. Typically, the second safety device may be disarmed by putting the lid onto the fluid collection tube and/or string holding cup, causing the lid to puncture and releasing the extraction buffer held within the lid. In one embodiment, release of the latch member may cause the lid to puncture and cause release of extraction buffer from the lid. In one embodiment, the first and/or second safety device may be disarmed to cause release of the extraction buffer from the container comprising the extraction buffer and/or lid comprising the extraction buffer during centrifugation. Typically, once the extraction buffer has been removed from the lid and/or container comprising the extraction buffer, the extraction buffer passes into the string holding cup where it passes over the string, through the at least one hole provided in the string holding cup and into the fluid collection tube.

In one embodiment, a spring is provided around the piercing unit. Advantageously, the provision of a spring assists in preventing the buffer holder from being pierced prematurely. Typically, the provision of a spring will separate the buffer holder from the piercing unit in transit. Typically, during centrifugation, the spring will be compressed by the buffer holder under g forces which will allow the piercing unit to come into contact with the buffer holder, resulting in the piercing of the buffer holder and subsequent release of buffer.

In another embodiment, a clip may be provided around the piercing unit. Advantageously, the provision of a clip assists in preventing the buffer holder from being pierced prematurely. Typically, the provision of a clip will separate the buffer holder from the piercing unit in transit. Typically, during centrifugation, the clip will move into the buffer holder under g forces which will allow the piercing unit to come into contact with the buffer holder, resulting in the piercing of the buffer holder and subsequent release of buffer. Typically, the clip comprises a plastics material. In one embodiment, the clip may be spring loaded.

In some embodiments, a component within the oesophageal fluid may stick to the string and may require removal from the string using an extraction and/or release buffer. In one embodiment, the extraction or release buffer can be added to the string prior to centrifugation. In another embodiment, the extraction or release buffer can be added to the string during centrifugation, i.e. during a centrifuge activated mechanism, wherein the extraction buffer is released onto the string by g forces acting on the tube during centrifugation. In one embodiment, the extraction or release buffer may require neutralisation which can be achieved by providing a neutralisation buffer within the fluid collection tube. Preferably, centrifugation is used to obtain an oesophageal sample for laboratory analysis. In one embodiment, the pH of the sample may be measured following centrifugation. Preferably, ECP that is collected by the oesophageal string test adheres to the string and centrifugation alone is typically not sufficient to remove it from the string. Typically, the addition of a low pH buffer to the string allows release of the ECP.

In one embodiment, the kit may comprise a string holder. Preferably, the string holder comprises a disc region comprising a front conical projection onto which the string is wound and a rear cylinder where the remaining string is wrapped. Typically, the disc region comprises a flexible material. Advantageously, the string holder may be used to preserve the shape and integrity of the coil provided at the proximal end of the string. Typically, the string is coiled around the string holder and then placed in a sealed package until ready for use. Advantageously, the provision of a sealed package allows the string to be kept sterile. Typically, once removed from the packaging the string may be unwound from the rear cylinder and the distal end of the string is fixed to the check of a patient as described above. Preferably, the string which is wound around the front conical projection remains in place until the patient is ready to swallow the string. Typically, at this point, gentle squeezing of the outer edge of the string holder compresses the conical holder, thus reducing the diameter of the holder and allowing the string to be removed therefrom. Typically, the string holder comprises a plurality of segments, assisting in the compression of the string holder to facilitate removal of the string therefrom. Typically, the released coil of string can then be placed in the mouth of the patient and swallowed. Typically, following use, the string holder may be discarded. Typically, the string holder comprises a plastics material. Typically, the plastics material is smooth, stiff and flexible. In one embodiment, the string holder may be packed in packaging that also includes a centrifuge activated device. In one embodiment, the string holder and/or centrifuge activated device may be packaged in a packaging that also includes a set of instructions for how to use the string holder and/or centrifuge activated device.

In one embodiment, the string holder may also comprise a string capture rod. Advantageously, combining the string transport device and string collection device allow for the provision of a dual purpose unit. In this embodiment, the string can be captured and then stored using one unit. This embodiment can be used to store and transport the string but can also be used to collect the string once used and dispense into the tube with the centrifuge activated device.

In another embodiment, a DNA and/or RNA stabilising buffer may be used to reduce and/or prevent degradation of the sample prior to analysis. In one embodiment, the DNA and/or RNA stabilising buffer may comprise a TE buffer comprising 10 mM Tris (pH 8.0) with HCl and 1 mM EDTA. Advantageously, the addition of DNA and/or RNA stabilising agents to a sample may prevent contaminants in the saliva of a patient from breaking down nucleotides. In addition, the use of DNA and/or RNA stabilising agents in a buffer can help to stabilise a sample until it can be processed.

In a further embodiment, protein stabilising agents may be added to the buffer, such as protease inhibitors and/or metal chelators. Advantageously, the use of a protein stabilising agent may prevent degradation prior to analysis, and/or may assist in stabilising a sample where specific protein analysis may be needed.

In another embodiment, enzymes may be added to a buffer to remove free DNA and/or RNA that may act as a contaminant.

Typically, ECP that is collected by the oesophageal string test adheres to the string and centrifugation alone is not sufficient to remove it from the string. Typically, the addition of a low pH buffer to the string allows the release of ECP.

Preferably, the use of a DNA and/or RNA stabilising buffer and/or protein stabilising agent may assist in stabilising the sample prior to testing in a laboratory.

Advantageously, the use of a DNA and/or RNA stabilising buffer and/or protein stabilising agent may assist in stabilising a saliva sample prior to testing in a laboratory, thus improving the performance of the test.

Typically, the string may be analysed following insertion into a patient to determine whether the distal end of the string has entered the stomach of the patient. Typically, following removal of the string from a patient, the chemical composition of the distal end of the string is analysed. In one embodiment, the pH of the distal end of the string may be analysed, for example using a pH indicator dye or paper. Typically, if the distal end of the string has been present in the stomach of the patient, the pH of the distal end of the string will be acidic, due to the acidic nature of the stomach. In another embodiment, following removal of the string from a patient, the distal end of the string may be analysed to test for other stomach markers such as pepsin or gastrokines. It is preferred that the pH indicator and/or stomach markers are provided with the kit of the invention.

Advantageously, the kit of the present invention assists in obtaining a sample from a swallowed string and/or packaging the string for laboratory analysis.

Preferably, the kit comprises a centrifuge activated device (which may also be known as a CAD). Preferably, the centrifuge activated device comprises a buffer holder, a piercing device and a mechanism to prevent the buffer holder from being pierced prior to centrifugation. In one embodiment, the buffer holder may be a bottle. Preferably, the centrifuge activated device may be used in a method (e.g. using a centrifuge activated device) for washing (e.g. eluting) components stuck to the string for laboratory analysis. Advantageously, the apparatus of the present invention optimises function during insertion of the string into the oesophagus of a patient, and improves safety and practicality of the nurse or doctor handling the string. Typically, the addition of eluting and neutralising buffer to the string can be time consuming and requires laboratory staff and training. Advantageously, the use of a centrifuge activated device in accordance with the present invention to release the buffer while in the centrifuge eliminates the need for manually performing this step. Advantageously, the use of centrifugation also minimises staff exposure to biological substances such as oesophageal fluid.

Preferably, the mechanism to prevent the buffer holder from being pierced prior to centrifugation comprises a spring or retaining clip.

Preferably, the centrifuge activated device may be provided as one unit. In one embodiment, the centrifuge activated device may be provided as a sealed unit, to ensure that it is kept sterile.

Preferably, the centrifuge activated device is activated by centrifugation where the g forces cause piercing of the buffer holder and releasing the buffer.

According to a third aspect, there is provided a method of providing a structure at the distal end of the string of the apparatus of the first aspect of the invention, comprising the step of modifying the string to form a structure at the distal end of the string. Preferably, the string is modified to form a helical structure at the distal end. Preferably, the method comprises the steps of coating the distal end of the string in a solution which will confer rigidity to the string when dry, wrapping the distal end of the string around a rod to form a helical structure and allowing the string to dry. In one embodiment, the string may be soaked in a solution comprising a sugar. In another embodiment, the string may be soaked in a solution of corn starch, for example, 1% corn starch solution. Preferably, the string is steam heated to confer the ability to retain a new shape to the distal end of the string. In one embodiment, the string may be dipped in water (preferably sterile water), wound around the outer surface of a metal rod and heated to a temperature of approximately 100° C. for approximately 10 minutes. Preferably, once the string has set, the distal end of the string is removed from the outer surface of the rod. Advantageously, the helical component at the distal end of the string provides a structure that is flexible and soft to assist in insertion into the oesophagus of a patient, yet rigid to assist in the patient swallowing the string. Preferably, the size of the structure at the distal end of the string is optimised such that it is small enough that it does not cause irritation to the oesophagus, whilst still being capable of being swallowed by a patient. Preferably, size of the structure at the distal end of the string is equivalent to a size 5 capsule, for example, having a length of approximately 11.1 mm and a width of approximately 4.9 mm. In other embodiments, a smaller or larger size of structure at the distal end of the string can be used if needed.

According to a fourth aspect, there is provided a method of determining the presence of a substance within the oesophageal lining a patient using the apparatus of the first aspect, the method comprising the steps of providing a structure at the distal end of the string to assist the patient in swallowing the string, removing the string from the oesophagus of the patient and testing the string to check for the presence of the substance. In one embodiment, the method comprises the step of applying a marker such as a protein or dye to the string prior to insertion into the patient. Preferably, the string may be coated with a biological macromolecule. Preferably, the string may be coated with a protein which may act as a marker for a condition. In one embodiment, the string may be coated with the protein eosinophilic cationic protein (ECP). In another embodiment, the string may be coated with a dye or other marker. In one embodiment, the marker may be applied to the string during centrifugation.

Preferably, method comprises the step of absorbing a component from the oesophageal lining following insertion into the oesophagus of a patient. Preferably, when the string has been inserted into the oesophagus of a patient, the string absorbs a protein such as eosinophilic cationic protein (ECP). ECP is known to be a marker for the condition eosinophilic esophagitis (EoE), such that the detection of this protein may indicate that the patient is suffering from this condition. Typically, ECP can be released from the string using a low pH buffer. Typically, the ECP can be released from the string using a buffer comprising approximately 0.1 Molar glycine at approximately pH 2.8. Typically, this buffer can then be neutralised using an approximately 1 Molar Tris buffer at around pH 14. Typically, approximately 300 μl buffer, preferably comprising glycine, is used to elute the ECP protein into approximately 80 μl Tris buffer.

In one embodiment, segments of the string may be analysed separately following removal of the string from the oesophagus of a patient. In one embodiment, the method may comprise the step of providing an interval marker on the string. In one embodiment, the interval marker may comprise an ink or dye. In another embodiment, the interval marker may comprise at least one physical marker such as a knot provided on the string. Typically, following removal of the string from a patient, the string may be cut at the intervals shown by the interval markers and individual segments may be analysed separately. Typically, the segments may be measured to analyse variance in pH and/or differences in chemical and/or biological marker levels along the length of the string.

In one embodiment, the method comprises the step of coating the string with a substance that will provide a stimulus to the oesophageal lining of the patient. In one embodiment, the string may be coated with a substance that will provoke an inflammatory response by the oesophageal lining of the patient. Preferably, the substance that provides a stimulus will interact with other biological mediators that are released in response. Typically, the method comprises the step of coating the string with a biological substance, a chemical substance or a food. In one embodiment, the method comprises the step of coating the string with a cytokine, a weak acid or alkaline substance or a food, such as a whole food or a food component. In one embodiment, the method comprises the step of coating the string with whole milk. In another embodiment, the method comprises the step of coating the string with ovalbumin. In one embodiment, the method comprises the step of marking the string using a dye or providing a knot within the string to act as a marker. In this embodiment, string segments on either side of the stimulus can be removed (e.g. cut out) and biological components of inflammation measured. In the embodiment wherein the provoking stimulus is applied to the string, the method comprises the step of coating the section of the string provided with the stimulus with a protective film to protect the stimulus from being washed away during the swallowing process. Preferably, the protective film comprises a dissolvable substance such as gelatine, wherein the dissolvable substance will dissipate once in place to reveal the stimulus.

Preferably, the method comprises the step of analysing the string following removal from the oesophagus of the patient to check for any biological components that may have bound to the string when it was inserted in the patient.

Typically, the method comprises the step of using a string capture rod to transfer the string following removal from a patient to a string collection apparatus. Advantageously, the use of a string transfer rod to transfer the string minimises sample contamination and reduces user risk. Preferably, the string is wound around the outer surface of the cylindrical element of the string capture rod. Preferably, the user then slides the guard element of the string capture rod along the longitudinal axis of the string capture rod such that the string is pushed along the cylindrical element and into an appropriate container, e.g. for transfer to the laboratory.

Preferably, the string is transferred from the string capture rod to a string collection apparatus comprising a string holding cup. Preferably, the string holding cup holds the string after removal from the oesophagus of a patient. Preferably, the user transfers the string from the patient to the string holding cup via the string capture rod.

Preferably, the method further comprises the step of providing a string removal means, such as a thimble like element, to assist in removal of the string from the string capture element. Preferably, as the string capture rod passes through the hole in the string removal means, the string is removed from the surface of the string capture rod. Preferably, the string capture rod is inserted through the cylindrical portion of the guard element. Preferably, the string capture rod is passed through the hole provided in the upper surface of the string removal means. Preferably, the string removal means is housed within the recess of the guard element. Preferably, the string capture rod is withdrawn into the guard element and then pushed forwards such that the string removal means is placed into the string holding cup. Preferably, the string removal means is held within the string holding cup and the string capture rod is removed from the string removal means. Typically, the perforations in the string removal means allow buffer to pass through the perforations in the string removal means and onto the string.

In one embodiment, the method comprises the use of a string holder comprising a disc region comprising a front conical projection onto which the string is wound and a rear cylinder where the remaining string is wrapped. Typically, the disc region comprises a flexible material. Advantageously, the string holder may be used to preserve the shape and integrity of the coil provided at the proximal end of the string. Typically, the string is coiled around the string holder and then placed in a sealed package until ready for use. Advantageously, the provision of a sealed package allows the string to be kept sterile. Typically, once removed from the packaging the string is unwound from the rear cylinder and the distal end of the string is fixed to the check of a patient as described above. Preferably, the string which is wound around the front conical projection remains in place until the patient is ready to swallow the string. Typically, at this point, gentle squeezing of the outer edge of the string holder compresses the conical holder, thus reducing the diameter of the holder and allowing the string to be removed therefrom. Typically, the released coil of string can then be placed in the mouth of the patient and swallowed. Typically, following use, the string holder may be discarded. Typically, the string holder comprises a plastics material. Typically, the plastics material is smooth, stiff and flexible. In one embodiment, a robot may be used to wrap the string around the string holder and seal the string holder in a package.

In one embodiment, the string holder may also comprise a string capture rod. Advantageously, combining the string transport device and string collection device allow for the provision of a dual purpose unit. In this embodiment, the string can be captured and then stored using one unit. This embodiment can be used to store and transport the string but can also be used to collect the string once used and dispense into the tube with the centrifuge activated device.

Preferably, the method further comprises the step of providing a fluid collection tube which is dimensioned to hold the string holding cup.

Preferably, the method further comprises the step of providing a string extraction apparatus to assist in extracting the marker from the string. Preferably, the method comprises the step of providing a cap comprising a retaining ring, wherein the retaining ring engages with a container comprising an extraction buffer. Preferably, the string extraction apparatus engages with the string collection apparatus during centrifugation. Preferably, prior to centrifugation, the string is placed within the string holding cup of the string collection apparatus and the string collection apparatus and string extraction apparatus are placed within a centrifuge tube.

Preferably, the spike of the piercing device punctures the container comprising the extraction buffer during centrifugation. Typically, the extraction buffer is then transferred into the string holding cup, washes over the string and passes through the at least one hole provided within the base of the string holding cup. Typically, as the extraction buffer washes over the string it causes a component such as a protein that has bound to the string to be removed. Preferably, the component passes into the fluid collection tube where it can then be taken for further tests in the laboratory.

In one embodiment, the lid may comprise an extraction buffer. In this embodiment, when the lid is placed over the string holding cup and/or fluid collection tube, a release mechanism provided within or adjacent to the lid causes the lid to be punctured, thus removing the extraction buffer from the lid such that it passes over the string within the string holding cup and into the fluid collection tube.

In one embodiment, the lid may comprise a bottle, wherein the bottle may be standardised for use in a centrifuge. Preferably, the bottle may be used in combination with a string holding cup. Preferably, the bottle comprises an extraction buffer. Preferably, the bottle further comprises a stopper and seal. Preferably, the stopper is pierced with a piercing device to release buffer from the buffer and into the string holding cup, wherein the string is held within the string holding cup.

Preferably, the string holding cup and the fluid collection tube are placed within a centrifuge tube. Preferably, the centrifuge tube is a 15 ml centrifuge tube. Preferably, the adhesive patient identifier can be removed from the proximal end of the string and placed on the outer surface of the centrifuge tube. Preferably, during centrifugation, the perforations in the string collection cup allow fluid released from the string to be collected at the bottom of the fluid collection tube. Preferably, following centrifugation the string collection cup can be removed from the fluid collection tube and the fluid can be analysed in a laboratory.

According to a fifth aspect, there is provided a method of administering a drug to a patient using apparatus comprising a string in accordance with the first aspect. Preferably, the method comprises the step of applying a pharmaceutical substance to the distal end of the string which has been adapted to assist the patient in swallowing the string. In another embodiment, the method comprises the step of placing a pharmaceutical substance within the interior of the portion at the distal end of the string which has been adapted to assist the patient in swallowing the string. Advantageously, the method of administering a drug to a patient helps the patient in swallowing tablets and/or medication.

According to a sixth aspect, there is provided a method of removing a substance from apparatus comprising a string according to the first aspect of the invention using the process of centrifugation. Advantageously, the use of a centrifuge activated device aims to improve the consistency of removal of substances that are adhered to the string and to save laboratory staff time, minimise exposure to biological substances and simplify the process. Typically, the addition of eluting and neutralising buffer to the string can be time consuming and requires laboratory staff and training. Advantageously, the use of a centrifuge activated device to release the buffer while in the centrifuge eliminates the need for manually performing this step. Advantageously, the use of centrifugation also minimises staff exposure to biological substances such as oesophageal fluid.

Preferably, the method comprises the step of placing a string after removal from the oesophagus of a patient into a string collection apparatus according to the second aspect of the invention, placing the string collection apparatus and a string extraction apparatus according to the second aspect of the invention into a centrifuge tube and using the process of centrifugation to release extraction (i.e. elution) buffer onto the string. Preferably, during centrifugation, the piercing structure of the piercing device pierces the container comprising the extraction buffer such that the extraction buffer washes over the string and causes elution of a substance that is bound to the string. In one embodiment, a neutralisation buffer may be provided within the fluid collection tube to neutralise the extraction buffer. Preferably, following elution, the substance that was bound to the string is collected for testing in a laboratory.

Preferably, the act of centrifugation forces the spike to puncture the container comprising the extraction buffer and to release the extraction buffer onto the string.

Preferably, the forces applied to the system during centrifugation force the container holding the extraction buffer past the retaining ring onto the spike of the piercing device. Typically, the buffer is released and passes through at least one hole provided within the piercing device and onto the string that is held within the string holding container.

In one embodiment, the lid of the string holding cup comprises an extraction buffer release mechanism. In this embodiment, when the lid is positioned over the string holding cup and/or fluid collection tube, a release mechanism provided within or adjacent to the lid causes the lid to be punctured, thus removing the extraction buffer from the lid such that it passes over the string and into the fluid collection tube.

In one embodiment, the release mechanism and retaining ring or spring may provide first and second safety devices to prevent unwanted release of the extraction buffer. Typically, the lid is placed onto the fluid collection tube and/or string holding cup to activate the release mechanism such that the lid is punctured and extraction buffer is released. Typically, during centrifugation, the g forces of centrifugation force the buffer holding container past the retaining ring and onto the spike provided on the piercing device. Typically, the extraction buffer is released and passes through perforations of the piercing device and onto the string that is held within the string holding cup. Typically, the retaining ring and/or spring may be used to prevent piercing of the buffer holder or bottle during storage and/or transit.

In another embodiment, the extraction buffer may be held within a container comprising a valve that is normally in the closed position. In this embodiment, the force applied to the system during centrifugation causes the valve to open, thus releasing the extraction buffer from the container and onto the string.

In another embodiment, the piercing device sits within the container holding the extraction buffer and is activated by the g forces that are applied to the system during centrifugation.

According to a seventh aspect, there is provided a string holder for use with the string of the first aspect and/or the kit of the second aspect. Preferably, the string holder comprises a disc region comprising a front conical projection onto which the string is wound and a rear cylinder where the remaining string is wrapped. Typically, the disc region comprises a flexible material. Advantageously, the string holder may be used to preserve the shape and integrity of the coil provided at the proximal end of the string. Typically, the string is coiled around the string holder and then placed in a sealed package until ready for use. Advantageously, the provision of a sealed package allows the string to be kept sterile. Typically, once removed from the packaging the string is unwound from the rear cylinder and the distal end of the string is fixed to the check of a patient as described above. Preferably, the string which is wound around the front conical projection remains in place until the patient is ready to swallow the string. Typically, at this point, gentle squeezing of the outer edge of the string holder compresses the conical holder, thus reducing the diameter of the holder and allowing the string to be removed therefrom. Typically, the string holder comprises a plurality of segments, assisting in the compression of the string holder to facilitate removal of the string therefrom. Typically, the released coil of string can then be placed in the mouth of the patient and swallowed. Typically, following use, the string holder may be discarded. Typically, the string holder comprises a plastics material. Typically, the plastics material is smooth, stiff and flexible.

In one embodiment, the string holder may also comprise a string capture rod. Advantageously, combining the string transport device and string collection device allow for the provision of a dual purpose unit. In this embodiment, the string can be captured and then stored using one unit. This embodiment can be used to store and transport the string but can also be used to collect the string once used and dispense into the tube with the centrifuge activated device.

According to an eight aspect, there is provided a centrifuge activated device (CAD). Preferably, the centrifuge activated device comprises a buffer holder, a piercing device and a mechanism to prevent the buffer holder from being pierced prior to centrifugation. In one embodiment, the buffer holder is a bottle. Preferably, the centrifuge activated device may be used in a method (e.g. using a centrifuge activated device) for washing (e.g. eluting) components stuck to the string for laboratory analysis. Advantageously, the apparatus of the present invention optimises function during insertion of the string into the oesophagus of a patient, and improves safety and practicality of the nurse or doctor handling the string. Typically, the addition of eluting and neutralising buffer to the string can be time consuming and requires laboratory staff and training. Advantageously, the use of a centrifuge activated device in accordance with the present invention to release the buffer while in the centrifuge eliminates the need for manually performing this step. Advantageously, the use of centrifugation also minimises staff exposure to biological substances such as oesophageal fluid.

Preferably, the mechanism to prevent the buffer holder from being pierced prior to centrifugation comprises a spring or retaining clip.

Preferably, the centrifuge activated device may be provided as one unit. In one embodiment, the centrifuge activated device may be provided as a sealed unit, to ensure that it is kept sterile.

Preferably, the centrifuge activated device is activated by centrifugation where the g forces cause piercing of the buffer holder and releasing the buffer.

Figure 1A:
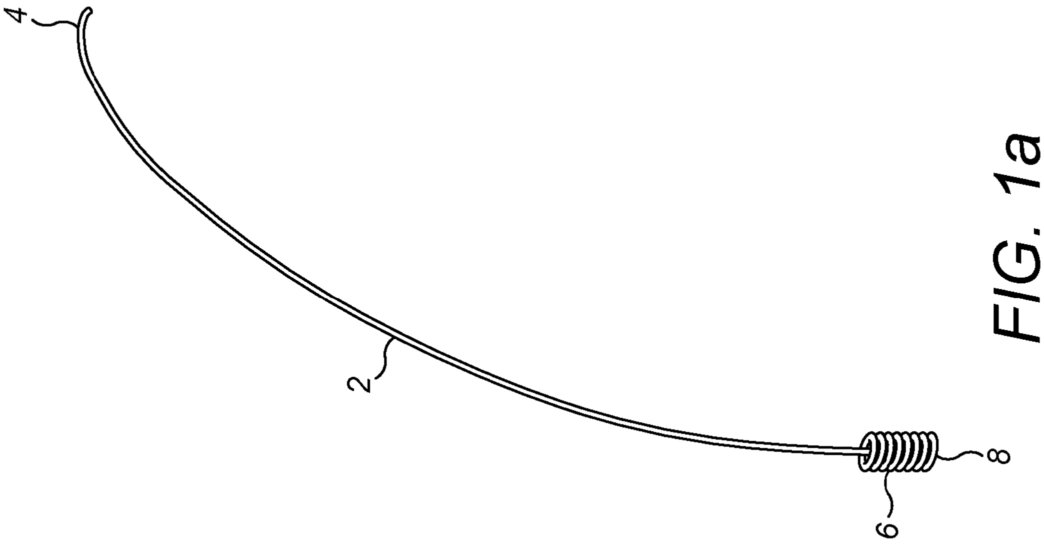
Figure 2A:
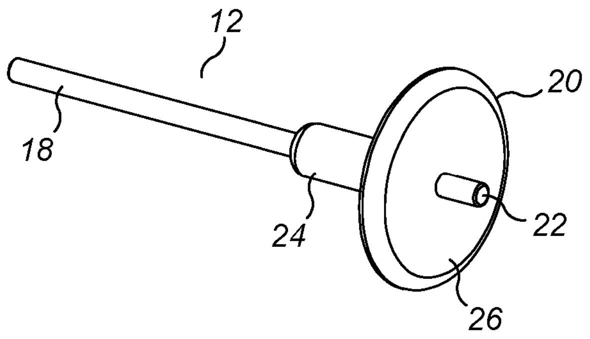
Figure 2B:
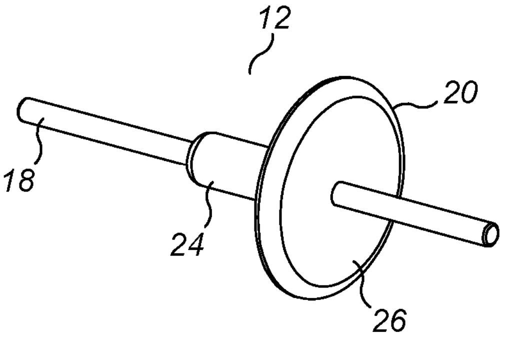
Figure 2C:
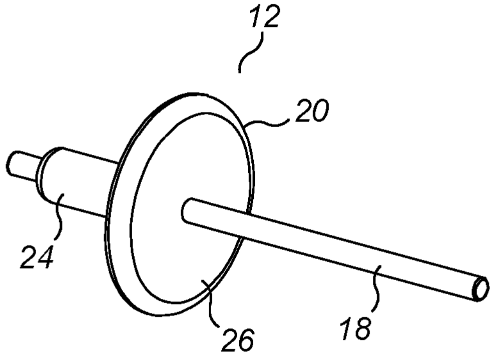
Figure 3A:
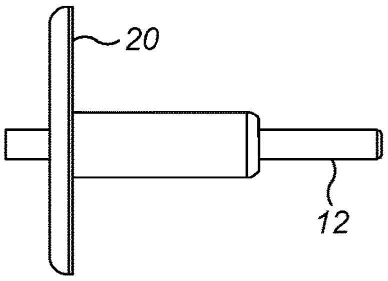
Figure 3B:
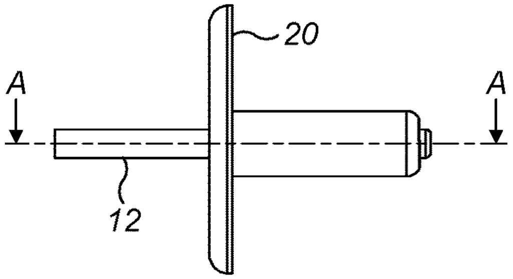
Figure 3C:
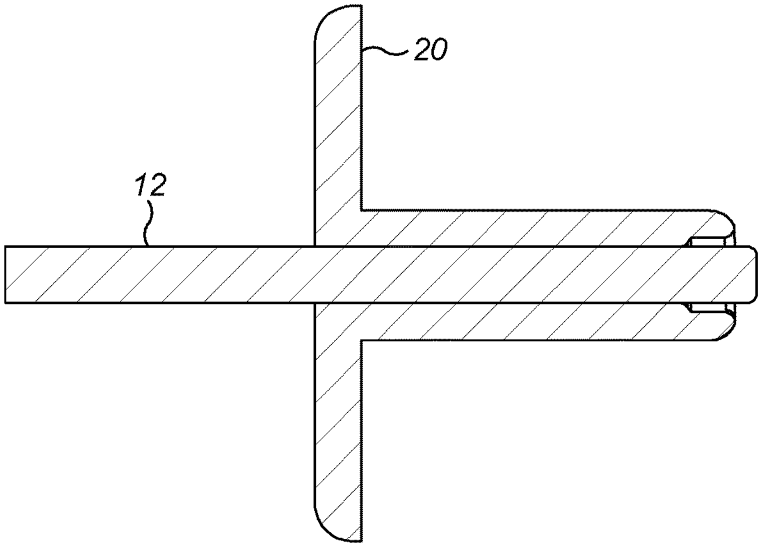
Figure 3D:
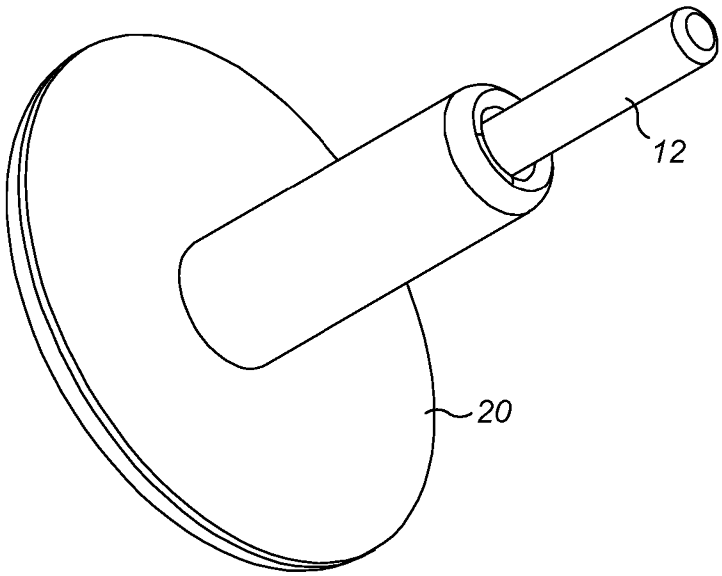
Figure 3E:
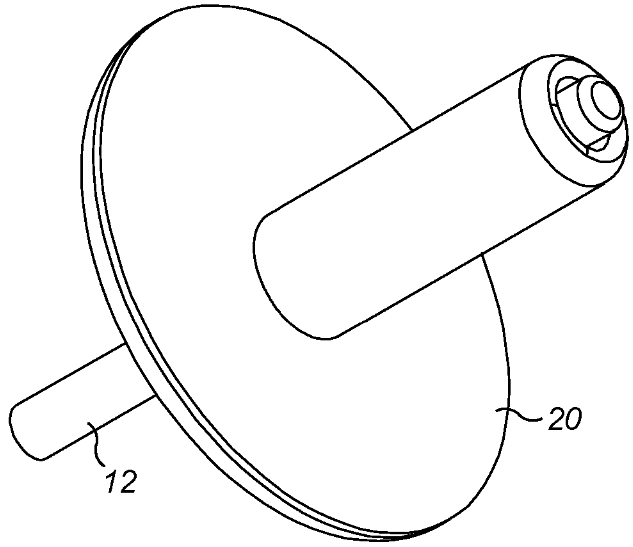
Figure 3F:
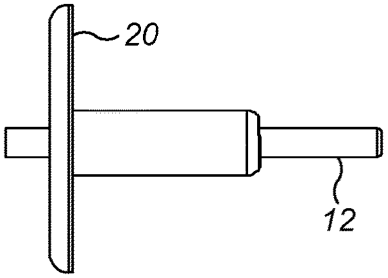
Figure 3G:
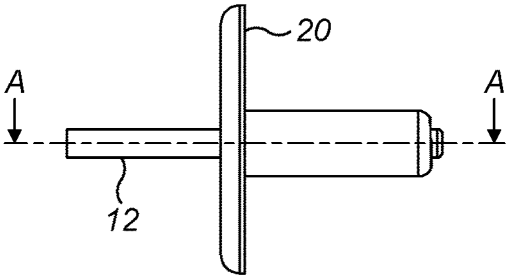
Figure 3H:
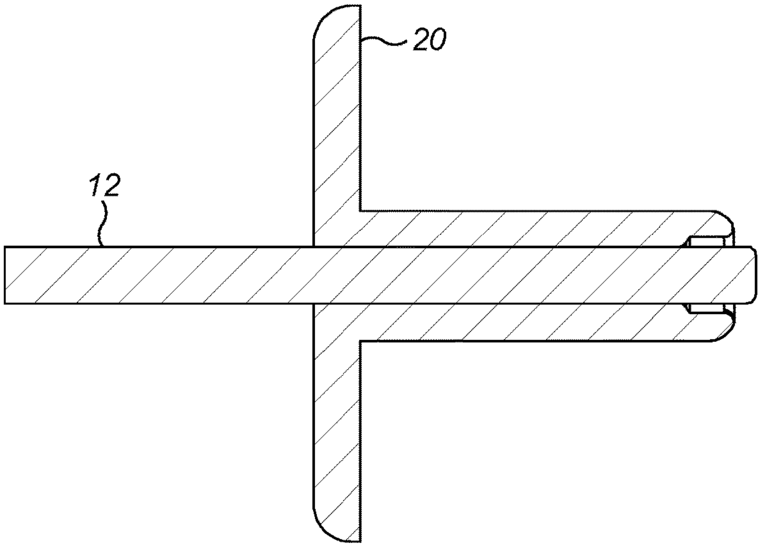
Figure 3I:
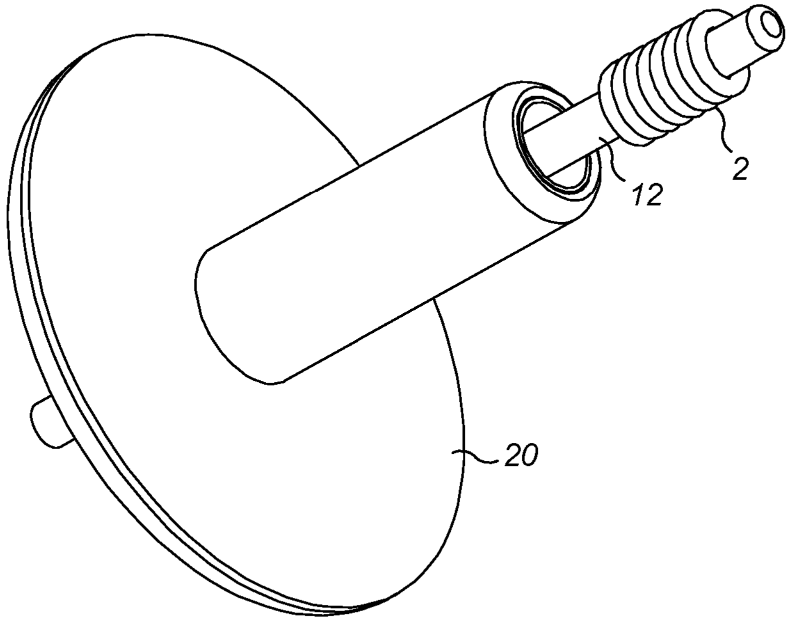
Figure 3J:
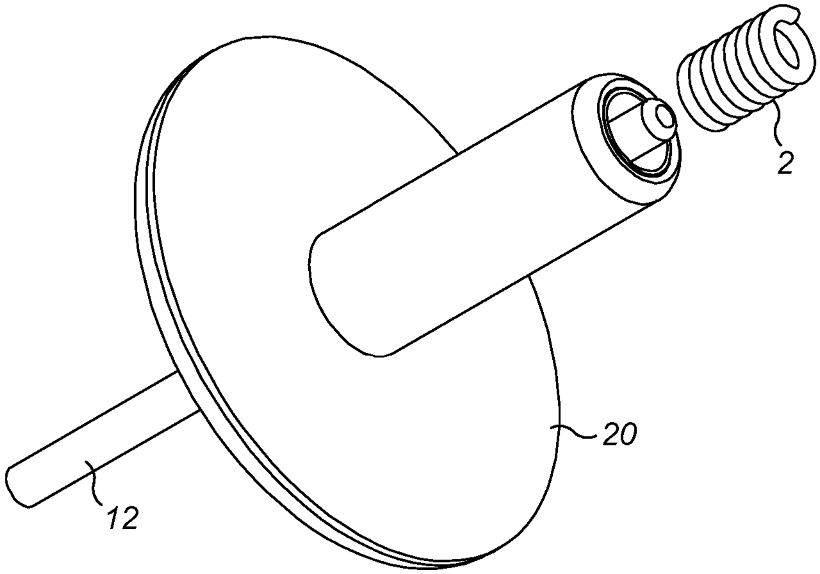
Figure 5A:
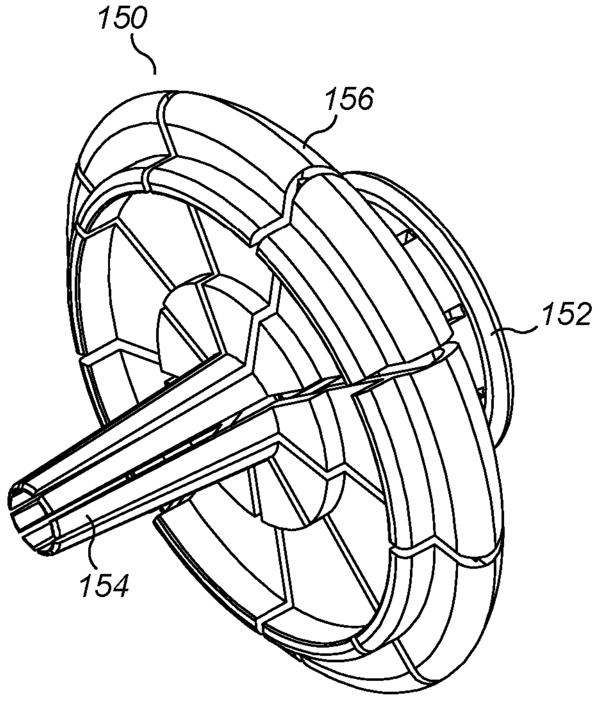
Figure 5B:
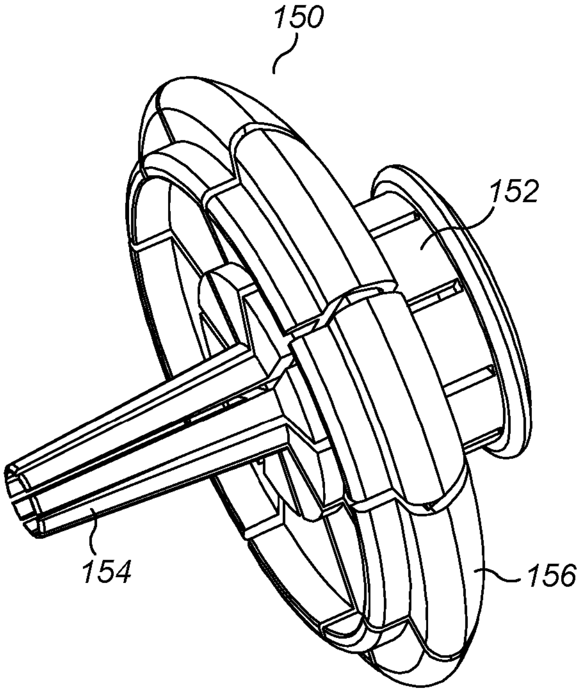
Figure 5C:
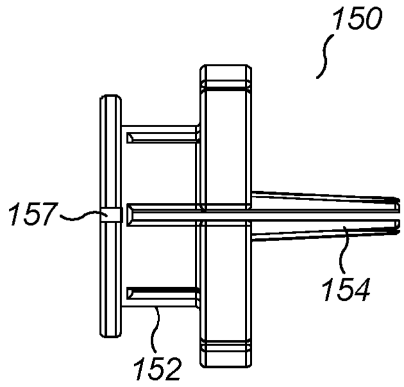
Figure 5D:
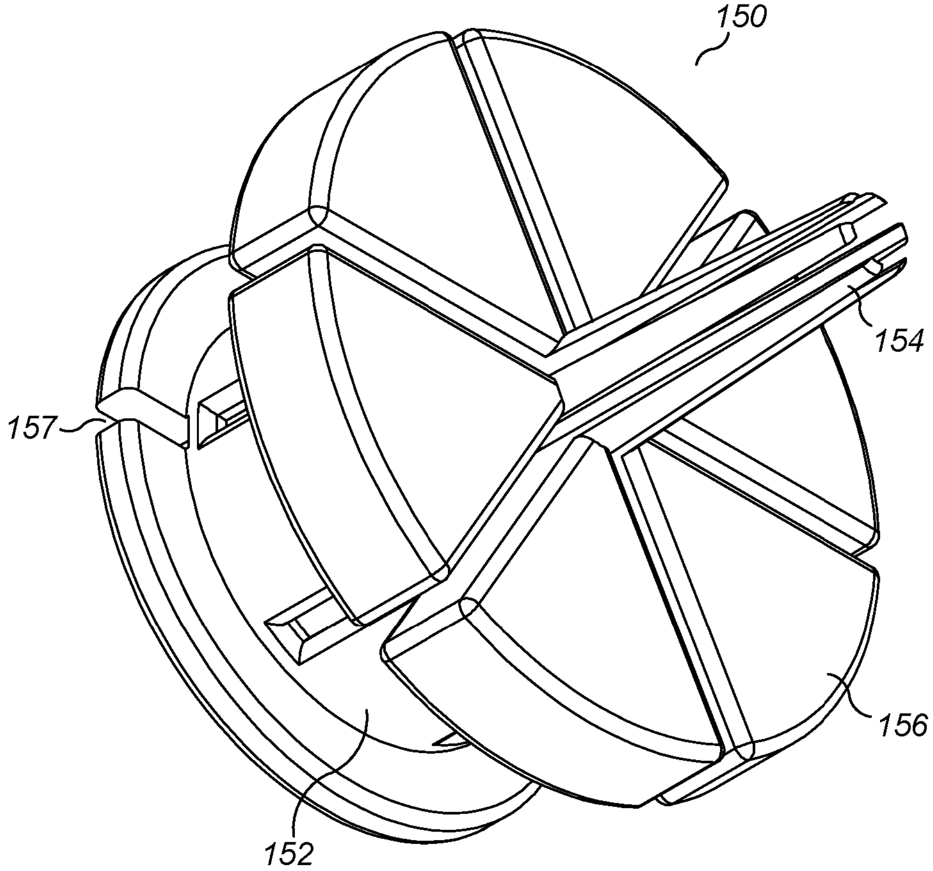
Figure 5E:
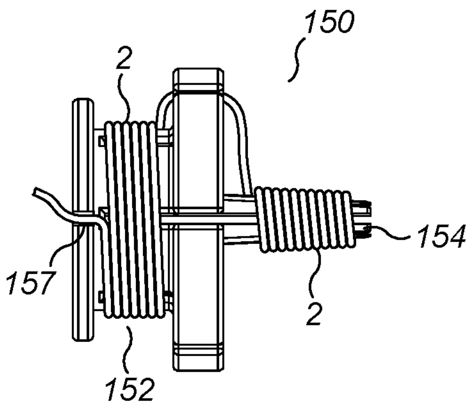
Figure 5F:
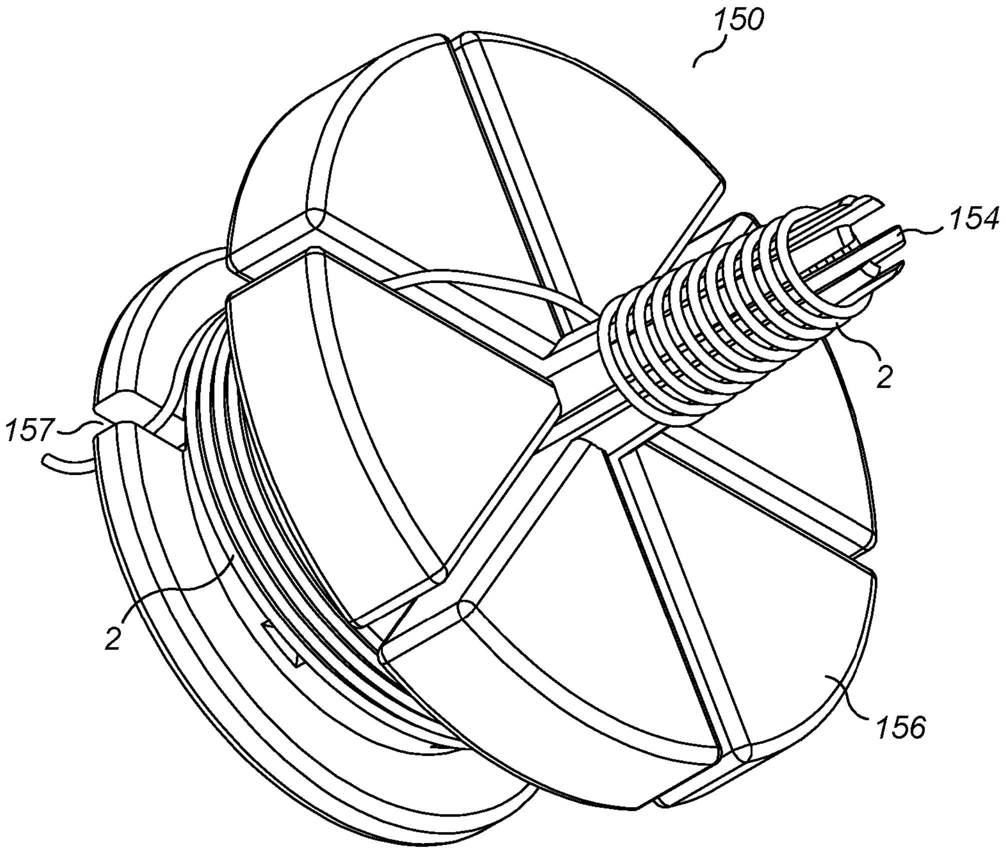
Figure 6A:
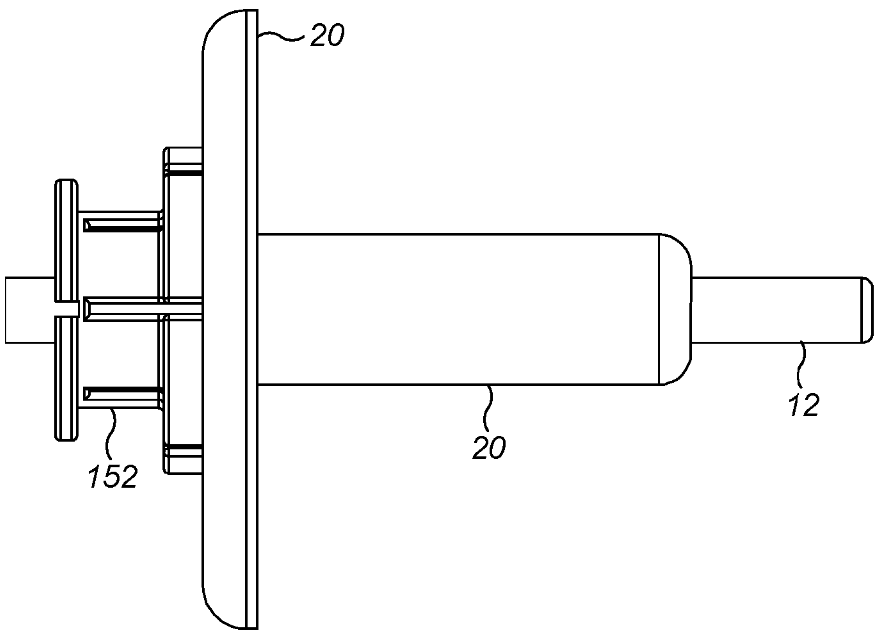
Figure 6B:
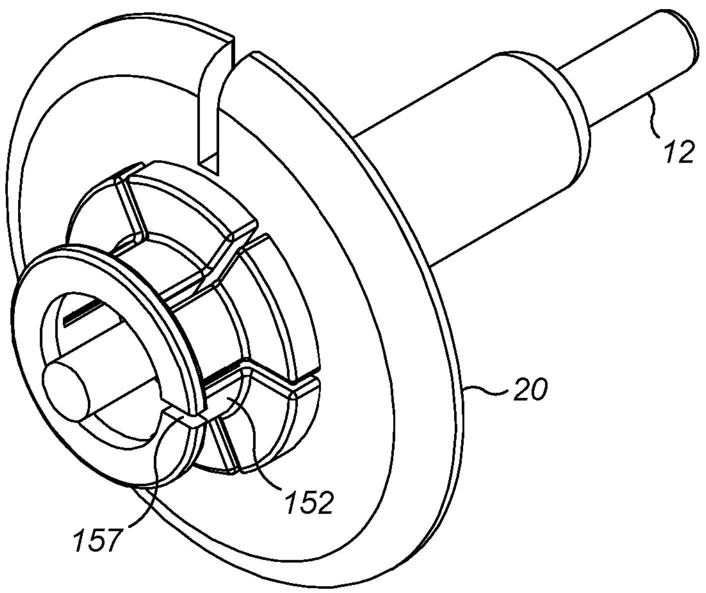
Figure 6C:
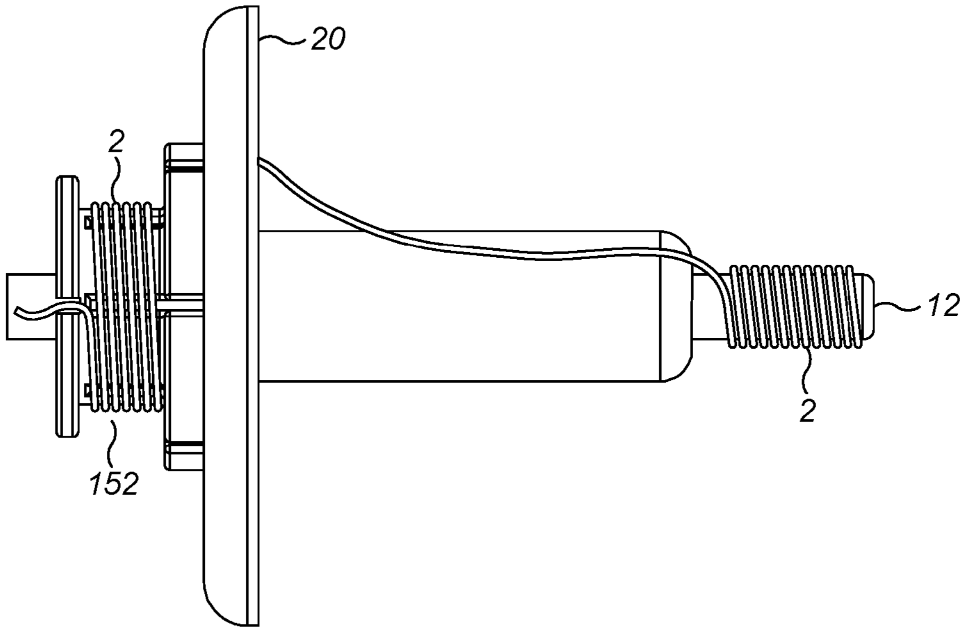
Figure 6D:
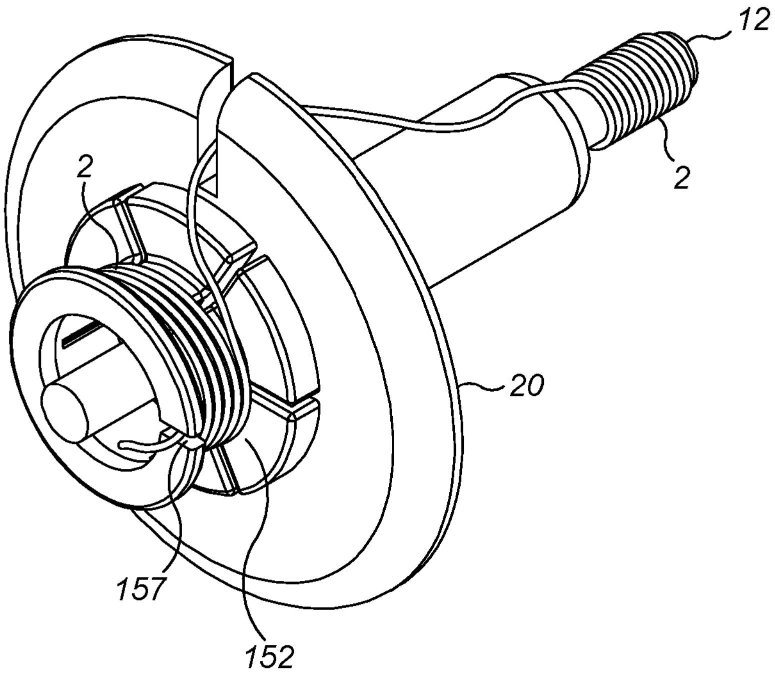
Figure 7A:
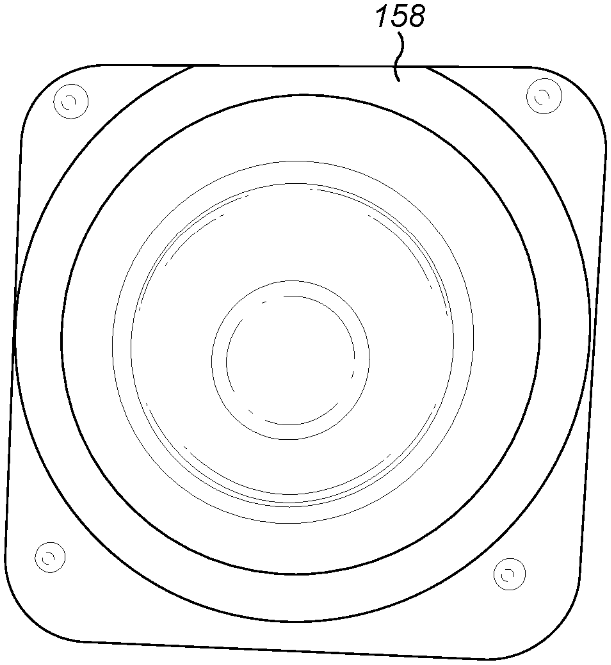
Figure 7B:
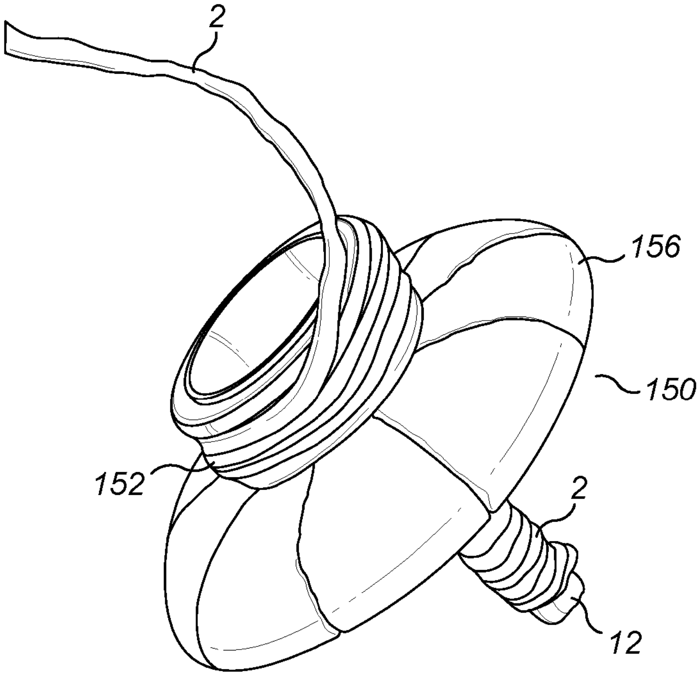
Figure 8A:
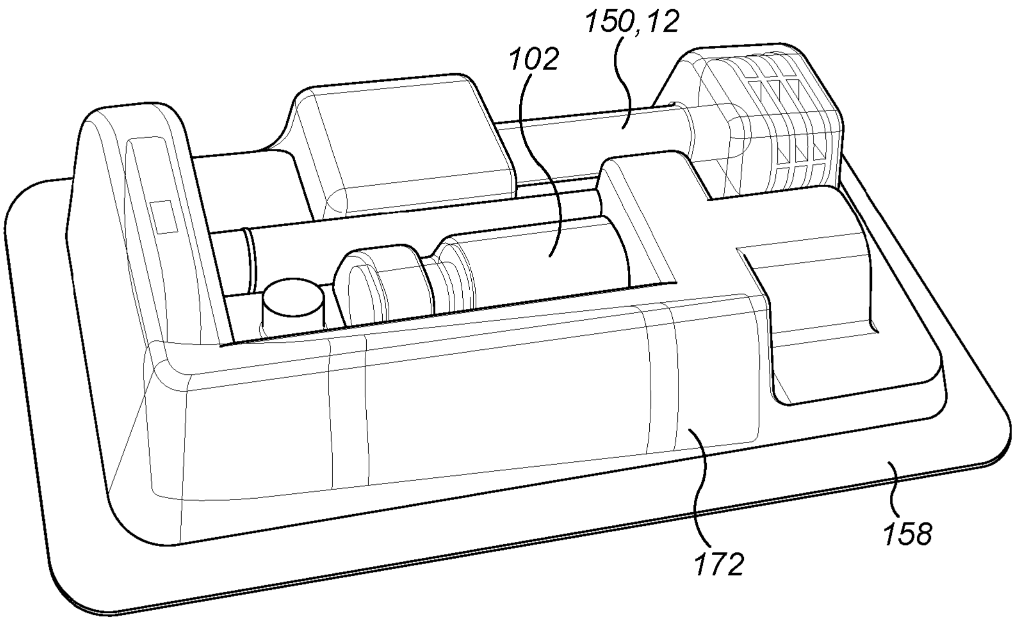
Figure 8B:
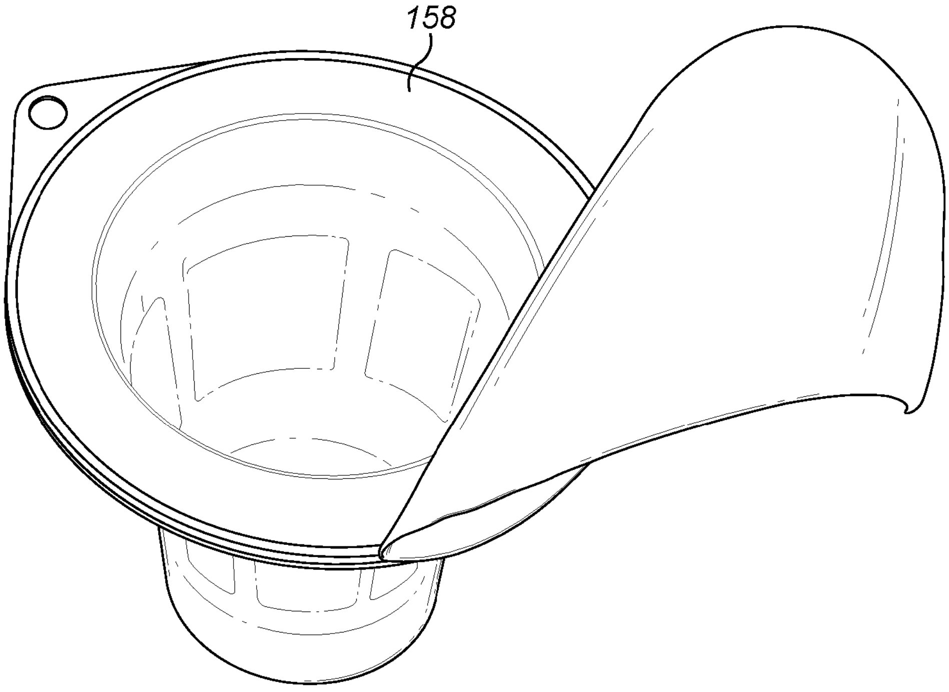
Figure 9A:
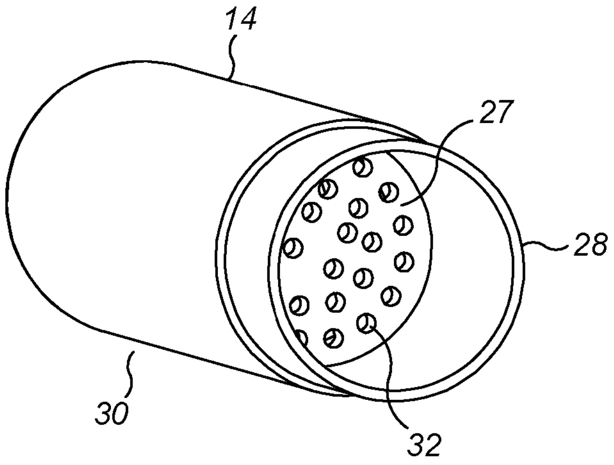
Figure 9B:
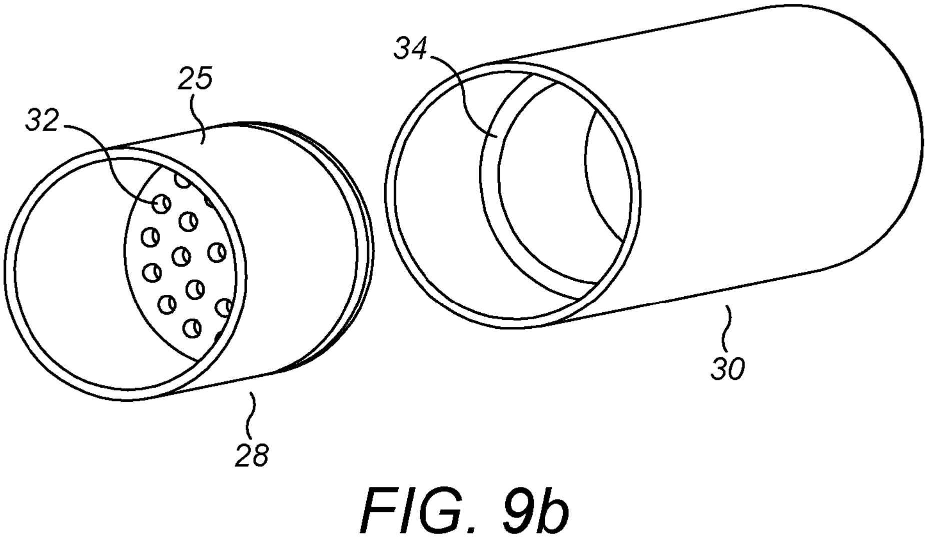
Figure 10:
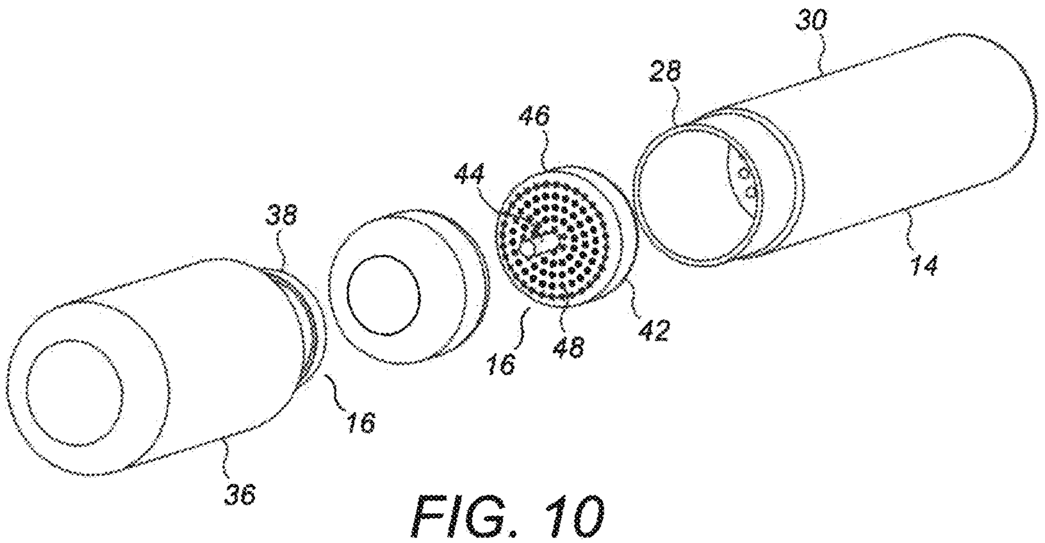
Figure 11A:
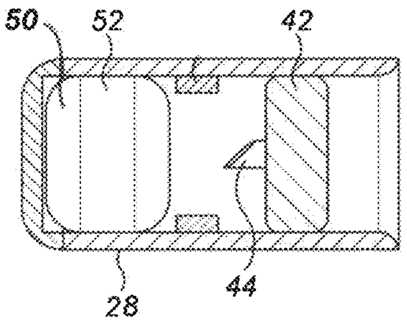
Figure 11B:
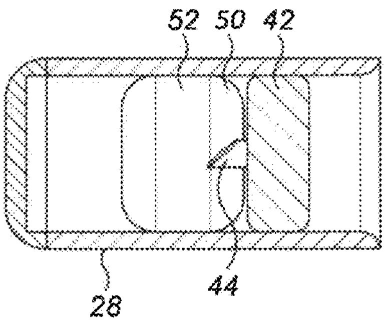
Figure 12A:
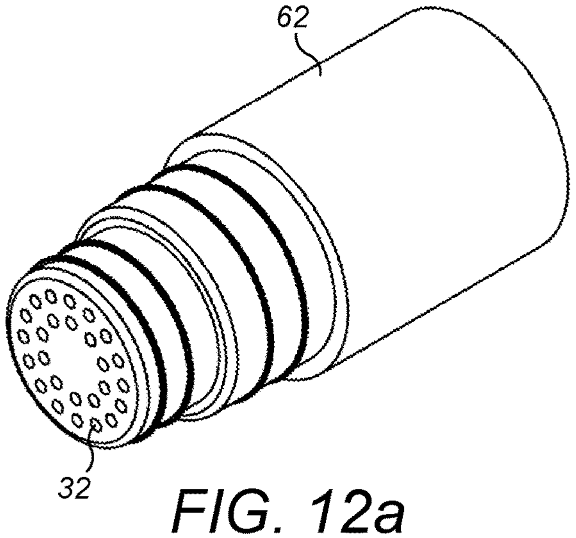
Figure 12B:
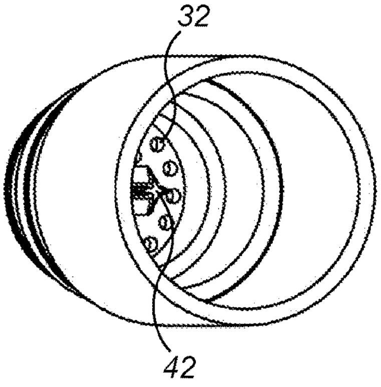
Figure 12C:
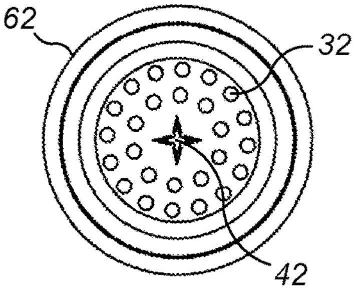
Figure 12D:
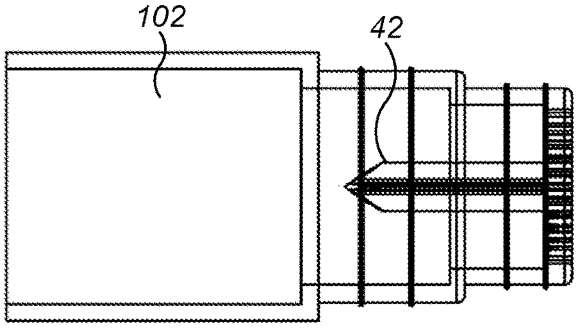
Figure 13A:
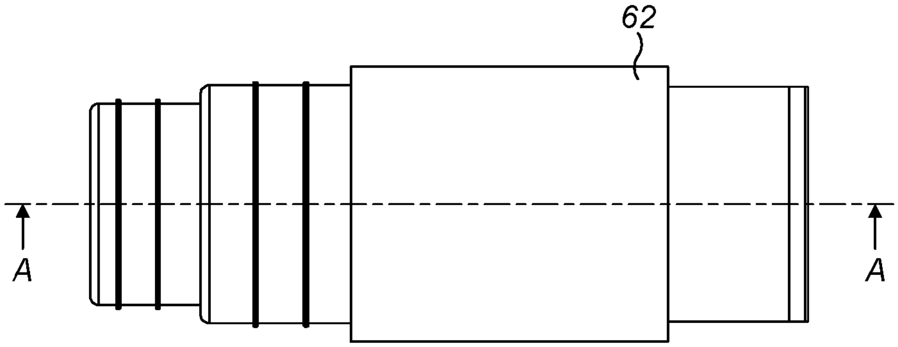
Figure 13B:
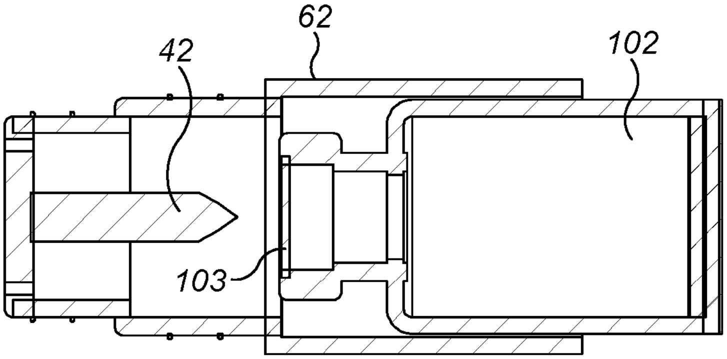
Figure 14A:
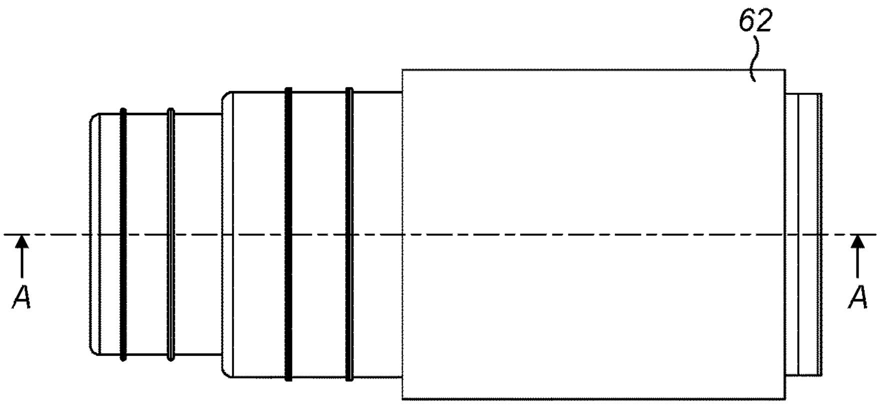
Figure 14B:
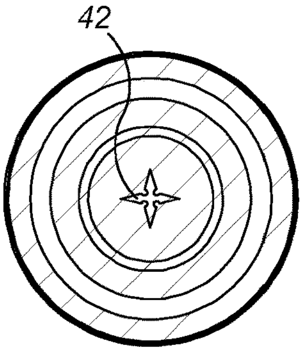
Figure 14C:
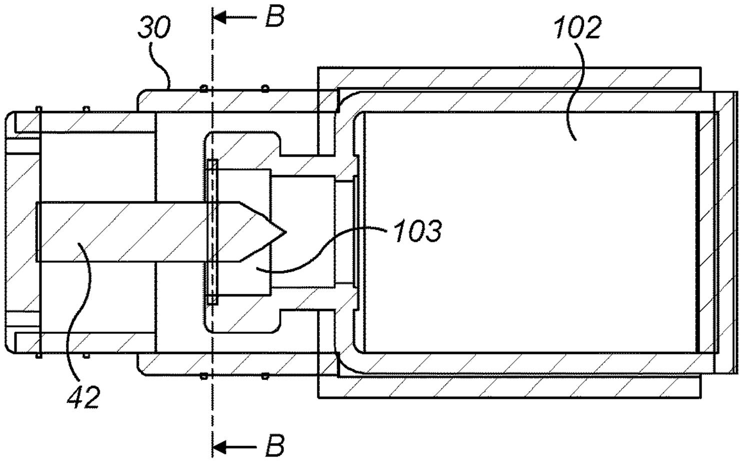
Figure 15A:
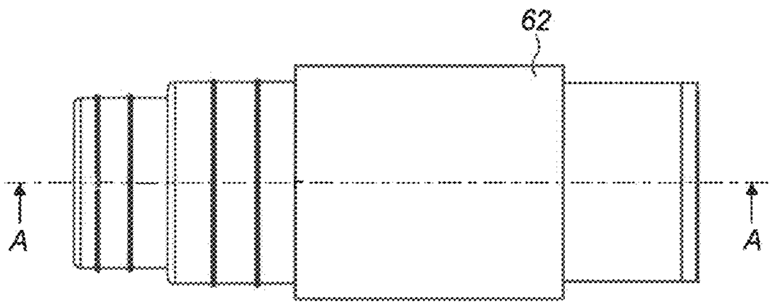
Figure 15B:
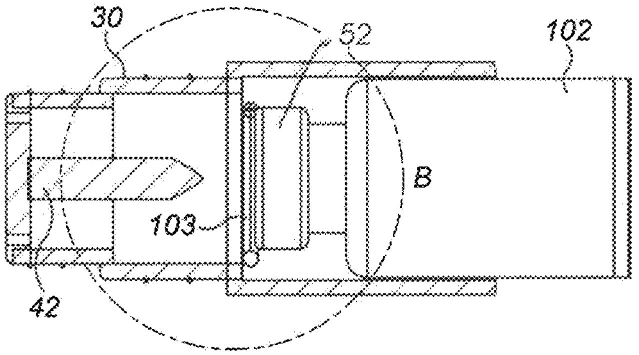
Figure 15C:
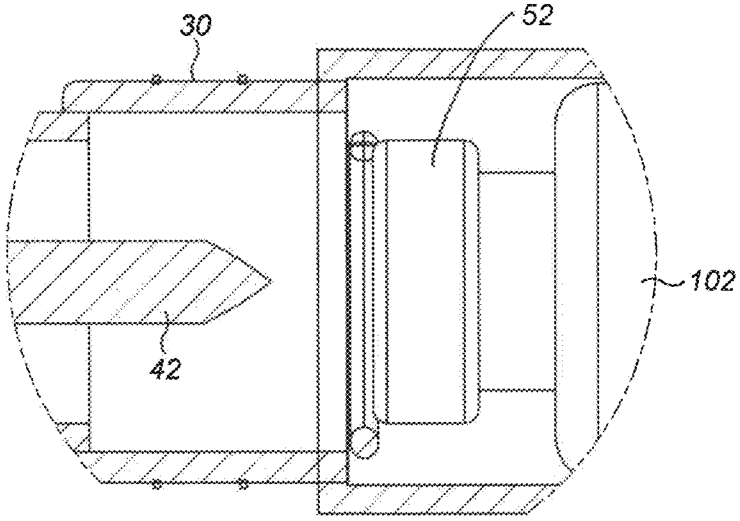
Figure 16A:
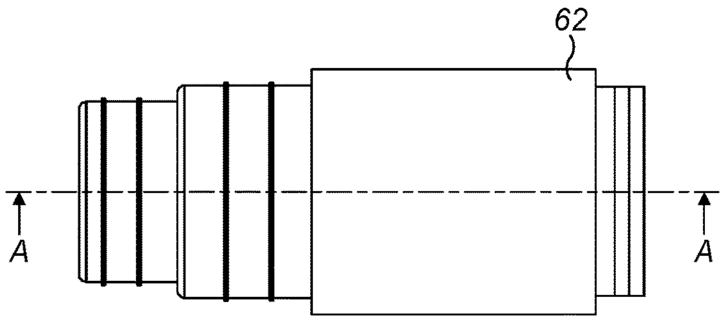
Figure 16B:
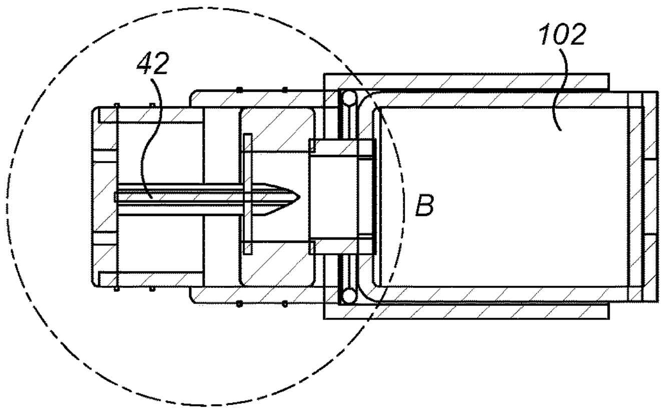
Figure 16C:
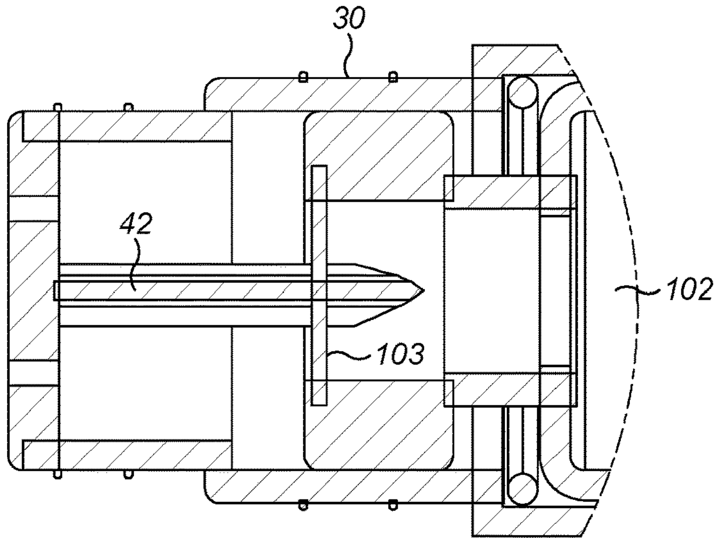
Figure 17A:
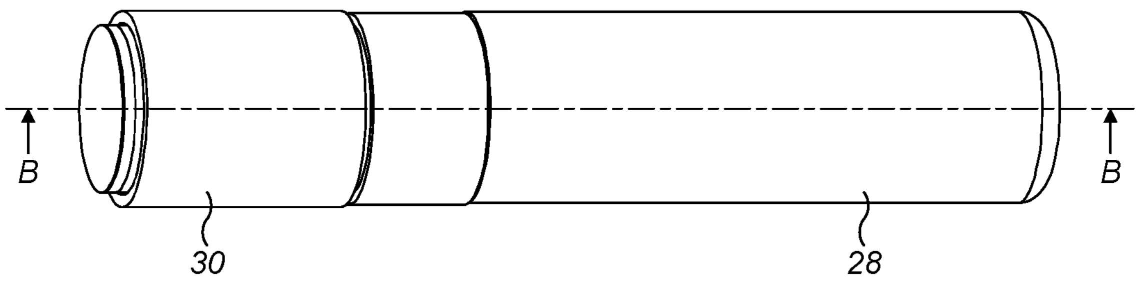
Figure 17B:
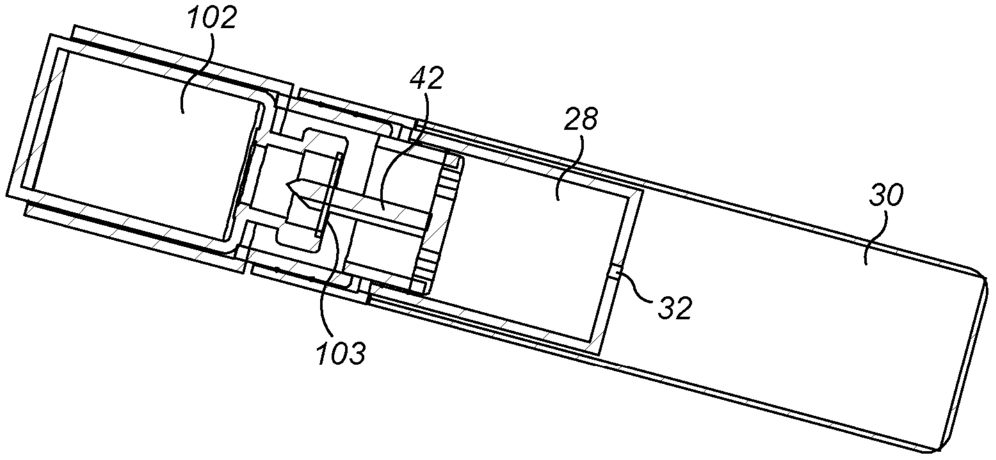
Figure 18A:
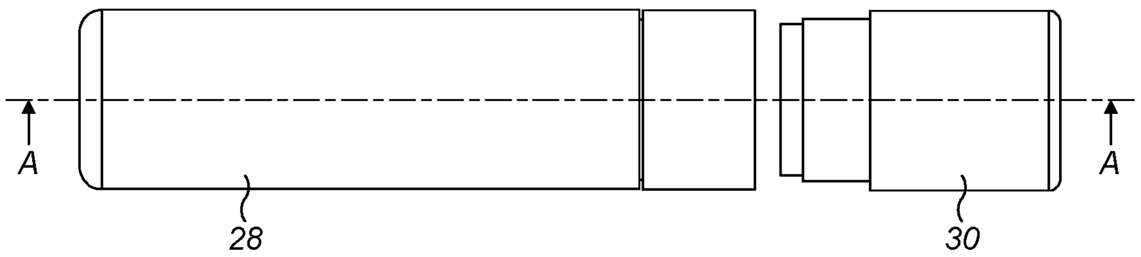
Figure 18B:
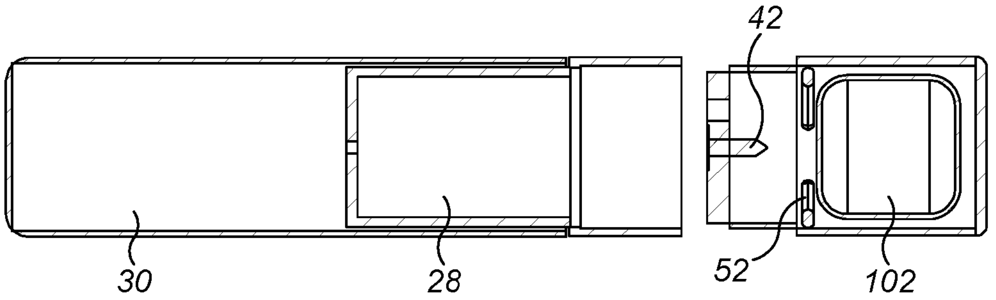
Figure 19A:
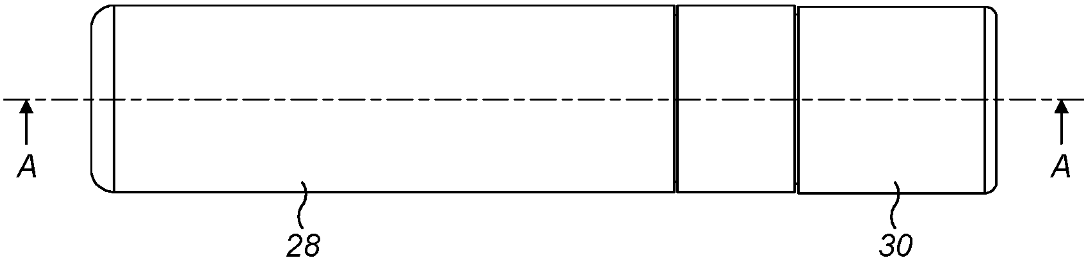
Figure 19B:
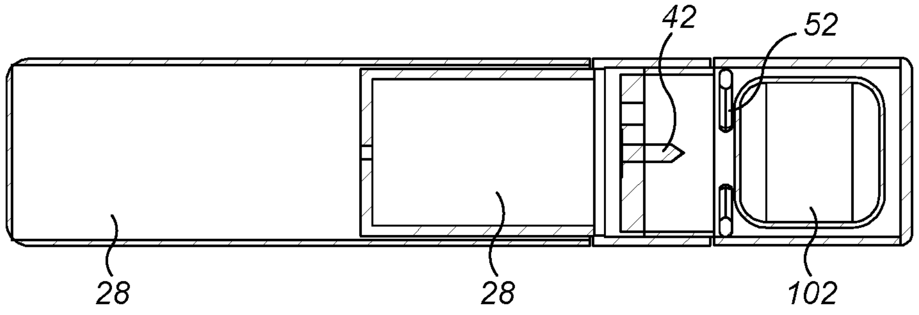
Figure 20A:
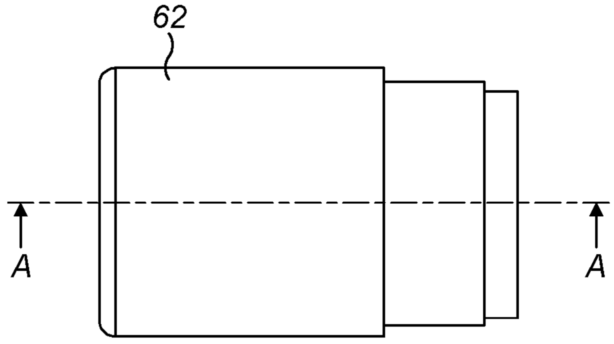
Figure 20B:
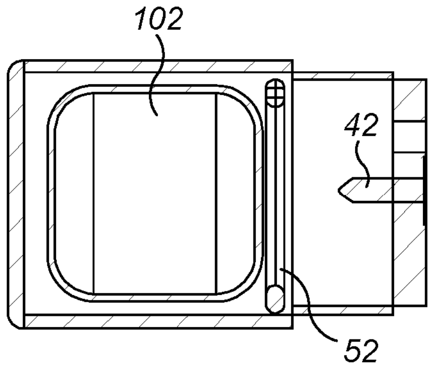
Figure 20C:
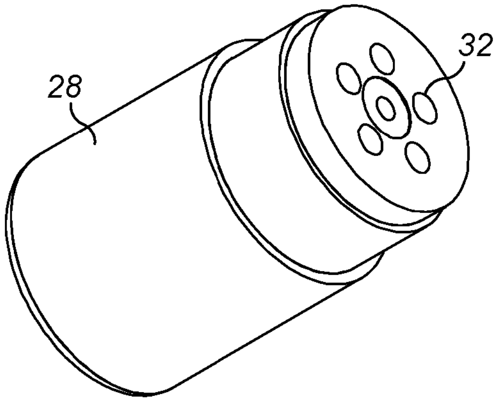
Figure 21A:
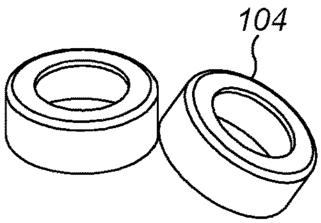
Figure 21B:
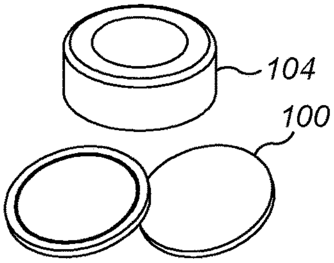
Figure 21C:
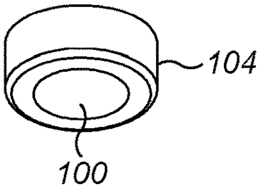
Figure 21D:
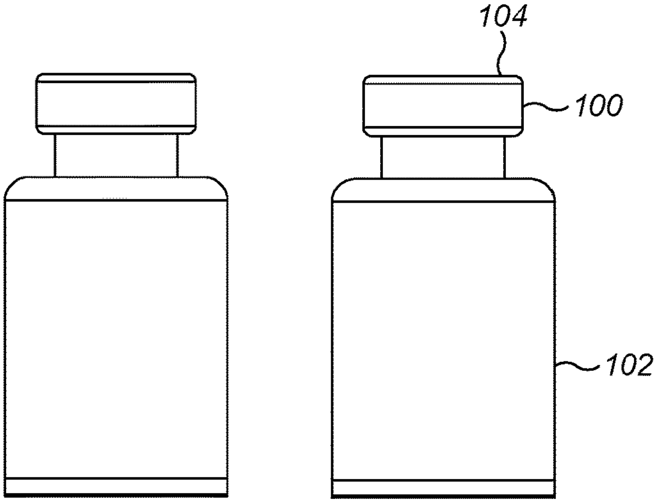
Figure 22A:
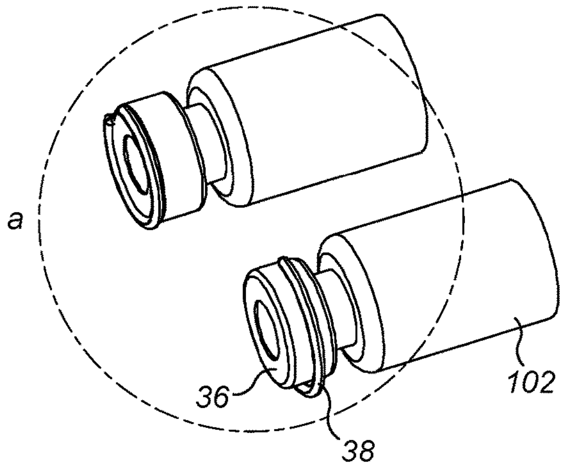
Figure 22B:
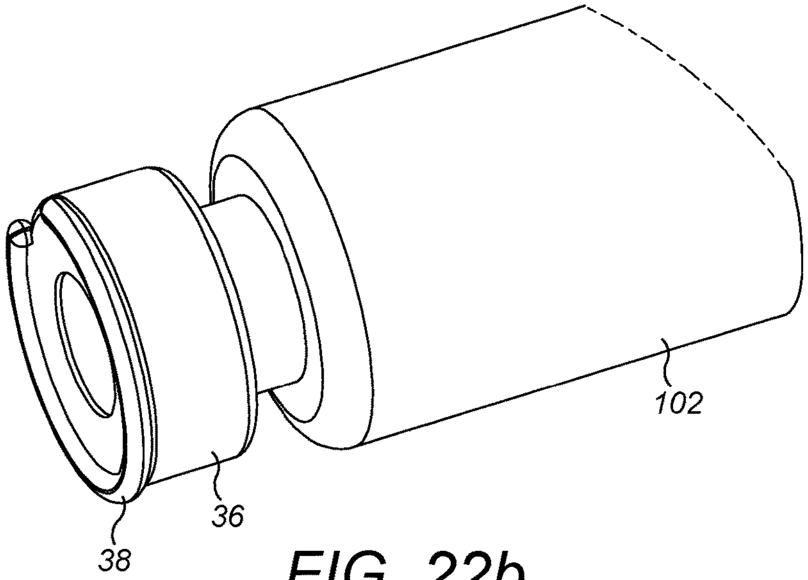
Figure 22C:
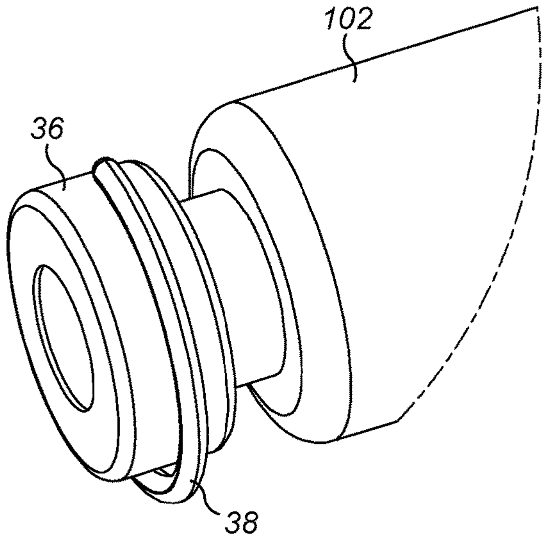
Figure 23A:
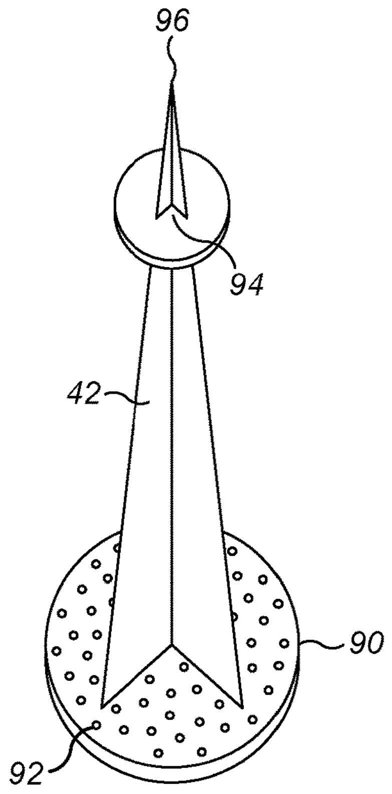
Figure 23B:
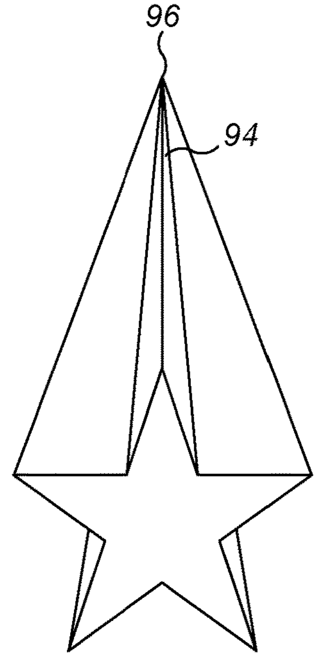
Figure 24A:
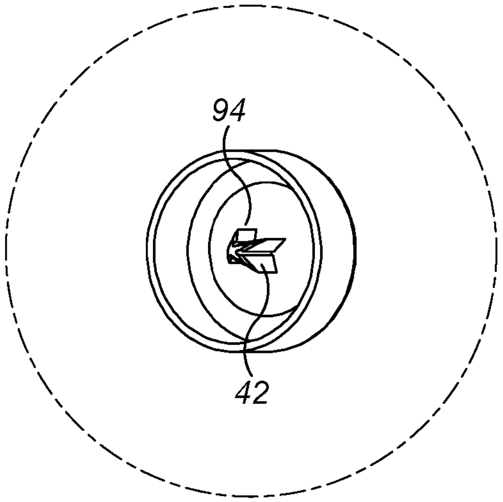
Figure 24B:
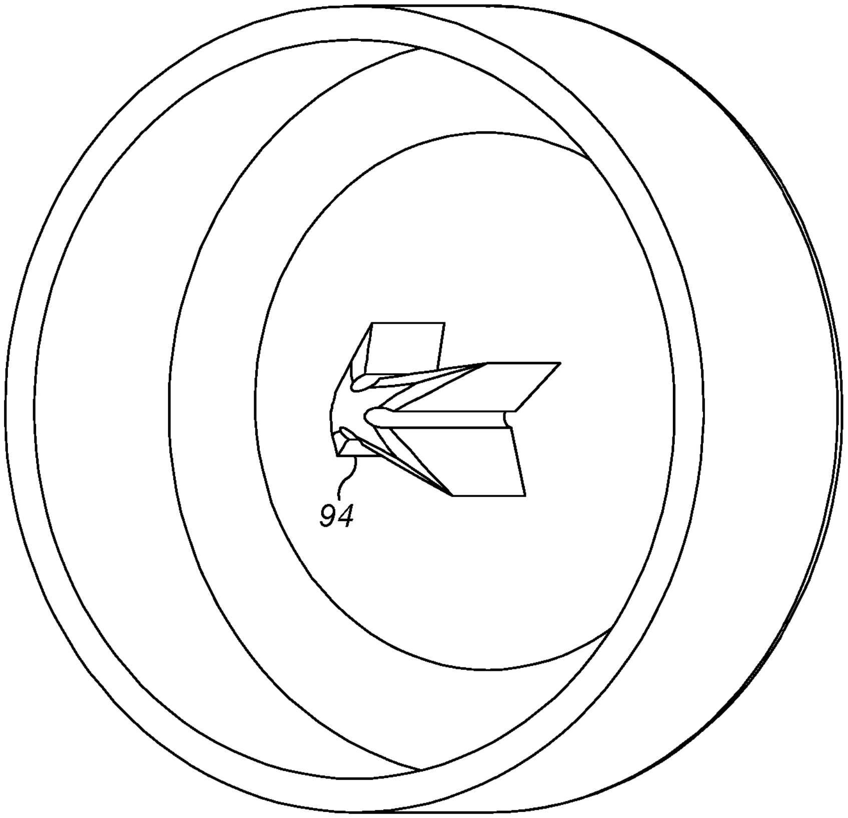
Figure 24C:
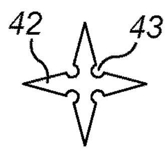
Figure 24D:
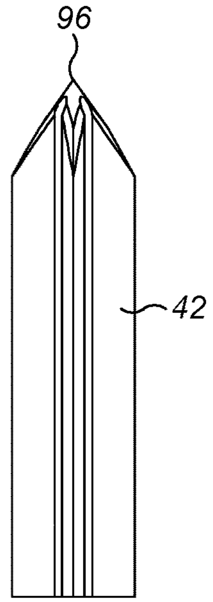
Figure 24E:
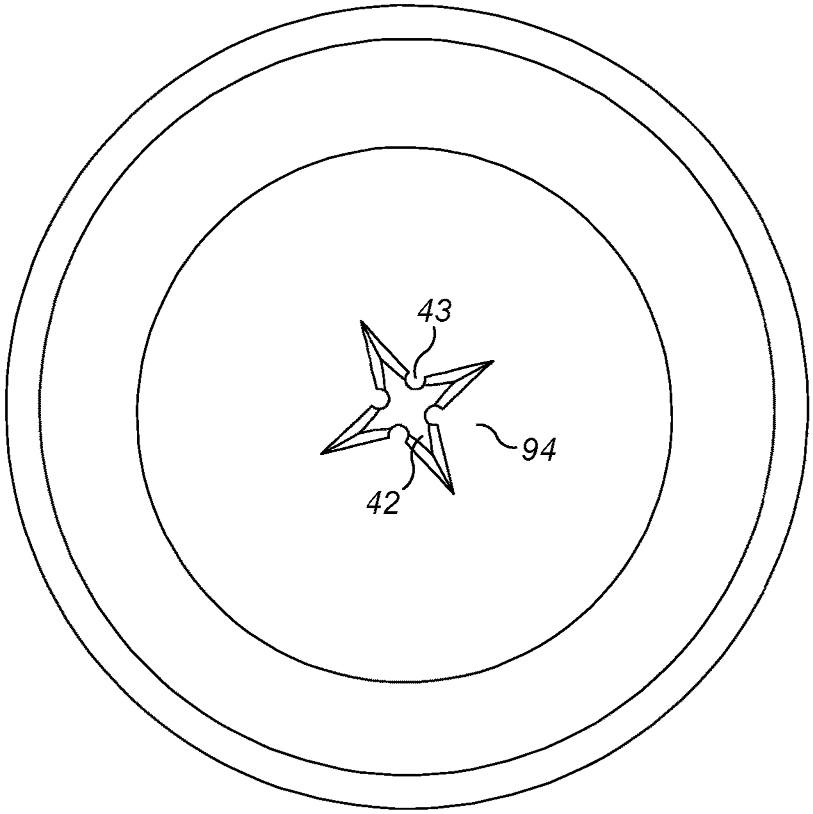
Figure 25A:
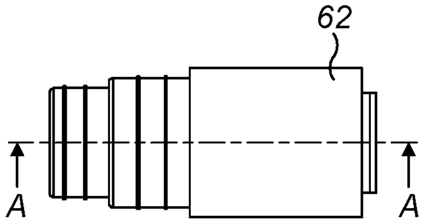
Figure 25B:
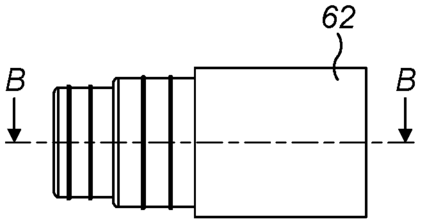
Figure 26A:
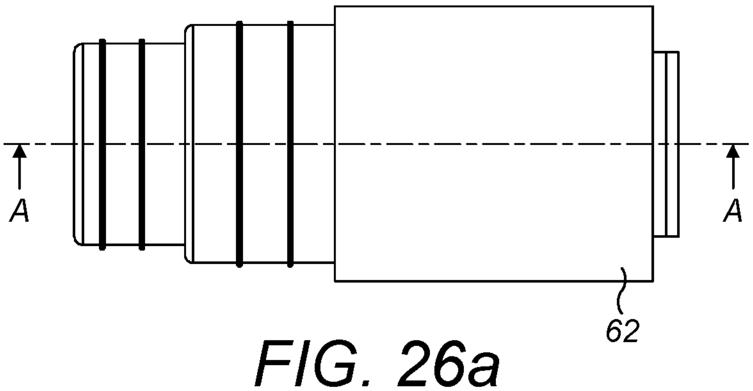
Figure 26B:
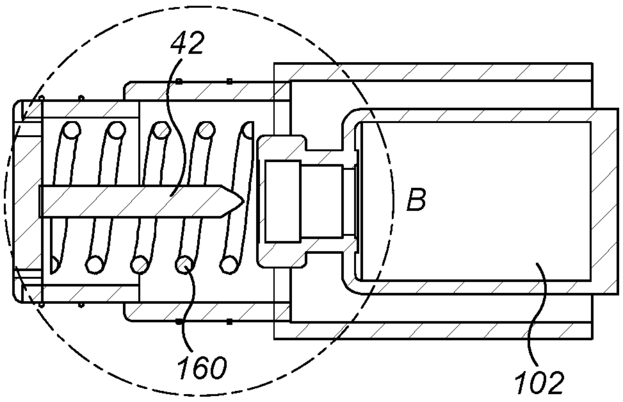
Figure 26C:
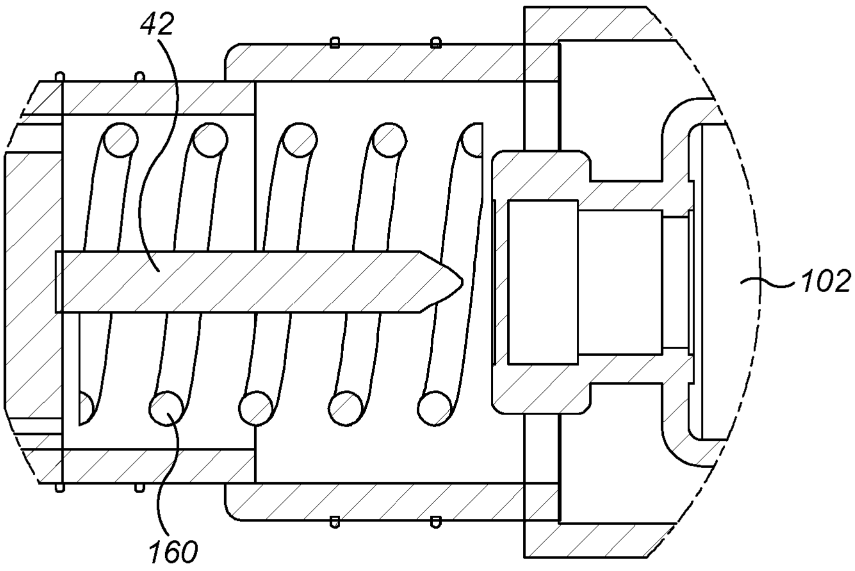
Figure 27A:
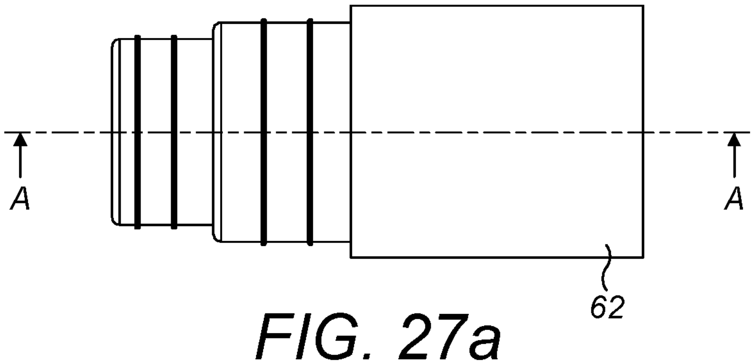
Figure 27B:
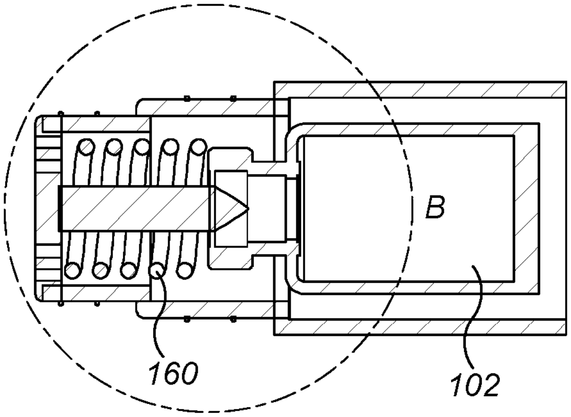
Figure 27C:
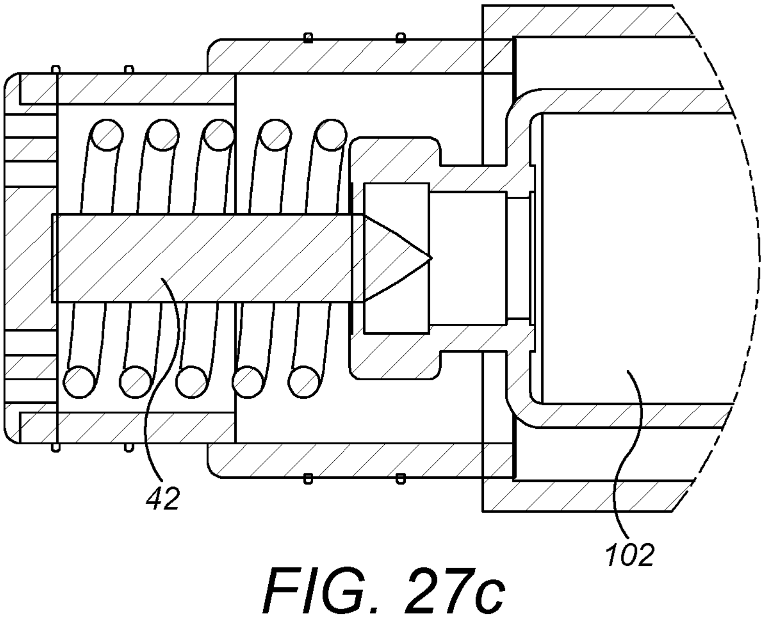
Figure 28:
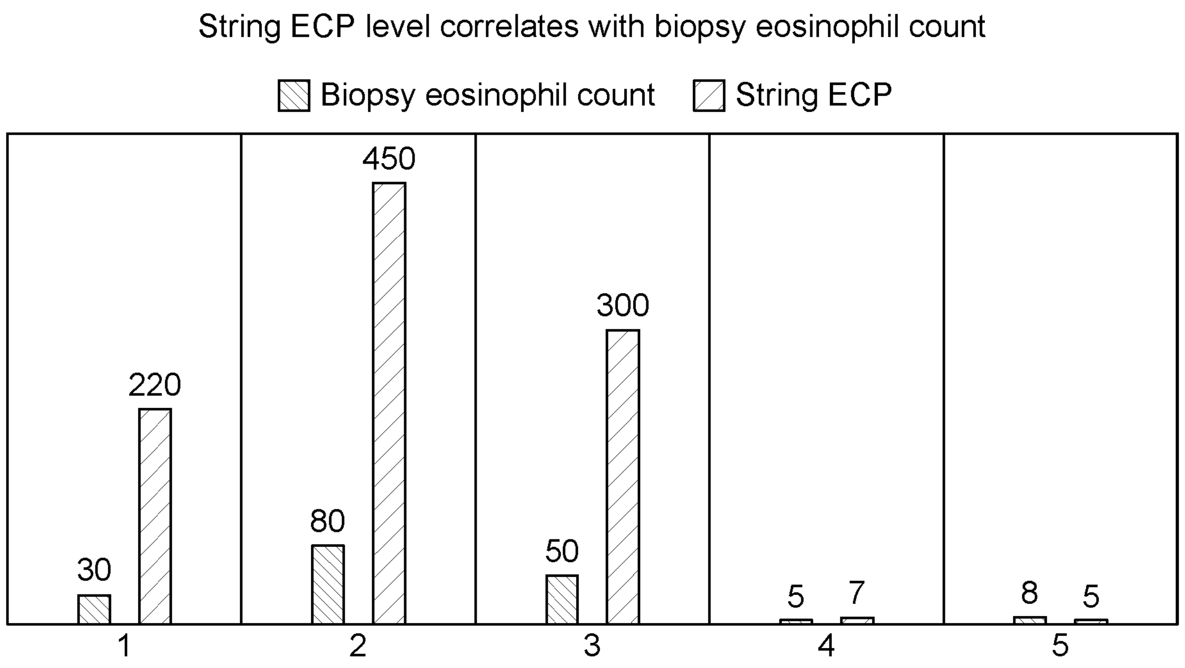
Figure 29:
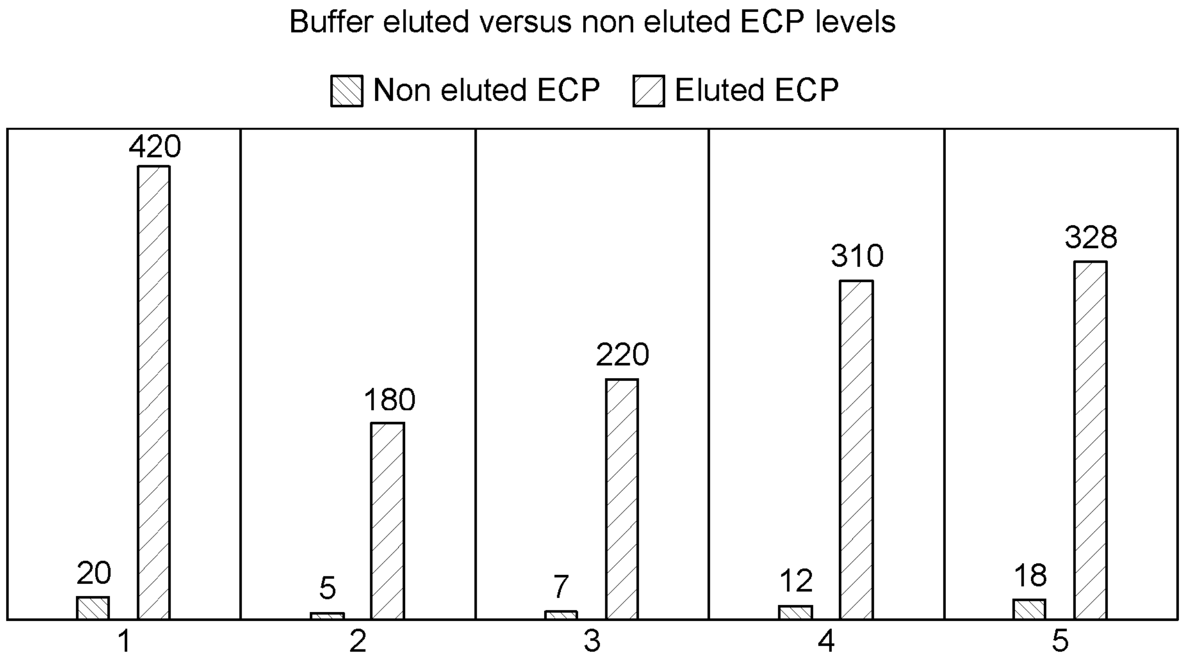

The invention will now be further described by way of illustrative example, wherein:

FIG. 1*a* shows a schematic view of a string in accordance with an embodiment of the invention;

FIG. 1*b* shows a schematic view of a plurality of strings in accordance with an embodiment of the invention;

FIG. 2*a* shows a side perspective view of a string capture rod in a first configuration in accordance with an embodiment of the invention;

FIG. 2*b* shows a side perspective view of a string capture rod in a second configuration in accordance with an embodiment of the invention;

FIG. 2*c* shows a side perspective view of a string capture rod in a third configuration in accordance with an embodiment of the invention;

FIG. 3*a* shows a side plan view of a string capture rod in accordance with an embodiment of the invention an open position;

FIG. 3*b* FIG. 3*a* shows a side plan view of a string capture rod in accordance with an embodiment of the invention a closed position;

FIG. 3*c* shows a side sectional view of a string capture rod in accordance with an embodiment of the invention in a closed position;

FIG. 3*d* shows a side perspective view of a string capture rod in accordance with an embodiment of the invention in an open position;

FIG. 3*e* shows a side perspective view of a string capture rod in accordance with an embodiment of the invention in a closed position;

FIG. 3*f* shows a side plan view of a string capture rod in accordance with an embodiment of the invention in an open position;

FIG. 3*g* shows a side view of a string capture rod in accordance with an embodiment of the invention in a closed position;

FIG. 3*h* shows a side schematic view of a string capture rod in accordance with an embodiment of the invention in a closed position;

FIG. 3*i* shows a side perspective view of a string capture rod in accordance with an embodiment of the invention in an open position, in combination with string;

FIG. 3*j* shows a side perspective view of a string capture rod in accordance with an embodiment of the invention in a closed position, wherein the string has been removed from the string capture rod;

FIGS. 4*a* to 4*f* show a plan view of a string capture rod, a string removal means and a guard element in accordance with an embodiment of the invention;

FIGS. 5*a* and 5*b* show a perspective view of a string holder in accordance with an embodiment of the invention;

FIG. 5*c* shows a side plan view of a string holder in accordance with an embodiment of the invention;

FIG. 5*d* shows a side perspective view of a string holder in accordance with an embodiment of the invention;

FIG. 5*e* shows a side view of a string holder in accordance with an embodiment of the invention, in combination with string;

FIG. 5*f* shows a side perspective view of a string holder in accordance with an embodiment of the invention, in combination with string;

FIG. 6*a* is a side plan view of a string holder in accordance with an embodiment of the invention;

FIG. 6*b* is a side perspective view of a string holder in accordance with another embodiment of the invention;

FIG. 6*c* shows a side view of a string holder in accordance with an embodiment of the invention, in combination with string;

FIG. 6*d* shows a side perspective view of a string holder in accordance with an embodiment of the invention, in combination with string;

FIG. 7*a* is a front view of packaging for a string holder in accordance with an embodiment of the invention;

FIG. 7*b* is a side perspective view of a string holder in accordance with another embodiment of the invention;

FIG. 8*a* is a side perspective view of packaging for a string holder and a centrifuge activated device according to an embodiment of the invention;

FIG. 8*b* is a side perspective view of packaging for a string holder in accordance with an embodiment of the invention;

FIG. 9*a* shows a perspective view of string holding apparatus in an assembled configuration in accordance with an embodiment of the invention;

FIG. 9*b* shows a perspective view of string holding apparatus in a disassembled configuration in accordance with an embodiment of the invention;

FIG. 10 shows a side view of string holding apparatus and string extraction apparatus in accordance with an embodiment of the invention;

FIG. 11*a* shows a schematic view of a string piercing device and a container comprising an extraction buffer prior to centrifugation;

FIG. 11*b* shows a schematic view of a string piercing device and a container comprising an extraction buffer during centrifugation;

FIG. 12*a* shows a side perspective view of part of a centrifuge activated device in accordance with an embodiment of the invention;

FIG. 12*b* shows a front perspective view of part of a centrifuge activated device in accordance with an embodiment of the invention;

FIG. 12*c* shows a top view of part of part of a centrifuge activated device in accordance with an embodiment of the invention;

FIG. 12*d* shows a side sectional view of part of a centrifuge activated device in accordance with an embodiment of the invention;

FIG. 13*a* shows a side schematic view of part of a centrifuge activated device in accordance with an embodiment of the invention;

FIG. 13*b* shows a side plan view of part of a centrifuge activated device in accordance with an embodiment of the invention;

FIG. 14*a* shows a side schematic view of part of a centrifuge activated device in accordance with an embodiment of the invention;

FIG. 14*b* shows a top view of part of a centrifuge activated device in accordance with an embodiment of the invention;

FIG. 14*c* shows a side plan view of part of a centrifuge activated device in accordance with an embodiment of the invention;

FIG. 15*a* is a side plan view of part of a centrifuge activated device in accordance with an embodiment of the invention;

FIG. 15*b* is a side plan view of part of a centrifuge activated device in accordance with an embodiment of the invention;

FIG. 15*c* is a side plan view of the part of the centrifuge activated device denoted by B in FIG. 15*b*, in accordance with an embodiment of the invention;

FIG. 16*a* shows a side view of part of a centrifuge activated device in accordance with an embodiment of the invention;

FIG. 16*b* shows a side plan view of part of a centrifuge activated device in accordance with an embodiment of the invention;

FIG. 16*c* is a side plan view of the part of the centrifuge activated device denoted by B in FIG. 16*b*, in accordance with an embodiment of the invention;

FIG. 17*a* shows a side plan view of part of a centrifuge activated device in accordance with an embodiment of the invention;

FIG. 17*b* shows a side schematic plan view of part of a centrifuge activated device in accordance with an embodiment of the invention;

FIG. 18*a* shows a side plan view of part of a centrifuge activated device in accordance with an embodiment of the invention;

FIG. 18*b* shows a side plan view of part of a centrifuge activated device in accordance with an embodiment of the invention;

FIG. 19*a* shows a side plan view of part of a centrifuge activated device in accordance with an embodiment of the invention;

FIG. 19*b* shows a side plan view of part of a centrifuge activated device in accordance with an embodiment of the invention;

FIG. 20*a* shows a side plan view of part of a centrifuge activated device in accordance with an embodiment of the invention;

FIG. 20*b* shows a side plan view of part of a centrifuge activated device in accordance with an embodiment of the invention;

FIG. 20*c* is a side perspective view of part of a centrifuge activated device in accordance with an embodiment of the invention;

FIG. 21*a* shows a schematic view of a cap that may be used in accordance with an embodiment of the invention;

FIG. 21*b* shows a schematic view of a stopper and cap that may be used in accordance with an embodiment of the invention;

FIG. 21*c* shows a schematic view of a stopper and cap combination that may be used in accordance with an embodiment of the invention;

FIG. 21*d* shows a schematic view of a bottle in combination with a stopper and cap that may be used in accordance with an embodiment of the invention;

FIGS. 22*a* to 22*c* are side schematic views of part of a buffer holder in accordance with an embodiment of the invention;

FIG. 23*a* shows a schematic view of a piercing device that may be used in accordance with an embodiment of the invention;

FIG. 23*b* shows a schematic view of another piercing device that may be used in accordance with another embodiment of the invention;

FIG. 24*a* is a side perspective view of part of a centrifuge activated device comprising a piercing device in accordance with an embodiment of the invention;

FIG. 24*b* is a side perspective view of part of a centrifuge activated device comprising a piercing device in accordance with an embodiment of the invention;

FIG. 24*c* is a top view of a piercing device in accordance with an embodiment of the invention;

FIG. 24*d* is a side view of a piercing device in accordance with an embodiment of the invention;

FIG. 24*e* is a top plan view of a centrifuge activated device and piercing device in accordance with an embodiment of the invention;

FIGS. 25*a* and 25*b* are a side view of part of a centrifuge activated device in accordance with an embodiment of the invention;

FIGS. 25*c* to 25*f* show a side view of part of a centrifuge activated device comprising a spring in accordance with an embodiment of the invention;

FIG. 26*a* is a side view of part of a centrifuge activated device comprising a spring in accordance with an embodiment of the invention;

FIGS. 26*b* and 26*c* are a side view of part of a centrifuge activated device comprising a spring in accordance with an embodiment of the invention;

FIG. 27*a* is a side view of part of a centrifuge activated device comprising a spring in accordance with an embodiment of the invention;

FIGS. 27*b* and 27*c* are a side view of part of a centrifuge activated device comprising a spring in accordance with an embodiment of the invention;

FIG. 28 shows a graph showing the correlation between string ECP levels and biopsy eosinophil count; and FIG. 29 shows a graph showing the correlation between the buffer eluted versus non-eluted ECP levels.

With reference to FIG. 1, there is provided apparatus 1 comprising a string 2 for insertion into the oesophagus of a patient, the string comprising proximal end 4 and a distal end 6, wherein the string forms a structure 8 at the distal end to assist in the insertion of the string into the patient.

In the embodiment shown in FIG. 1, the structure 8 provided at the distal end 6 of the string 2 comprises a helical component. In other embodiments, the string may be modified to form a compressed pellet of string or a knot at the distal end. Advantageously, the provision of a string having a structure at the distal end that is formed from the string itself avoids the problems associated with including a non-string component at the distal end (such as gelatine) which may become stuck or cause oesophageal irritation. Advantageously, the provision of a string having a helical component at the distal end thereof provides a structure that is flexible and soft to assist in swallowing the string. The size of the structure at the distal end of the string is optimised such that it is small enough that it does not cause irritation to the oesophagus, whilst still being capable of being swallowed by a patient. In one embodiment, the size of the structure at the distal end of the string is equivalent to a size 5 capsule (having a length of approximately 11.1 mm and a width of approximately 4.9 mm), but can be of larger or smaller size if needed.

The proximal end is the end of the string that is nearest the user rather than the patient.

The helical component 8 at the distal end of the string is formed by soaking the distal end of the string in a solution that will confer rigidity on the string once dry, wrapping the distal end of the string around a rod and allowing the string to dry. The string may be soaked in a solution of corn starch, for example, 1% corn starch solution. Alternatively, the string may be dipped in sterile water, wound around the outer surface of a metal rod, and then heated to a temperature of approximately 100° C. for approximately 10 minutes. Advantageously, the helical component at the distal end of the string provides a structure that is flexible and soft to assist in insertion into the oesophagus of a patient, yet rigid to assist in the patient swallowing the string.

The string further comprises a structure at the proximal end 4 thereof, wherein the structure provided at the proximal end comprises a compressed or knotted portion of the string. The structure provided at the proximal end 4 of the string assists in attachment of the string to a cheek of the patient. Advantageously, the provision of a string having a structure at the proximal end thereof assists in attachment of the proximal end of the string to a patient such that the string is not inadvertently detached or swallowed by the patient during insertion of the string, thus improving safety and ease of use.

The proximal end of the string is attached to a patient using an attachment means in the form of a skin-adhesion grade tape to improve comfort for the patient. Advantageously, the use of tape to secure the string to the patient improves security and reduces the risk of unwanted detachment of the string from the patient. The string attachment means may comprise an adhesive removable label to which details regarding the sample type, date sample taken, patient identifiers (such as name, age, date of birth, unique patient identifier such as NHS or hospital number) can be added. Advantageously, this improves sample identification and reduces the risk if sample error (such as sample mix up). The label may be removed from the string and placed on the tube to which to string will be inserted post-use, prior to sending to the laboratory.

The string 2 that is used in FIG. 1 comprises a medical grade string.

The string may be coated with a biological macromolecule, such as a protein which may act as a marker for a condition. In another embodiment, the string may be coated with a dye or other marker. In another embodiment, the string may be coated with or encompass a pharmaceutical agent for administration to a patient.

The structure at the distal end of the string may be coated with a flavouring. In one embodiment, the structure at the distal end of the string may be coated with at least one drop, preferably two to three drops, of flavouring essence. Advantageously, coating the structure at the distal end of the string with a flavouring can encourage swallowing of the string by patients. This is particularly beneficial in children.

In one embodiment, the string is used to absorb a biological component following insertion into the oesophagus of a patient. Preferably, when the string has been inserted into the oesophagus of a patient, the string absorbs a protein such as eosinophilic cationic protein (ECP). ECP is known to be a marker for the condition eosinophilic esophagitis (EoE), such that the detection of this protein may indicate that the patient is suffering from this condition.

The string may be used to measure IgG4 levels in the fluid that is absorbed by the string. Advantageously, the presence of IgG4 levels will help to distinguish reflux oesophagitis from eosinophilic oesophagistis, since IgG4 is only present in the latter. Advantageously, the presence of IgG4 antibodies can also be used to test for possible food triggers for eosinophilic oesophagitis (for example, food specific IgG4 antibodies) to help guide a food elimination diet to treat this disease. Advantageously, if a specific IgG4 antibody is detected in relation to a specific food, then eliminating these foods would bring the disease into remission.

The string has a length to ensure that, when inserted into a patient, the string is in contact with the entire length of the oesophagus of the patient. Preferably, the string has a length to ensure that the structure at the distal end of the string enters the stomach of the patient. Advantageously, providing a string that has a length such that it is in contact with the entire length of the oesophagus assists in the adequate placing of the string within a patient.

In some embodiments, segments of the string may be analysed separately following removal of the string from the oesophagus of a patient. In one embodiment, the string may comprise an interval marker which may comprise an ink or dye. In another embodiment, the interval marker may comprise at least one knot provided on the string. In this embodiment, following removal of the string from a patient, the string may be cut at the intervals shown by the interval markers and individual segments may be analysed separately.

The string may be analysed following insertion into a patient to determine whether the distal end of the string has entered the stomach of the patient. Typically, following removal of the string from a patient, the chemical composition of the distal end of the string is analysed. In one embodiment, the pH of the distal end of the string may be analysed, for example using a pH indicator dye or paper. Typically, if the distal end of the string has been present in the stomach of the patient, the pH of the distal end of the string will be acidic, due to the acidic nature of the stomach. In another embodiment, following removal of the string from a patient, the distal end of the string may be analysed to test for other stomach markers such as pepsin or gastrokines.

In one embodiment, the string may be coated with a substance that will provide a stimulus to oesophageal lining of the patient, for example, wherein the substance will provoke an inflammatory response by the oesophageal lining. The substance that provides a stimulus will typically interact with other biological mediators that are released in response. In one embodiment, the string may be coated with a cytokine, a weak acid or alkaline substance or a food, such as a whole food or a food component. In one embodiment, the string may be coated with whole milk. In another embodiment, the string may be coated with ovalbumin. In the embodiment wherein the substance providing the stimulus is embedded within the string, the position of the substance on the string will be marked, for example, using a dye or ink or by knotting the string. In this embodiment, string segments on either side of the stimulus can be removed (e.g. cut out) and biological components of inflammation measured using the kit as shown in FIGS. 2 to 27. In the embodiment wherein the provoking stimulus is applied to the string, the segment of the string coated with the stimulus is covered with a protective film to protect the stimulus from being washed away during the swallowing process. The protective film typically comprises a dissolvable substance such as gelatine, wherein the dissolvable substance will dissipate once in place to reveal the stimulus.

As shown in FIG. 1*b*, the apparatus may comprise a plurality of strings for insertion into the oesophagus of a patient. Preferably, the plurality of strings in combination form a single structure at the distal end thereof. Preferably, the apparatus comprises a plurality of separate strings which combine at the distal end of each string to form a single structure to assist in insertion of the strings into a patient. Preferably, the structure provided at the distal end of the plurality of strings comprises a helical component. In another embodiment, the structure provided at the distal end of the plurality of strings comprises a compressed pellet. Advantageously, the use of a plurality of strings assists in the detection of more than one component when the string is subsequently analysed following removal from a patient. In one embodiment, the use of a plurality of strings may assist in the detection of one or more chemical, protein or antibody component. This is particularly important since oesophageal diseases can be difficult to detect and may affect different regions of the oesophagus. If a single string is inserted into a patient, following removal of the string, the string is typically cut into segments and each segment is analysed in different tests. In this embodiment, it may be possible to miss an area of disease within the oesophagus of a patient. Advantageously, the use of multiple strings means that each string contacts the lining of the oesophagus and thus, each string may be separately analysed following removal from a patient, thus providing a more accurate result.

The apparatus of the present invention may be used in human and/or veterinary medicine. Typically, humans and/or animals may chew a string to collect saliva for analysis using the apparatus of the invention. In another embodiment, the string may be used to collect and test the saliva of humans. Typically, in this embodiment, the saliva of humans may be collected and used to carry out antibody, DNA and/or RNA tests.

Following removal of the string from a patient, the string is analysed in a laboratory to check for any biological components that may have bound to the string when it was inserted in the patient.

Levels of string ECP isolated from the oesophagus of patients with eosinophilic oesophagitis correlates with levels of eosinophils in biopsy specimens from these patients. A high string ECP correlates with a high biopsy eosinophil count. The results of this study is shown in the Graph of FIG. 28. In patients with eosinophilic oesophagitis, oesophageal biopsies revealed >15 eosinophils per high power field (diagnostic criteria for eosinophilic oesophagitis). These patients all had raised string ECP levels (patients 1, 2, and 3). Patients without eosinophilic oesophagitis (<15 eosinophils per high power field) had very low levels of string ECP (patient 4 and patient 5). In patients with a high eosinophil count from an oesophageal biopsy (eosinophils per high power field) an oesophageal string test revealed a corresponding high string ECP value (μg/l) (as shown in patients 1, 2 and 3). In patients with a normal oesophageal biopsy eosinophil count, the corresponding ECP value was low (patients 4 and 5)

ECP collected by the oesophageal string test adheres to the string and centrifugation alone is not sufficient to remove it from the string. The addition of a low pH buffer to the string allows release of the ECP as shown in the graph of FIG. 29. String swallowed by patients (patients 1 to 5) with eosinophilic oesophagitis was collected (two strings per patient). One sample was placed in a centrifuge for 10 minutes at 500 g and the fluid collected and ECP levels measured. The second of the paired string samples was treated with a low pH buffer to remove the ECP (eluted) before centrifugation. Despite the dilution effect of adding a buffer to the string, much higher levels of ECP were detected when the elution step was used. The elution step removes the ECP stuck to the string. Similarly if one string is centrifuged to remove ECP and the liquid analysed, then the same string is treated with elution buffer and centrifuged to remove any remaining ECP on the string, significantly higher ECP levels are obtained with the elution step. The results showed the significantly higher ECP levels are obtained from oesophageal string test samples when an elution buffer is used to remove adherent ECP (μg/l) from the string compared with no elution buffer. Data was obtained from five separate samples (1, 2, 3, 4 and 5).

With reference to FIGS. 2 to 27, there is provided a kit 10 for use with the string 2 of FIG. 1*a*, the kit further comprising means for removing a sample from the string following insertion into a patient.

The kit comprises a string capture rod 12, string collection apparatus 14, string extraction apparatus 16 and/or a centrifuge tube.

As shown in FIG. 2, the string capture rod 12 assists in transfer of the string following removal from the oesophagus of a patient to a container. Advantageously, the use of a string capture rod 12 to transfer the string minimises sample contamination and reduces user risk.

The string capture rod 12 comprises a cylindrical element 18, wherein the string may be wound around the outer surface of the cylindrical element. The cylindrical element may be telescopic. Advantageously, the use of a telescopic cylindrical element 18 reduces the amount of space taken by the string capture rod, for example, during storage.

The string capture rod 12 has a length of approximately 16 cm.

The outer surface of the string capture rod 12 is substantially smooth and comprises a material such as Teflon or polypropylene.

At least one end of the cylindrical element is rounded, wherein the at least one end of the cylindrical element that is rounded is used to capture the string. Advantageously, the smooth rounded end of the cylindrical element prevents any unwanted tearing of the string during capture by the string capture element. Typically, the string is very sticky with respect to the string capture rod when the string is wet. Providing the string with a roughened distal end has the effect that the string will stick avidly to the string capture rod. Providing the string capture rod with a smooth distal end will assist in removal of the string from the string capture rod.

The string capture rod 12 further comprises a guard element 20 that is provided at the end 22 of the string capture rod that is held by a user. The guard element comprises a cylindrical portion 24 that is dimensioned such that it fits around the circumference of the cylindrical element. The guard element further comprises a circular portion 26 that is substantially perpendicular to the axis of the cylindrical portion 24 of the guard element 20 and extends therefrom. The guard element may slide along the longitudinal axis of the cylindrical element of the string capture rod. The string is wound around the cylindrical element and the user then slides the guard element along the longitudinal axis of the cylindrical element to push the string along the cylindrical element and into an appropriate container for transfer to the laboratory. Advantageously, the guard element provides protection to the string as it prevents the user from coming into contact with the string, thus minimising contamination of the string and protecting the user from the patient's oesophageal fluid.

In one embodiment, the string capture rod 12 comprises a metallic material. In this embodiment, the string capture rod 12 is reusable following sterilisation. In another embodiment, the string capture rod 12 comprises a plastics material. In this embodiment, the string capture rod is disposable. It is preferred that the string capture rod 12 is made from a material that is rigid enough to enable the string to be wound around the rod and smooth enough so as not to hinder the travel of the wound string along the cylinder length.

FIGS. 3*a* and 3*d* show the string capture rod 12 in an open position and FIGS. 3*b* and 3*e* show the string capture rod 12 in a closed position.

FIG. 3*i* shows a string capture rod with string 2 wrapped around the rod 12. FIG. 3*j* shows an embodiment wherein the string 2 has been removed from the string capture rod 12.

Figure 4A:
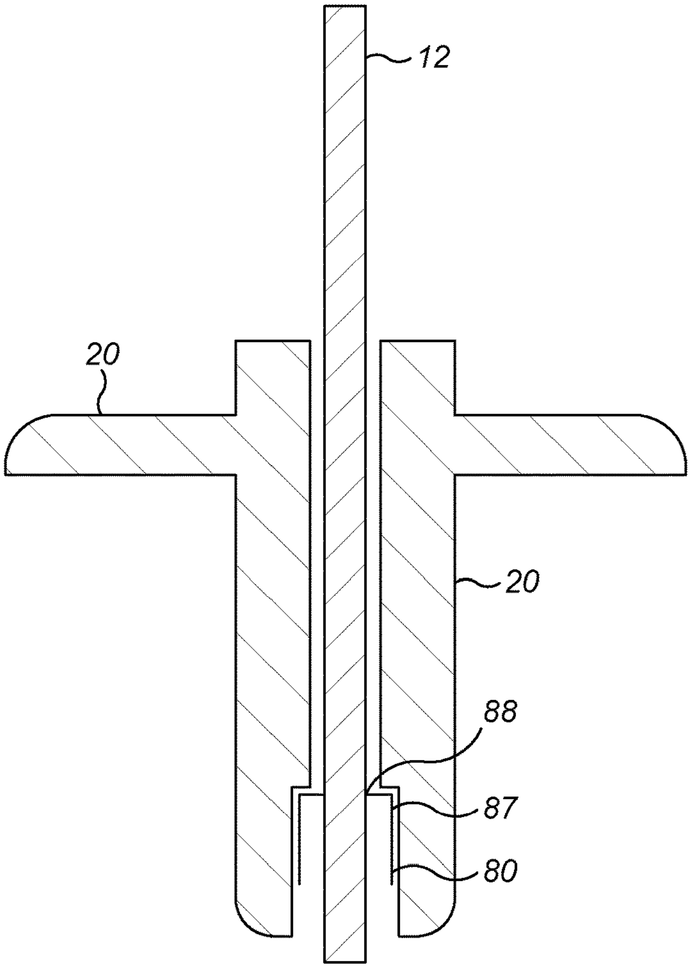

FIGS. 4*a* to 4*f* shows another embodiment of the invention. The string 2 is typically very sticky when wet and adheres to the outer surface of the string capture rod 12. This can make it difficult to transfer the string from the string capture rod 12 to a string holding cup 28. As shown in FIG. 4*a*, the string collection apparatus comprises a string capture rod 12 and a guard element 20. The apparatus further comprises a string removal means 80 in the form of a thimble shaped element. The string removal element 80 comprises one or more perforations and has a cylindrical wall extending from an upper surface 81, wherein the end of the cylinder opposite to the upper surface is open. With respect to FIG. 4*b*, the string removal element 80 comprises a hole 88 in the upper surface thereof, wherein the hole is dimensioned such that the string capture rod 12 may pass therethrough. As shown in FIGS. 4*c* to 4*f*, as the string capture rod 12 passes through the hole in the string removal means, the string is removed from the string capture rod. As shown, for example, in FIG. 4*d*, the guard element 12 comprises a recess 87 which is shaped such that it may accommodate the string removal means 80. As the string capture rod passes through the hole 88 in the string removal means 80, the string is removed from the string capture rod.

Figure 4B:
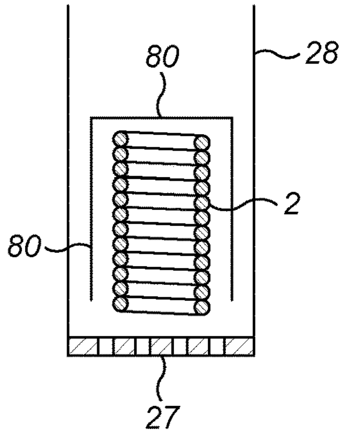
Figure 4D:
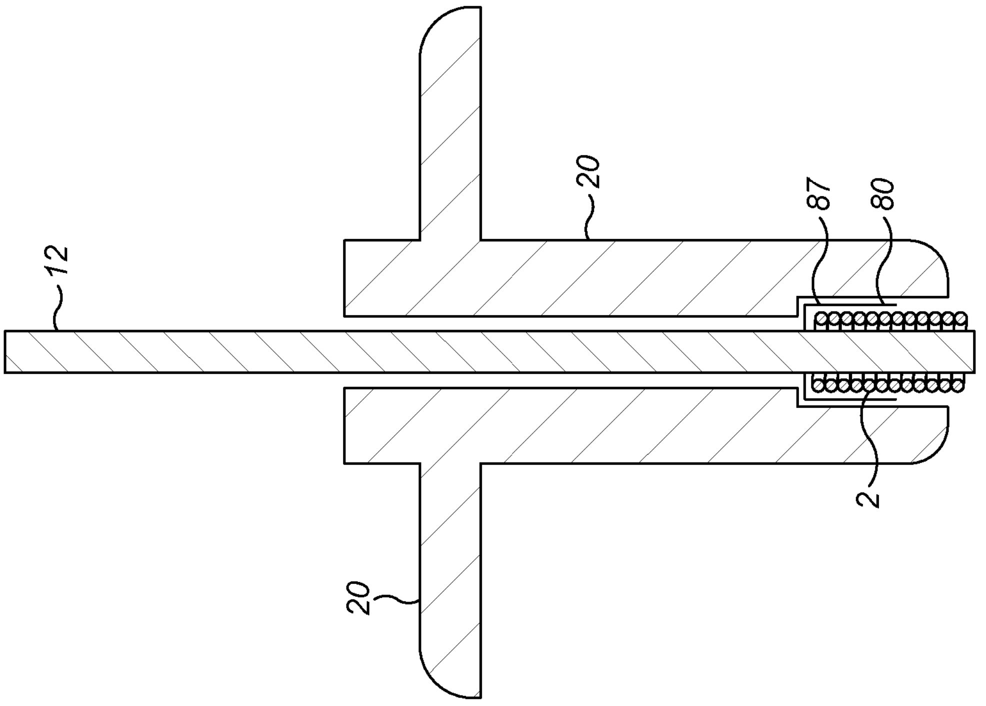
Figure 4C:
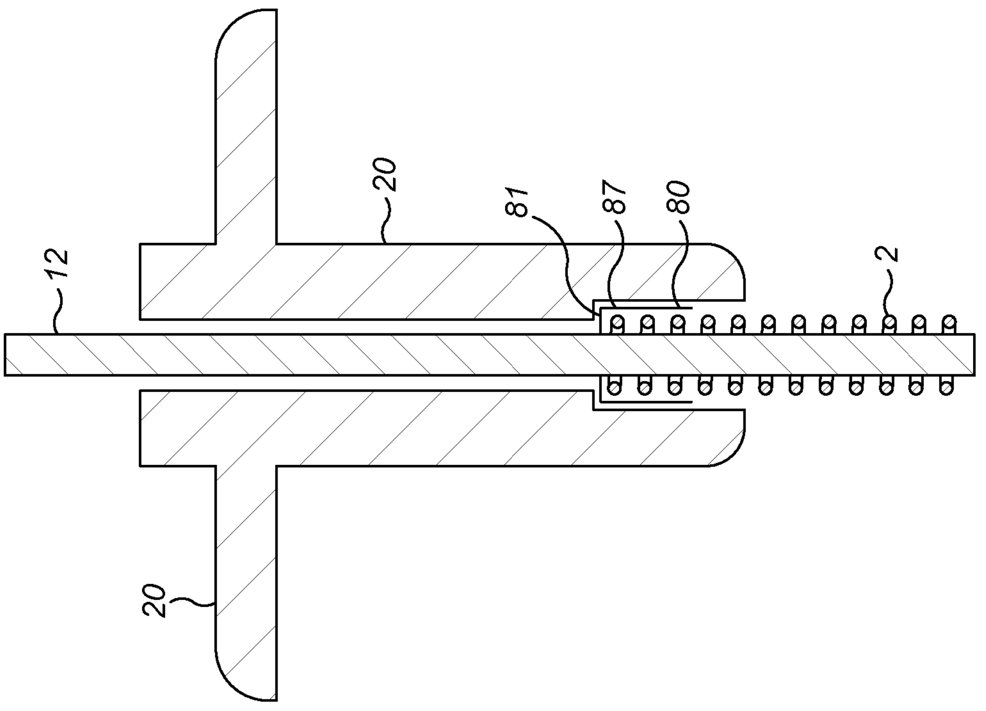
Figure 4E:
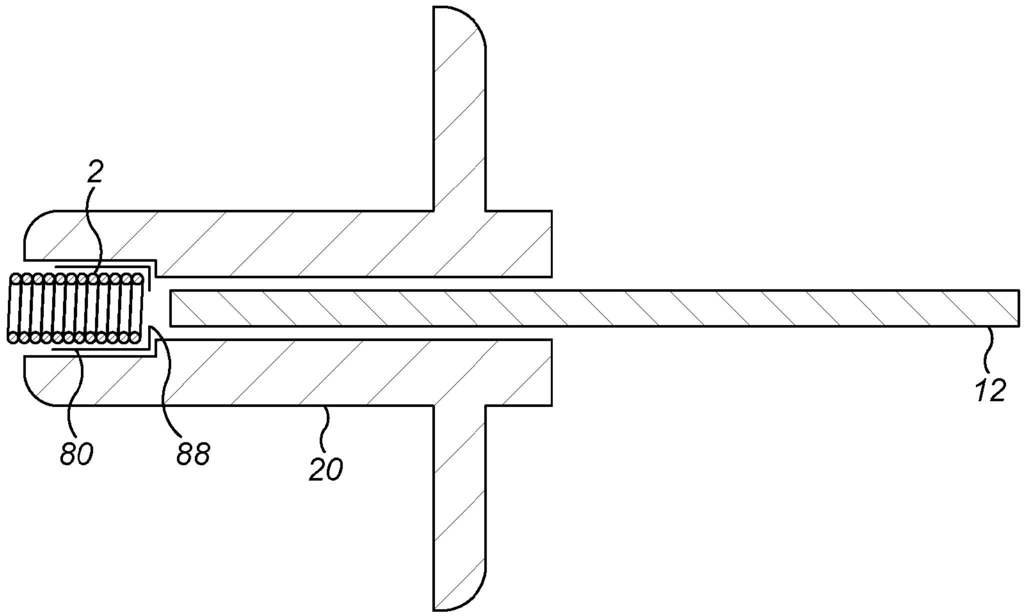
Figure 4F:
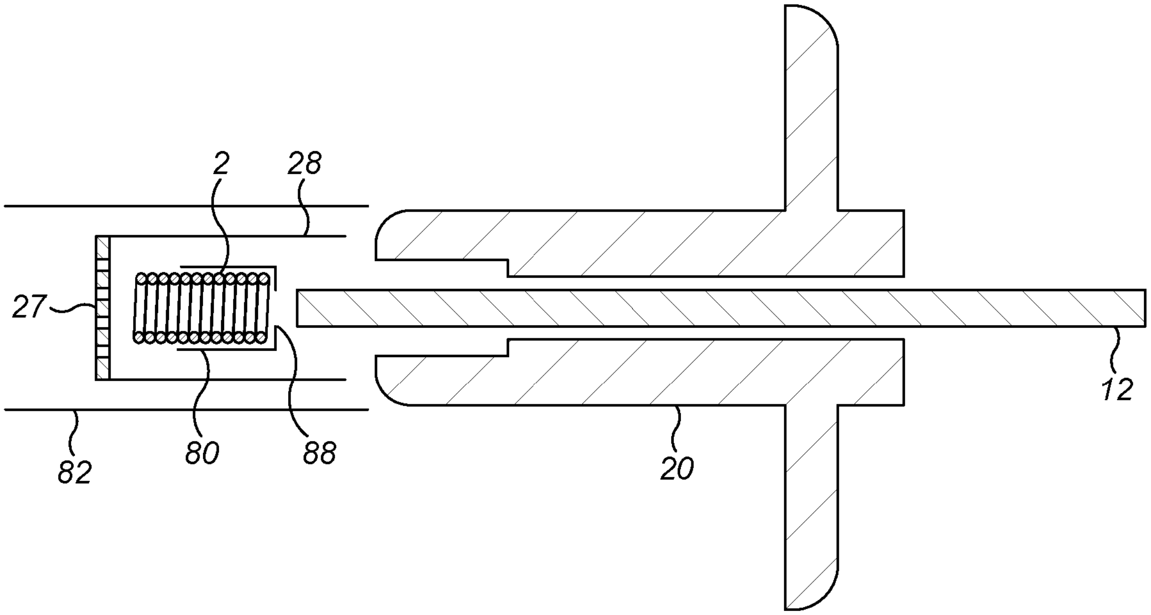

With reference to FIG. 4*a*, the string capture rod 12 is inserted through the cylindrical portion of the guard element 20. The string capture rod 12 passes through the hole 88 provided in the upper surface 81 of the string removal means 80. Preferably, the string removal means is housed within the recess 87 of the guard element. As shown in FIG. 3*d*, the string capture rod 12 is withdrawn into the guard element 12 and then pushed forwards such that the string removal means 80 is placed into the string holding cup 28. As shown in FIGS. 4*b* and 4*f*, the string removal means 80 is held within the string holding cup 28 and the string capture rod 12 is removed from the string removal means 80. The perforations in the string removal means 80 allow buffer to pass through the string removal means and onto the string. The string holding cup is held within the fluid collection tube 82. The perforations 32 at the end of the string holding cup 28 allow buffer to flow over the string and into the fluid collection tube.

FIGS. 5*a* to 5*f* show a string holder 150 that may be provided in one embodiment of the invention. The string holder 150 comprises a flexible disc region 156 comprising a front conical projection 154 onto which the string 2 is wound and a rear cylinder 152 where the remaining string is wrapped. Advantageously, the string holder may be used to preserve the shape and integrity of the coil provided at the proximal end of the string. The string 2 is coiled around the string holder 150 and then placed in a sealed package 158 until ready for use. Advantageously, the provision of a sealed package allows the string to be kept sterile. In one embodiment, a single package may be provided. In another embodiment, the package may be provided comprising the centrifuge activated device and instructions of how to operate the device. Typically, once removed from the packaging 158 the string is unwound from the rear cylinder and the distal end of the string is fixed to the cheek of a patient as described above. The string 2 which is wound around the front conical projection 154 remains in place until the patient is ready to swallow the string. At this point, gentle squeezing of the outer edge of the string holder 150 compresses the conical holder, thus reducing the diameter of the holder and allowing the string to be removed therefrom. The string holder may comprise a plurality of segments which may assist in compression of the string holder when squeezed by a user, to facilitate removal of the string. Typically, the released coil of string can then be placed in the mouth of the patient and swallowed. Following use, the string holder may be discarded. Typically, the string holder comprises a plastics material. Typically, the plastics material is smooth, stiff and flexible. Typically, the string holder comprises a plurality of sections which assist in the compression of the holder to facilitate removal of the string.

Advantageously, the string holder 150 allows the string to be packaged and protects the string and particularly the coiled part of the string from damage prior to use.

With reference to FIG. 5*d*, the string is wrapped around the front conical portion 154. The remaining part of the string is wound around the rear portion 152. At least one slit 157 is provided at the rear of the string holder to allow for easy removal of the string from the holder. In addition, the at least one slit 157 may hold the string in place when being stored. Squeezing the outer rim of the string holder at region 156 will reduce the calibre and/or diameter of the coil holder 150 allowing the coil of string 2 to be easily removed from the holder. The string is stored in region 152 which advantageously protects the string and particularly the coiled part of the string from damage prior to use.

FIGS. 5*e* and 5*f* show string wrapped around the string holder 150, wherein the string may be wrapped around both the front conical projection 154 and the rear cylinder 152.

FIG. 6*a* shows another embodiment of a string holder comprising a string capture rod 12 and guard element 20. In addition, this embodiment comprises a rear portion 152 around which the string may be coiled prior to use. In this embodiment, the string 2 is wound around the string capture rod 12 and the remaining string is passed to the rear unit 152 and coiled for storage. The embodiment shown in FIG. 6 is a string holder and string capture unit. Advantageously, combining the string transport device and string collection device allow for the provision of a dual purpose unit. In this embodiment, the string can be captured and then stored using one unit. This embodiment can be used to store and transport the string but can also be used to collect the string once used and dispense into the tube with the centrifuge activated device.

With reference to FIG. 6*b*, the string capture rod 12 may be used to collect the string coil. In addition, the string capture rod 12 may be used to place the string once used in a substrate container (i.e. string holding device). Typically, the string capture rod 12 is slid with respect to the guard element 20 to transfer the string to a substrate container. The rear portion 152 is used to hold the bulk of the string distal to the coil for storage prior to use. In this embodiment, the string capture rod 12 may be used to capture the string. The string capture rod 12 may also be used to help place the string 2 in a substrate container following use. The part of the guard 20 that is cylindrical and surrounds the string capture rod 12 may act as a sliding device to place the string in a substrate tube or string collection tube once used. The rear part 152 may be used to hold the bulk of the string 2 that is distal to the coil, for storage of the string.

FIGS. 6*c* and 6*d* show a string holder 150 in combination with string 2. In this embodiment, the string 2 is wrapped around a string capture rod 12. The string may also be wrapped around rear cylinder 152. In this embodiment, the string 2 is captured by the string capture rod 12 and stored by the rear cylinder 152. Advantageously, the string holder 150 of this embodiment may be used to store and transport string and also to collect string once used and then dispense the string into a string collection device or tube, for example, using a centrifuge activated device.

FIGS. 7*a* and 8*b* show packaging 158 that may be used to store the string holder prior to use. FIG. 7*b* shows a string holder according to an embodiment of the invention, wherein the string may be wound around portions 12 and 152. The assembled components may be covered with a protective clear plastic overlay. In FIG. 8*a*, the packaging may comprise a string container, an elution buffer, a string substrate container and instructions. The serial number and additional information may be provided on a paper base of the packaging.

FIG. 8*a* shows packaging that may be used to package a centrifuge activated device and/or a string holder in accordance with an embodiment of the invention. Advantageously, the provision of packaging 158 allows the string holder 150 and/or centrifuge activated device 62 to be maintained in a sterile condition prior to use. In one embodiment, the packaging may be used to package a string storage and string capture device. The packaging may be used to package a string storage device and capture device, buffer for the centrifuge activated device and instructions 172.

FIG. 8*b* shows a plastic holder 158 that may be used to package the string storage device and string capture device, wherein the packaging may further comprise a paper cover including labels and a serial number.

With reference to FIG. 9, the string collection apparatus 14 comprises a string holding cup 28 which holds the string after removal from the oesophagus of a patient. The string collection apparatus 14 further comprises a fluid collection tube 30 for holding the string holding cup 28. The string holding cup comprises a cylindrical wall 25 extending from and surrounding a base 27, wherein the base comprises at least one hole 32. The at least one hole 32 has a diameter which allows the passage of oesophageal secretions through the string holding cup during centrifugation. In the embodiment shown in FIG. 5, the at least one hole has a diameter of approximately 0.1 mm. The end of the string holding cup 28 that is opposite to the base is open. The string holding cup is of sufficient diameter to fit the string capture rod and is of sufficient diameter to fit the rounded tip of the string capture rod. The user transfers the string from the patient to the string holding cup via the string capture rod.

The string holding cup 28 fits within a fluid collection tube 30, wherein the open end of the string holding cup fits within the fluid collection tube 82. The fluid collection tube is cylindrical and has a base at one end. Typically, the string holding cup and/or the fluid collection tube comprise a plastics material. In the embodiment shown in FIG. 5, the string holding cup and/or fluid collection tube may hold a volume of approximately 2 ml.

The string holding cup 28 and the fluid collection tube 30 are placed within a centrifuge tube. Typically, the centrifuge tube is a 15 ml centrifuge tube. The adhesive patient identifier can be removed from the proximal end of the string and placed on the outer surface of the centrifuge tube. During centrifugation, the perforations in the string collection cup allow fluid released from the string to be collected at the bottom of the fluid collection tube. Following centrifugation the string holding cup can be removed from the fluid collection tube and the fluid can be analysed in a laboratory.

The fluid collection tube 30 comprising perforations can also be seen in FIGS. 9*a* and 9*b*. FIG. 10 shows a buffer holder 102 in combination with piercing device 42.

The inner surface 34 of the fluid collection tube 30 is tapered such that the diameter at a substantially central portion along the longitudinal length of the tube is less than the diameter at the end of the tube. Advantageously, the reduced diameter along the longitudinal length of the inner surface of the fluid collection tube assists in holding the string holding cup in place, allowing the string holding cup to be removed by a user when required, but preventing the string holding cup from slipping further down the length of the fluid collection tube when centrifuged.

With reference to FIG. 10, the string extraction apparatus 16 comprises a cap 36 comprising a retaining ring 38 which is adapted to engage with a container 40 comprising an extraction buffer. The string extraction apparatus further comprises a piercing device 42. The string extraction apparatus 16 engages with the string collection apparatus 14 during centrifugation, wherein the piercing device 42 sits adjacent to the string holding cup 28 during centrifugation.

The piercing device 42 comprises a spike 44. In the embodiment shown in FIG. 11, the piercing device 42 comprises a disk portion 46, wherein the spike 44 is positioned at a position substantially at the centre of the disk portion. The spike extends from a substantially central portion of the disk portion. In one embodiment, the disk portion of the piercing device comprises a plastics material and the spike of the piercing device comprises a metallic material. The piercing device comprises at least one hole or perforation 48. The retaining ring 38 sits between the container 40 comprising the extraction buffer and the piercing device 44 and is adapted to prevent contact of the spike of the piercing device with the container comprising the extraction buffer prior to centrifugation. The spike 44 of the piercing device 42 is adapted to puncture the container comprising the extraction buffer during centrifugation. Advantageously, the at least one hole or perforation 48 provided within the piercing device distributes the buffer evenly over the string which is held within the string holding cup.

FIGS. 11*a* and 11*b* show a centrifuge activated device in accordance with an embodiment of the invention, comprising a fluid collection tube 30 and a piercing device 42. The membrane 103 of the buffer holder lid is also shown in the format before piercing has occurred.

FIG. 12*a* shows a centrifuge activated device 62 in accordance with another embodiment of the invention, without a buffer holder. Perforations 32 are provided to transfer the buffer to a substrate. FIGS. 12*b* to 12*d* show a centrifuge activated device and a piercing device 42. In this embodiment, the membrane 103 has been pierced by the piercing device during centrifugation, thus allowing buffer release. FIG. 12*d* shows a centrifuge activated device in combination with a buffer holder 102 and piercing device 42.

FIGS. 13*a* and 13*b* show a centrifuge activated device 62 in accordance with another embodiment of the invention, comprising a buffer holder and a piercing device 42. This embodiment is prior to centrifugation, so the piercing device has not yet pierced the membrane of the lid of the buffer holder.

FIG. 14*a* shows a centrifuge activated device comprising a buffer holder in a pierced position. FIG. 14*b* shows a piercing device 42 which may be used to create triangular valves in the buffer holder. FIG. 14*c* shows the piercing device in the activated pierced position, following centrifugation, allowing for buffer release.

FIGS. 15*b* and 15*c* show a piercing member 42 and a buffer holder 50 comprising a retaining ring 52. In this embodiment, the retaining ring 52 is in a closed position. The lid of the buffer holder 50 is held back by the retaining ring. In this embodiment, the piercing member 42 cannot puncture the membrane of the buffer holder.

With reference to FIG. 16, the retaining ring 52 is shown to be in an open position. In this embodiment, the lid of the buffer holder opens the retaining clip 52 and is forced onto the piercing device by g forces. Thus, the lid of the buffer holder is punctured by the piercing device 42.

FIG. 17*a* shows a centrifuge activated device comprising a 15 mm salivette tube (which may be a string holding cup and/or fluid collection tube). The apparatus shown in FIG. 17*b* comprises a buffer holder (e.g. a bottle), which is placed in a centrifuge with the salivette tube (e.g. string holding cup) containing the string and/or a substrate. During centrifugation, the piercing device 42 pierces the buffer holder and the buffer is released, passing over the string. A hole 103 is provided in the salivette chamber and the buffer passes into a 15 ml tube where the eluted fluid is collected.

FIG. 18*a* shows a substrate (i.e. string) holder 28 which may engage with a lid having a buffer and a buffer release mechanism. The lid with the buffer and buffer release mechanism is shown at the right side of this figure (at the part illustrated with reference numeral 30). FIG. 18*b* shows the substrate holder 28 in combination with a lid comprising a buffer holder and a piercing device 42. A retaining ring 52 is also provided. During centrifugation, the piercing device moves against the retaining ring and punctures the membrane of the lid of the buffer holder. The lower section of the substrate holder retains eluted material after centrifugation that is ready for analysis.

A similar embodiment is shown in FIG. 19, wherein FIG. 19*a* shows a substrate holder 28 and buffer release mechanism which are combined, preactivation, by centrifugation. With reference to FIG. 19*b*, the lower end of the substrate holder 28 retains eluted material after centrifugation, wherein the eluted material is then ready for analysis.

FIGS. 20*a* and 20*b* show a buffer holder, a retaining ring 52 and a piercing device 42. These components combine to form a lid that fits over the substrate holder. With reference to FIG. 20*c*, perforations 32 are provided at the bottom of the container 28 to allow for the released buffer to pass through the holes and onto the string or substrate.

FIGS. 21*a* to 21*d* shows lids and stoppers that may be used in combination with a buffer holding container or bottle according to an embodiment of the invention.

FIGS. 22*a* to 22*c* shows a buffer holding container 102 such as a bottle in combination with a retaining ring 52 in accordance with an embodiment of the invention. FIG. 22*b* shows the retaining ring 52 in a closed position. In this embodiment, the buffer holder 102 is prevented from moving forward by the retaining ring 52. With reference to FIG. 52*c*, during centrifugation, under g forces the buffer container lid pushes open the retaining ring such that the lid is then moved into contact with the piercing member 42.

In the embodiment shown in FIG. 23*a*, the piercing device 42 may comprise an L-shaped piercing device. Preferably, the L-shaped piercing device creates a triangular valve 94 in the cap or stopper when pierced. Typically, the valve opens under the centrifuge g forces to release the liquid.

In the embodiment shown in FIG. 23*a*, the L-shaped piercing device may be provided on a base 90, comprising a plurality of perforations 92, wherein the base acts as a support. Typically, the tip 96 may pierce the rubber seal of the container comprising the buffer. Advantageously, a valve 94 is created as the tip pierces the seal of the container which allows the liquid buffer to pass onto the perforated base. Typically, the liquid is then distributed through the perforations and onto the string within the container.

In the embodiment shown in FIG. 23*b*, the piercing device 42 may comprise a star shaped pyramid piercing device. Advantageously, the use of a piercing device having this shape creates a number of triangular valves 94 in the seal when pierced. The valves open under the centrifuge g forces to release the liquid. In this embodiment, four valves may be created.

FIGS. 24*a*, 24*b* and 24*e* show the lid of the buffer holder in combination with piercing device 42. FIG. 24*c* shows a cross section of a piercing device 42 in one embodiment of the invention, wherein the triangular shape and channels 43 can be seen. Advantageously, the channels 43 aid the flow of buffer out of the buffer holder. With reference to FIG. 24*e*, when the buffer lid is cut by the piercing device, triangular shaped cuts are formed in the lid creating four valves, 1 to 4 as shown in this figure.

Figure 25C:
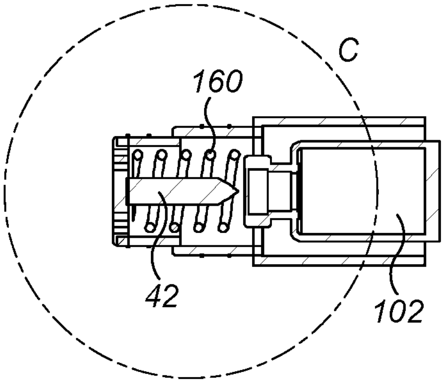
Figure 25D:
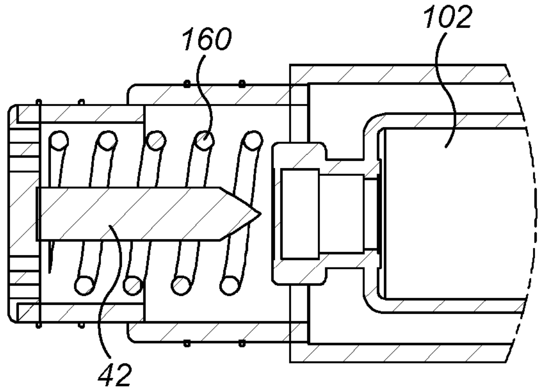
Figure 25E:
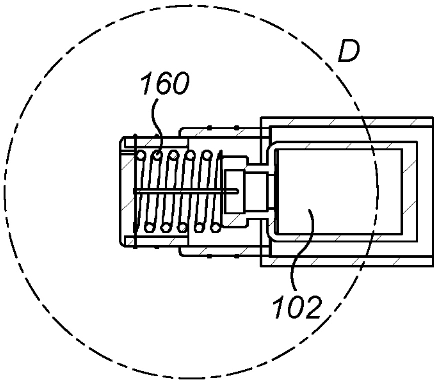
Figure 25F:
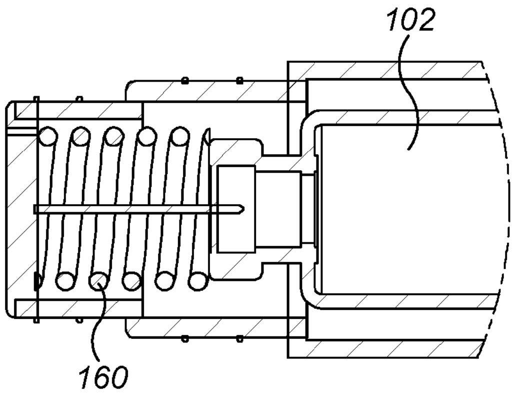

FIG. 25*a* shows a centrifuge activated device per centrifugation and FIG. 25*b* shows a centrifuge activated device during or post centrifugation. FIG. 25*c* shows a section C which is further illustrated in FIG. 25*d*. In this embodiment, piercing device is surrounded by uncompressed spring 160. FIG. 25*e* shows section D which is illustrated in FIG. 25*f*, which shows the spring having been compressed by g forces. In this embodiment, the buffer holder is pierced, releasing liquid under g forces.

FIG. 26*a* shows a centrifuge activated device 62 in combination with a buffer holder. FIG. 26*b* shows section B which is further illustrated in FIG. 26*b*. In this embodiment, the spring is provided in an open, non compressed, position, preventing the buffer holder from containing the piercing device 42.

FIG. 27*a* shows a centrifuge activated device in combination with a spring dampner. FIG. 27*b* shows section B which is further illustrated in FIG. 27*b*. In this embodiment, the spring is compressed by g forces and allows the lid of the buffer holder to be pierced to release buffer.

In another embodiment, the kit comprises a lid which may be used to seal the fluid collection tube 30 and/or string holding cup 28. In one embodiment, the lid may comprise an extraction buffer. In one embodiment, the lid may comprise a release mechanism, wherein when the lid is placed on the fluid collection tube 30 and/or string holding cup 28, the extraction buffer is released into the string holding cup 28. In one embodiment, the release mechanism comprises a latch member. In this embodiment, the latch member may be released when the cap is placed on the string holding cup and/or fluid collection tube. Typically, the release of the latch mechanism may result in puncture of the lid comprising the extraction buffer such that the buffer passes over the string that is held within the string holding cup. In another embodiment, when the lid comprising the extraction buffer is placed onto the fluid collection tube and/or string holding cup, a spike held within or adjacent to the lid and/or fluid collection container punctures the lid and causes release of the extraction buffer. In one embodiment, the spike may be held within the lid and the action of placing the lid onto the fluid collection tube and/or string holding cup causes the spike to puncture the portion of the lid holding the extraction buffer, thus causing release of the extraction buffer.

In one embodiment, the retaining ring 38 and release member may be used together to prevent unwanted puncture of the container comprising the extraction buffer. In one embodiment, the retaining ring 38 comprises a first safety device to prevent unwanted release of the extraction buffer from the container comprising the extraction buffer. In one embodiment, the release member comprises a second safety device to prevent unwanted release of the extraction buffer. In this embodiment, the second safety device is disarmed by putting the lid onto the fluid collection tube 30 and/or string holding cup 28. In one embodiment, the first and/or second safety device may be disarmed to cause release of the extraction buffer from the container comprising the extraction buffer and/or lid comprising the extraction buffer, for example, during centrifugation.

With reference to FIG. 21*d*, the fluid collection apparatus may comprise a bottle 102. Preferably, the bottle is standardised for use with a centrifuge activated device. Preferably, the bottle is sealed with a rubber stopper 100 (as shown, for example, in FIG. 21*b*) and a crimp cap 104 (as shown, for example, in FIG. 21*a*). The stopper and cap combination is shown in FIG. 21*c*. Preferably, the crimp cap is 13 mm in diameter and comprises a silver material. In one embodiment, the crimp cap may be a commercially available crimp seal, such as that provided by Fisherbrand™. In one embodiment the bottle may be commercially available. Advantageously, the combination of the stopper which is held in place by the cap provides a liquid tight seal. Preferably, the bottle is provided within the lid of the kit, wherein the bottle is used in combination with the string collection apparatus. In this embodiment, it is preferred that the piercing device comprises a needle like device. Preferably, the needle like device is sharp to allow the stopper and seal to be punctured. Preferably, the needle like device is hollow to allow the liquid under the g forces of centrifugation to flow through the needle and onto the string that is held within the bottle. Preferably, a disk is provided within the bottle and substantially parallel to the plane of the base of the bottle. Preferably, the disk comprises a plurality of holes, such that as the liquid passes through the needle, the liquid is distributed evenly onto the string.

There is also provided a method of providing a structure at the distal end of the string 2 of the apparatus of FIG. 1, comprising the step of modifying the string to form a structure at the distal end 6. The string is modified to form a helical structure at the distal end. The method comprises the steps of coating the distal end of the string in a solution which will confer rigidity to the string when dry, wrapping the distal end of the string around a rod to form a helical structure and allowing the string to dry. In one embodiment, the string may be soaked in a solution comprising a sugar. In another embodiment, the string may be soaked in a solution of corn starch, such as 1% corn starch solution. Advantageously, the helical component at the distal end of the string provides a structure that is flexible and soft to assist in insertion into the oesophagus of a patient, yet rigid to assist in the patient swallowing the string. The size of the structure at the distal end of the string is optimised such that it is small enough that it does not cause irritation to the oesophagus, whilst still being capable of being swallowed by a patient. In one embodiment, the size of the structure at the distal end of the string is equivalent to a size 5 capsule (having a length of approximately 11.1 mm and a width of approximately 4.9 mm), but can be of larger or smaller size if needed.

There is also provided a method of determining the presence of a substance within a patient using the apparatus of FIGS. 1 to 27, the method comprising the steps of providing a structure 8 at the distal end 6 of the string 2 to assist the patient in swallowing the string, removing the string from the oesophagus of the patient and testing the string to check for the presence of the biological substance. The method may comprise the step of applying a marker such as a protein or dye to the string prior to insertion into the patient. The string may be coated with a biological macromolecule such as a protein which may act as a marker for a condition. In one embodiment, the string is coated with eosinophilic cationic protein (ECP). In another embodiment, the string may be coated with a dye or other marker.

The method may comprise the step of absorbing a component following insertion into the oesophagus of a patient. In one embodiment, when the string has been inserted into the oesophagus of a patient, the string absorbs a protein such as eosinophilic cationic protein (ECP). ECP is known to be a marker for the condition eosinophilic esophagitis (EoE), such that the detection of this protein may indicate that the patient is suffering from this condition and falling ECP levels indicate response to treatment.

Segments of the string may be analysed separately following removal of the string from the oesophagus of a patient. In one embodiment, the method may comprise the step of providing an interval marker on the string. In one embodiment, the interval marker may comprise an ink or dye. In another embodiment, the interval marker may comprise at least one knot provided on the string. Typically, following removal of the string from a patient, the string may be cut at the intervals shown by the interval markers and individual segments may be analysed separately.

In one embodiment, the method comprises the step of coating the string with a substance that will provide a stimulus to the oesophageal lining of the patient. In one embodiment, the string may be coated with a substance that will provoke an inflammatory response by the oesophageal lining of the patient. Typically, the substance that provides a stimulus will interact with other biological mediators that are released in response. Typically, the method comprises the step of coating the string with a biological substance, a chemical substance or a food. In one embodiment, the method comprises the step of coating the string with a cytokine, a weak acid or alkaline substance or a food, such as a whole food or a food component. In one embodiment, the method comprises the step of coating the string with whole milk. In another embodiment, the method comprises the step of coating the string with ovalbumin. In one embodiment, the method comprises the step of marking the string using a dye or providing a knot within the string to act as a marker. In this embodiment, string segments on either side of the stimulus can be removed (e.g. cut out) and biological components of inflammation measured as indicated above (see Adaption 3). In the embodiment wherein the provoking stimulus is applied to the string, the method comprises the step of coating the section of the string provided with the stimulus with a protective film to protect the stimulus from being washed away during the swallowing process. In this embodiment, the protective film comprises a dissolvable substance such as gelatine, wherein the dissolvable substance will dissipate once in place to reveal the stimulus.

The method further comprises the step of analysing the string following removal from the oesophagus of the patient to check for any biological components that may have bound to the string when it was inserted in the patient.

The method comprises the step of using a string capture rod 12 to transfer the string following removal from a patient to a string collection apparatus. Advantageously, the use of a string transfer rod to transfer the string minimises sample contamination and reduces user risk. The string is wound around the outer surface of the cylindrical element 18 of the string capture rod. The user then slides the guard element 20 of the string capture rod along the longitudinal axis of the string capture rod such that the string is pushed along the cylindrical element and into an appropriate container for transfer to the laboratory.

The string 2 is transferred from the string capture rod 12 to a string collection apparatus 14 comprising a string holding cup 28. The string holding cup 28 holds the string 2 after removal from the oesophagus of a patient. The user transfers the string from the patient to the string holding cup 28 via the string capture rod 12.

The method further comprises the step of providing a fluid collection tube 30 which is dimensioned to hold the string holding cup 28.

The method further comprises the step of providing a string extraction apparatus 16 to assist in extracting the biological marker from the string. The method comprises the step of providing a cap 36 comprising a retaining ring 38, wherein the retaining ring 38 engages with a container 40 comprising an extraction buffer. The string extraction apparatus 16 engages with the string collection apparatus 14 during centrifugation. Prior to centrifugation, the string 2 is placed within the string holding cup 28 of the string collection apparatus 14 and the string collection apparatus 14 and string extraction apparatus 16 are placed within a centrifuge tube.

During centrifugation, the spike 44 of the piercing device 42 punctures the container 40 comprising the extraction buffer. The extraction buffer is then transferred into the string holding cup 28, washes over the string 2 and passes through the at least one hole 27 provided within the base of the string holding cup 28. Typically, as the extraction buffer washes over the string it causes a biological component such as a protein that has bound to the string to be removed. The biological component passes into the fluid collection tube where it can then be taken for further tests in the laboratory.

The string holding cup 28 and the fluid collection tube 30 are placed within a centrifuge tube. In one embodiment, the centrifuge tube is a 15 ml centrifuge tube. The adhesive patient identifier can be removed from the string and placed on the outer surface of the centrifuge tube. During centrifugation, the perforations 27 in the string holding cup allow fluid released from the string to be collected at the bottom of the fluid collection tube 30. Following centrifugation the string holding cup 28 can be removed from the fluid collection tube 30 and the fluid can be analysed in a laboratory.

There is also provided a method of administering a drug to a patient using apparatus comprising a string as shown in FIG. 1. In one embodiment, the method comprises the step of applying a pharmaceutical substance to the distal end 6 of the string 2 which has been adapted to assist the patient in swallowing the string. In another embodiment, the method comprises the step of placing a pharmaceutical substance within the interior of the portion at the distal end of the string which has been adapted to assist the patient in swallowing the string.

There is also provided a method of removing a substance from apparatus comprising a string 2 as shown in FIG. 1 using the process of centrifugation. Advantageously, the use of a centrifuge activated device aims to improve the consistency of removal of substances that are adhered to the string and to save laboratory staff time and simplify the process.

The method comprises the step of placing a string after removal from the oesophagus of a patient into a string collection apparatus as shown in FIG. 10, placing the string collection apparatus and a string extraction apparatus as shown in FIGS. 10 and 11 into a centrifuge tube and using the process of centrifugation to release extraction buffer onto the string. During centrifugation, the piercing structure 44 of the piercing device 42 pierces the container 40 comprising the extraction buffer such that the extraction buffer washes over the string and causes elution of a substance that is bound to the string. Following elution, the substance that was bound to the string is collected for testing in a laboratory.

The act of centrifugation forces the spike 44 to puncture the container 40 comprising the extraction buffer and to release the extraction buffer onto the string.

The forces applied to the system during centrifugation force the container 40 holding the extraction buffer past the retaining ring 38 onto the spike 44 of the piercing device 42. The extraction buffer is released and passes through the at least one hole 48 provided within the piercing device 42 and onto the string 2 that is held within the string holding container 28.

In another embodiment, the extraction buffer may be held within a container comprising a valve that is normally in the closed position. In this embodiment, the force applied to the system during centrifugation causes the valve to open, thus releasing the elution buffer from the container and onto the string.

In another embodiment, the piercing sits within the container holding the extraction buffer and is activated by the g forces that are applied to the system during centrifugation.

FIG. 11 shows another embodiment wherein the string holding cup 28 comprises an extraction buffer and a buffer release mechanism. The buffer is held within container 50 and during centrifugation, the forces applied to the system cause the buffer holding container 50 to move past a retaining ring 52 onto a spike provided on piercing device 42. Extraction buffer is released from the container 50 and passes through the small perforations within the piercing device onto the string below.

In use, the distal end of a string 2 is adapted by soaking the string in a solution comprising, for example, 1% corn starch. The distal end 6 of the string is wound around the outer surface of a metal rod and allowed to dry. Once the string has dried, a protein such as eosinophilic cationic protein (ECP) is applied to the distal end of the string. The string is inserted into the oesophagus of a patient. Advantageously, the provision of the structure provided at the distal end of the string assists in the patient swallowing the string.

The proximal end 4 of the string comprises a structure such as a knotted portion of the string to facilitate attachment of the string to the cheek of a patient. The string may be attached to the patient using medical grade tape. A patient identifier may be added to the proximal end of the string.

The string 2 is then removed from the oesophagus of the patient and transferred to a fluid collection apparatus 14 using a string capture rod 12. The string is wound around the outer surface of the cylindrical element 18 of the string capture rod 12 and the user slides a guard element 20 along the longitudinal length of the cylindrical element 18 to push the string into a string holding cup 28. The string holding cup is held within a fluid collection tube 30.

The string extraction apparatus 16 is placed adjacent to the string collection apparatus 14 and both the string extraction apparatus and the string collection apparatus are placed into a centrifugation tube. The cap of the string extraction apparatus 16 comprises a retaining ring 28 which is adjacent to a container 40 comprising an extraction buffer. A piercing device 42 is positioned adjacent the container comprising the extraction buffer. Prior to centrifugation, the piercing device does not engage the container comprising the extraction buffer. During centrifugations, the forces applied to the system cause the piercing device to puncture the container comprising the extraction buffer. The extraction buffer passes into the string holding cup 28 and washes over the string and through the holes 27 provided in the string holding cup 28. The fluid then passes into the fluid collection tube for further analysis in a laboratory. A neutralisation buffer may be provided within the fluid collection tube to neutralise the extraction buffer, if required.

A DNA and/or RNA stabilising buffer may be used to reduce and/or prevent degradation of the sample prior to analysis. In one embodiment, the DNA and/or RNA stabilising buffer may comprise a TE buffer comprising 10 mM Tris (pH 8.0) with HCl and 1 mM EDTA. Advantageously, the addition of DNA and/or RNA stabilising agents to a sample may prevent contaminants in the saliva of a patient from breaking down nucleotides. In addition, the use of DNA and/or RNA stabilising agents in a buffer can help to stabilise a sample until it can be processed.

In a further embodiment, protein stabilising agents may be added to the buffer, such as protease inhibitors and/or metal chelators. Advantageously, the use of a protein stabilising agent may prevent degradation prior to analysis, and/or may assist in stabilising a sample where specific protein analysis may be needed.

In another embodiment, enzymes may be added to a buffer to remove free DNA and/or RNA that may act as a contaminant.

Preferably, the use of a DNA and/or RNA stabilising buffer and/or protein stabilising agent may assist in stabilising the sample prior to testing in a laboratory.

Advantageously, the use of a DNA and/or RNA stabilising buffer and/or protein stabilising agent may assist in stabilising a saliva sample prior to testing in a laboratory, thus improving the performance of the test.

Typically, the string may be analysed following insertion into a patient to determine whether the distal end of the string has entered the stomach of the patient. Typically, following removal of the string from a patient, the chemical composition of the distal end of the string is analysed. In one embodiment, the pH of the distal end of the string may be analysed, for example using a pH indicator dye or paper. Typically, if the distal end of the string has been present in the stomach of the patient, the pH of the distal end of the string will be acidic, due to the acidic nature of the stomach. In another embodiment, following removal of the string from a patient, the distal end of the string may be analysed to test for other stomach markers such as pepsin or gastrokines. It is preferred that the pH indicator and/or stomach markers are provided with the kit of the invention.

Preferably, a string capture rod may be used to transfer the string following removal from a patient to a string collection apparatus. Advantageously, the use of a string transfer rod to transfer the string minimises sample contamination and reduces user risk. Preferably, the string is wound around the outer surface of the cylindrical element of the string capture rod. Preferably, the user then slides the guard element of the string capture rod along the longitudinal axis of the string capture rod such that the string is pushed along the cylindrical element and into an appropriate container, e.g. for transfer to the laboratory.

Preferably, the string is transferred from the string capture rod to a string collection apparatus comprising a string holding cup. Preferably, the string holding cup holds the string after removal from the oesophagus of a patient. Preferably, the user transfers the string from the patient to the string holding cup via the string capture rod.

A string removal means, such as a thimble like element, may be used to assist in removal of the string from the string capture element. Preferably, as the string capture rod passes through the hole in the string removal means, the string is removed from the surface of the string capture rod. Preferably, the string capture rod is inserted through the cylindrical portion of the guard element. Preferably, the string capture rod is passed through the hole provided in the upper surface of the string removal means. Preferably, the string removal means is housed within the recess of the guard element. Preferably, the string capture rod is withdrawn into the guard element and then pushed forwards such that the string removal means is placed into the string holding cup. Preferably, the string removal means is held within the string holding cup and the string capture rod is removed from the string removal means. Typically, the perforations in the string removal means allow buffer to pass through the perforations in the string removal means and onto the string.

A string holder may be used comprising a disc region comprising a front conical projection onto which the string is wound and a rear cylinder where the remaining string is wrapped. Typically, the disc region comprises a flexible material. Advantageously, the string holder may be used to preserve the shape and integrity of the coil provided at the proximal end of the string. Typically, the string is coiled around the string holder and then placed in a sealed package until ready for use. Advantageously, the provision of a sealed package allows the string to be kept sterile. Typically, once removed from the packaging the string is unwound from the rear cylinder and the distal end of the string is fixed to the check of a patient as described above. Preferably, the string which is wound around the front conical projection remains in place until the patient is ready to swallow the string. Typically, at this point, gentle squeezing of the outer edge of the string holder compresses the conical holder, thus reducing the diameter of the holder and allowing the string to be removed therefrom. Typically, the released coil of string can then be placed in the mouth of the patient and swallowed.

Typically, following use, the string holder may be discarded. Typically, the string holder comprises a plastics material. Typically, the plastics material is smooth, stiff and flexible. In one embodiment, a robot may be used to wrap the string around the string holder and seal the string holder in a package.

In one embodiment, the string holder may also comprise a string capture rod. Advantageously, combining the string transport device and string collection device allow for the provision of a dual purpose unit. In this embodiment, the string can be captured and then stored using one unit. This embodiment can be used to store and transport the string but can also be used to collect the string once used and dispense into the tube with the centrifuge activated device.

A fluid collection tube may then be used which is dimensioned to hold the string holding cup.

Preferably, a string extraction apparatus may be used to assist in extracting the marker from the string. Preferably, the cap may comprise a retaining ring, wherein the retaining ring engages with a container comprising an extraction buffer. Preferably, the string extraction apparatus engages with the string collection apparatus during centrifugation. Preferably, prior to centrifugation, the string is placed within the string holding cup of the string collection apparatus and the string collection apparatus and string extraction apparatus are placed within a centrifuge tube.

Preferably, the spike of the piercing device punctures the container comprising the extraction buffer during centrifugation. Typically, the extraction buffer is then transferred into the string holding cup, washes over the string and passes through the at least one hole provided within the base of the string holding cup. Typically, as the extraction buffer washes over the string it causes a component such as a protein that has bound to the string to be removed. Preferably, the component passes into the fluid collection tube where it can then be taken for further tests in the laboratory.

In one embodiment, the lid may comprise an extraction buffer. In this embodiment, when the lid is placed over the string holding cup and/or fluid collection tube, a release mechanism provided within or adjacent to the lid causes the lid to be punctured, thus removing the extraction buffer from the lid such that it passes over the string within the string holding cup and into the fluid collection tube.

In one embodiment, the lid may comprise a bottle, wherein the bottle may be standardised for use in a centrifuge. Preferably, the bottle may be used in combination with a string holding cup. Preferably, the bottle comprises an extraction buffer. Preferably, the bottle further comprises a stopper and seal. Preferably, the stopper is pierced with a piercing device to release buffer from the buffer and into the string holding cup, wherein the string is held within the string holding cup.

Preferably, the string holding cup and the fluid collection tube are placed within a centrifuge tube. Preferably, the centrifuge tube is a 15 ml centrifuge tube. Preferably, the adhesive patient identifier can be removed from the proximal end of the string and placed on the outer surface of the centrifuge tube. Preferably, during centrifugation, the perforations in the string collection cup allow fluid released from the string to be collected at the bottom of the fluid collection tube. Preferably, following centrifugation the string collection cup can be removed from the fluid collection tube and the fluid can be analysed in a laboratory.

The invention claimed is:

1. An apparatus consisting essentially of a string for insertion into the oesophagus of a patient, the string comprising a proximal end and a distal end, wherein the string forms a coiled structure at the distal end, wherein the structure is configured to enter the stomach and assist in the insertion of the string into the oesophagus of the patient without use of a capsule, wherein the distal end of the string is treated to confer rigidity on the structure and the distal end of the string is more rigid than the proximal end.

2. The apparatus according to claim 1, wherein the string is coated with a marker.

3. The apparatus according to claim 1, wherein the string is coated with or encompasses a pharmaceutical agent for administration to the patient.

4. The apparatus according to claim 1, wherein the string is configured to be used to absorb a biological component following insertion into the oesophagus of the patient.

5. The apparatus according to claim 1, wherein the string is configured to be used to test for eosinophilic cationic protein (ECP).

6. The apparatus according to claim 1, wherein a segment of the string is coated with a substance which provides a stimulus to oesophageal lining.

7. The apparatus according to claim 6, wherein the segment of the string coated with the stimulus is covered with a protective film to protect the stimulus from being washed away during the swallowing process.

8. The apparatus according to claim 1, wherein the string comprises a plurality of strings for insertion into the oesophagus of the patient, wherein the plurality of strings form the structure at the distal end thereof.

9. A method of providing the structure at the distal end of the string of the apparatus of claim 1 to assist in insertion of the string into the oesophagus of the patient, the method comprising modifying the string to form a compressed pellet of string at the distal end.

* * * * *